US010987069B2

(12) United States Patent
Roth et al.

(10) Patent No.: US 10,987,069 B2
(45) Date of Patent: Apr. 27, 2021

(54) NUCLEAR MEDICINE TOMOGRAPHY SYSTEMS, DETECTORS AND METHODS

(71) Applicant: Spectrum Dynamics Medical Limited, Road Town (VG)

(72) Inventors: Nathaniel Roth, Tel-Aviv (IL); Yoel Zilberstein, Herzlia (IL); Shlomo Ben-Haim, London (GB); Benny Rousso, Rishon-LeZion (IL)

(73) Assignee: Spectrum Dynamics Medical Limited, Road Town (VG)

( * ) Notice: Subject to any disclaimer, the term of this patent is extended or adjusted under 35 U.S.C. 154(b) by 588 days.

(21) Appl. No.: 14/399,975

(22) PCT Filed: May 8, 2013

(86) PCT No.: PCT/IB2013/053721
§ 371 (c)(1),
(2) Date: Nov. 10, 2014

(87) PCT Pub. No.: WO2013/168111
PCT Pub. Date: Nov. 14, 2013

(65) Prior Publication Data
US 2015/0119704 A1 Apr. 30, 2015

Related U.S. Application Data

(60) Provisional application No. 61/788,394, filed on Mar. 15, 2013, provisional application No. 61/646,333, (Continued)

(51) Int. Cl.
*A61B 6/03* (2006.01)
*A61B 6/04* (2006.01)
(Continued)

(52) U.S. Cl.
CPC ............ *A61B 6/037* (2013.01); *A61B 6/0407* (2013.01); *A61B 6/4258* (2013.01);
(Continued)

(58) Field of Classification Search
CPC ..... A61B 6/037; A61B 6/0407; A61B 6/4245; A61B 6/4266; A61L 36/037; A61L 6/0407; A61L 6/4245; A61L 6/4266
See application file for complete search history.

(56) References Cited

U.S. PATENT DOCUMENTS 3,777,148 A    12/1973   Miraldi
4,195,227 A *   3/1980   Carman ................ G01T 1/2985
                                                                                        250/505.1
(Continued)

FOREIGN PATENT DOCUMENTS

FR            2697918       5/1994
WO     WO 02/16965    2/2002
(Continued)

OTHER PUBLICATIONS

Bruyant, "Analytic and Iterative Reconstruction Algorithms in SPECT*" J Nucl Med. Oct. 1, 2002, vol. 43, No. 10, pp. 1343-1358.*
(Continued)

*Primary Examiner* — Katherine L Fernandez
*Assistant Examiner* — Colin T. Sakamoto

(57) ABSTRACT

An N-M tomography system comprising: a carrier for the subject of an examination procedure; a plurality of detector heads; a carrier for the detector heads; and a detector positioning arrangement operable to position the detector heads during performance of a scan without interference or collision between adjacent detector heads to establish a variable bore size and configuration for the examination. Additionally, collimated detectors providing variable spatial
(Continued)

resolution for SPECT imaging and which can also be used for PET imaging, whereby one set of detectors can be selectably used for either modality, or for both simultaneously.

41 Claims, 29 Drawing Sheets

Related U.S. Application Data filed on May 13, 2012, provisional application No. 61/644,120, filed on May 8, 2012.

(51) Int. Cl.
  *G01T 1/16* (2006.01)
  *G21K 1/02* (2006.01)
  *A61B 6/00* (2006.01)
  *A61B 6/10* (2006.01)

(52) U.S. Cl.
  CPC .......... *A61B 6/4266* (2013.01); *A61B 6/4275* (2013.01); *A61B 6/4291* (2013.01); *A61B 6/447* (2013.01); *A61B 6/4429* (2013.01); *G01T 1/1603* (2013.01); *G21K 1/025* (2013.01); *A61B 6/102* (2013.01); *A61B 6/4417* (2013.01); *A61B 6/4494* (2013.01); *A61B 6/5205* (2013.01)

(56) References Cited

U.S. PATENT DOCUMENTS

| | | | |
|---|---|---|---|
| 4,204,123 A * | 5/1980 | Stoddart | G01T 1/2985 |
| | | | 250/363.04 |
| 4,358,856 A | 11/1982 | Stivender et al. | |
| 4,363,128 A | 12/1982 | Grady et al. | |
| 4,859,852 A | 8/1989 | Genna et al. | |
| 5,198,680 A | 3/1993 | Kurakake | |
| 5,206,512 A * | 4/1993 | Iwao | A61B 6/037 |
| | | | 250/363.04 |
| 5,444,252 A * | 8/1995 | Hug | A61B 6/037 |
| | | | 250/363.05 |
| 5,585,637 A | 12/1996 | Bertelsen et al. | |
| 5,825,031 A * | 10/1998 | Wong | G01T 1/164 |
| | | | 250/363.03 |
| 5,841,140 A | 11/1998 | McCroskey et al. | |
| 5,929,446 A | 7/1999 | Plummer et al. | |
| 5,967,983 A | 10/1999 | Ashburn | |
| 6,137,109 A | 10/2000 | Hayes | |
| 6,173,201 B1 | 1/2001 | Front | |
| 6,368,331 B1 | 4/2002 | Front et al. | |
| 6,567,687 B2 | 5/2003 | Front et al. | |
| 6,707,884 B1 | 3/2004 | Ogawa | |
| 6,744,053 B2 * | 6/2004 | Wong | G01T 1/1615 |
| | | | 250/363.03 |
| 6,789,941 B1 | 9/2004 | Grady | |
| 7,176,466 B2 | 2/2007 | Rousso et al. | |
| 7,498,582 B2 | 3/2009 | Joung | |
| 7,652,259 B2 | 1/2010 | Kimchy et al. | |
| 7,826,889 B2 | 11/2010 | David et al. | |
| 7,872,235 B2 | 1/2011 | Rousso et al. | |
| 7,968,851 B2 | 6/2011 | Rousso et al. | |
| 7,970,455 B2 | 6/2011 | Zilberstein et al. | |
| 8,000,773 B2 | 8/2011 | Rousso et al. | |
| 8,036,731 B2 | 10/2011 | Kimchy et al. | |
| 8,094,894 B2 | 1/2012 | Nagler et al. | |
| 8,111,886 B2 | 2/2012 | Rousso et al. | |
| 8,280,124 B2 | 10/2012 | Dichterman et al. | |
| 8,338,788 B2 | 12/2012 | Zilberstein et al. | |
| 8,445,851 B2 | 5/2013 | Rousso et al. | |
| 2002/0148970 A1 | 10/2002 | Wong et al. | |
| 2003/0001098 A1 | 1/2003 | Stoddart et al. | |
| 2003/0111608 A1 | 6/2003 | Dulmen et al. | |
| 2003/0111609 A1 | 6/2003 | Zeng | |
| 2004/0015075 A1 | 1/2004 | Kimchy et al. | |
| 2004/0054248 A1 | 3/2004 | Kimchy et al. | |
| 2004/0120464 A1 | 6/2004 | Hoffman | |
| 2004/0204646 A1 | 10/2004 | Nagler et al. | |
| 2004/0217292 A1 * | 11/2004 | Moyers | A61B 6/037 |
| | | | 250/363.03 |
| 2004/0251419 A1 | 12/2004 | Nelson et al. | |
| 2005/0017182 A1 | 1/2005 | Joung et al. | |
| 2005/0154315 A1 * | 7/2005 | Nair | A61B 5/02007 |
| | | | 600/467 |
| 2006/0065836 A1 | 3/2006 | Tsuchiya et al. | |
| 2007/0080296 A1 * | 4/2007 | Ueno | G01T 1/2985 |
| | | | 250/363.04 |
| 2007/0194241 A1 | 8/2007 | Rousso et al. | |
| 2007/0221853 A1 | 9/2007 | Joung | |
| 2008/0042067 A1 | 2/2008 | Rousso et al. | |
| 2008/0128626 A1 | 6/2008 | Rousso et al. | |
| 2008/0131362 A1 | 6/2008 | Rousso et al. | |
| 2008/0230702 A1 | 9/2008 | Rousso et al. | |
| 2008/0230705 A1 | 9/2008 | Rousso et al. | |
| 2008/0260637 A1 | 10/2008 | Dickman | |
| 2009/0112086 A1 | 4/2009 | Melman | |
| 2009/0152471 A1 | 6/2009 | Rousso et al. | |
| 2009/0201291 A1 | 8/2009 | Ziv et al. | |
| 2009/0304150 A1 | 12/2009 | Metzler et al. | |
| 2009/0304582 A1 | 12/2009 | Rousso et al. | |
| 2009/0324042 A1 | 12/2009 | Laurence et al. | |
| 2010/0021378 A1 | 1/2010 | Rousso et al. | |
| 2010/0046817 A1 * | 2/2010 | Goedicke | A61B 6/503 |
| | | | 382/131 |
| 2010/0111395 A1 * | 5/2010 | Tamakoshi | A61B 6/469 |
| | | | 382/132 |
| 2010/0142774 A1 | 6/2010 | Ben-Haim et al. | |
| 2011/0024636 A1 * | 2/2011 | Gagnon | G01T 1/2985 |
| | | | 250/362 |
| 2011/0026685 A1 * | 2/2011 | Zilberstein | A61B 6/037 |
| | | | 378/197 |
| 2011/0112856 A1 | 5/2011 | Rousso et al. | |
| 2012/0001077 A1 | 1/2012 | Inoue et al. | |
| 2012/0106820 A1 | 5/2012 | Rousso et al. | |
| 2012/0108948 A1 | 5/2012 | Jansen et al. | |
| 2012/0172699 A1 | 7/2012 | Nagler et al. | |
| 2012/0232385 A1 | 9/2012 | Hattori et al. | |
| 2014/0048713 A1 | 2/2014 | Liu et al. | |
| 2015/0235723 A1 | 8/2015 | Lee et al. | |
| 2018/0000431 A1 | 1/2018 | Roth et al. | |
| 2020/0015763 A1 | 1/2020 | Roth et al. | |

FOREIGN PATENT DOCUMENTS

| | | |
|---|---|---|
| WO | WO 2006/129301 | 12/2006 |
| WO | WO 2007/010534 | 1/2007 |
| WO | WO 2007/010537 | 1/2007 |
| WO | WO 2007/054935 | 5/2007 |
| WO | WO 2007/074467 | 7/2007 |
| WO | WO 2008/010227 | 1/2008 |
| WO | WO 2010/004536 | 1/2010 |
| WO | WO 2013/168111 | 11/2013 |

OTHER PUBLICATIONS

International Preliminary Report on Patentability dated Dec. 31, 2014 From the International Bureau of WIPO Re. Application No. PCT/IB2013/053721.

International Search Report and the Written Opinion dated Jan. 10, 2014 From the International Searching Authority Re. Application No. PCT/IB2013/053721.

Invitation to Pay Additional Fees dated Nov. 1, 2013 From the International Searching Authority Re. Application No. PCT/IB2013/053721.

Ansto "Imaging Modalities", Workshop Lecture.

Bazanez-Borgert "Basics of SPECT, PET and PET/CT Imaging", Joint Advanced Student School, JASS, St. Peterburg, Russia, Apr. 2-12, 2006, p. 1-13, 2006.

Cherry et al. "Dedicated PET Systems", Physics in Nuclear Medicine, 3rd Edition, p. 346, 2003.

(56) References Cited

OTHER PUBLICATIONS

GE Medical Systems "Millennium VG—CoDe 5. Coincidence Detection for the Millennium VG: H2600SA CoDe Fitted in Factory. H2850SA CoDe Fitted in the Field", GE Medical Systems, Product Datasheet, 4 P., May 1998.
Lewellen "Recent Developments in PET Detector Technology", Physics in Medicine and Biology, 53: R287-R317, Aug. 11, 2008.
Min et al. "A Miniature SPECT Using Multi-Pinhole Collimator With Vertical Septa", 2009 IEEE Nuclear Science Symposium Conference Record (NSS/MIC), Oct. 24-Nov. 1, 2009, M09-86: 3116-3120, 2009.
Peterson et al. "SPECT Detectors: The Anger Camera and Beyond", Physics in Medicine and Biology, 56: R145-R182, Aug. 9, 2011.
Rahmim et al. "PET Versus SPECT: Strengths, Limitations and Challenges", Nuclear Medicine Communications, 29: 193-207, 2008.
Roncali et al. "Application of Silicon Photomultipliers to Positron Emission Tomography", Annals of Biomedical Engineering, 39(4): 1358-1377, Apr. 2011.
Tatischeff et al. "Development of an Anger Camera in Lanthanum Bromide for Gamma-Ray Space Astronomy in the MeV Range", Proccedings of Science, 8th Integral Workshop 'The Restless Gamma-Ray Universe', Dublin, Ireland, Sep. 27-30, 2010, p. 1-6, 2010.
University of Berkely "The Anger Principle & Camera", Introduction to Imaging, University of Berkely, CA, USA, 18 P., Fall 2010.
University of Utah "What is SPECT?", University of Utah, USA, 1 P., Jan. 13, 2014.
Vandenberghe et al. "System Characteristics of SPECT With a Slat Collimated Strip Detector", Physics in Medicine and Biology, 51(2): 391-405, Epub Jan. 4, 2006.
Wells "The Physics Behind CZT", Canadian Association of Nuclear Medicine and Eastern Great Lakes Chapter of the SNM Annual Meeting, University of Ottawa, Heart Institute, 58 P., May 3, 2012.
Wernick et al. "Emission Tomography: The Fundamentals of PET and SPECT", Book, 149 P., 2004.
Wikipedia "Positron Emission Tomography", From Wikipedia, the Free Encyclopedia, p. 1-13, Jan. 6, 2014.
Wikipedia "Positron Emission Tomography", Wikipedia, the Free Encyclopedia, 21 P., Last Modified Mar. 24, 2013.
Communication Pursuant to Article 94(3) EPC dated Jan. 19, 2017 From the European Patent Office Re. Application No. 13788053.0. (5 Pages).
Supplementary European Search Report and the European Search Opinion dated Dec. 11, 2015 From the European Patent Office Re. Application No. 13788053.0.
Communication Concerning the Registration of Amendments Relating to A Transfer (Rules 22 and 85 EPC) dated May 14, 2018 From the European Patent Office Re. Application No. 13788053.0. (2 Pages).
Communication Pursuant to Article 94(3) EPC dated May 3, 2018 From the European Patent Office Re. Application No. 13788053.0. (5 Pages).
Summons to Attend Oral Proceedings Pursuant to Rule 115(1) EPC dated Mar. 15, 2019 From the European Patent Office Re. Application No. 13788053.0. (6 Pages).
Official Action dated Oct. 6, 2020 from the US Patent and Trademark Office Re. U.S. Appl. No. 15/708,166. (78 pages).
Decision to Refuse a European Patent Application dated Dec. 4, 2019 From the European Patent Office Re. Application No. 13788053.0. (20 Pages).
Interview Summary dated Nov. 30, 2020 From the US Patent and Trademark Office Re. U.S. Appl. No. 16/579,894. (3 Pages).
Invitation Pursuant to Rule 63(1) EPC dated Feb. 20, 2020 From the European Patent Office Re. Application No. 19209827.5. (3 Pages).
Official Action dated Oct. 29, 2020 From the US Patent and Trademark Office Re. U.S. Appl. No. 16/579,894. (45 Pages).
Ketchum "New Equipment in Nuclear Medicine, Part 1: Solid-State Detectors", The Journal of Nuclear Medicine, 39(11): 15N, 34N-36N, Nov. 1998.
Restriction Official Action Jul. 13, 2020 from the US Patent and Trademark Office Re. U.S. Appl. No. 15/708,166. (11 pages).
Partial European Search Report and the European Search Opinion dated Jul. 10, 2020 From the European Patent Office Re. Application No. 19209827.5. (12 Pages).
Raghunathan et al. "Matched Collimators for Pixellated Gamma Camera", 2005 IEEE Nuclear Science Symposium Conference Record, XP010895986, Fajardo, Puerto Rico, USA, Oct. 23-29, 2005, p. 2001-2004, Oct. 23, 2005.

\* cited by examiner

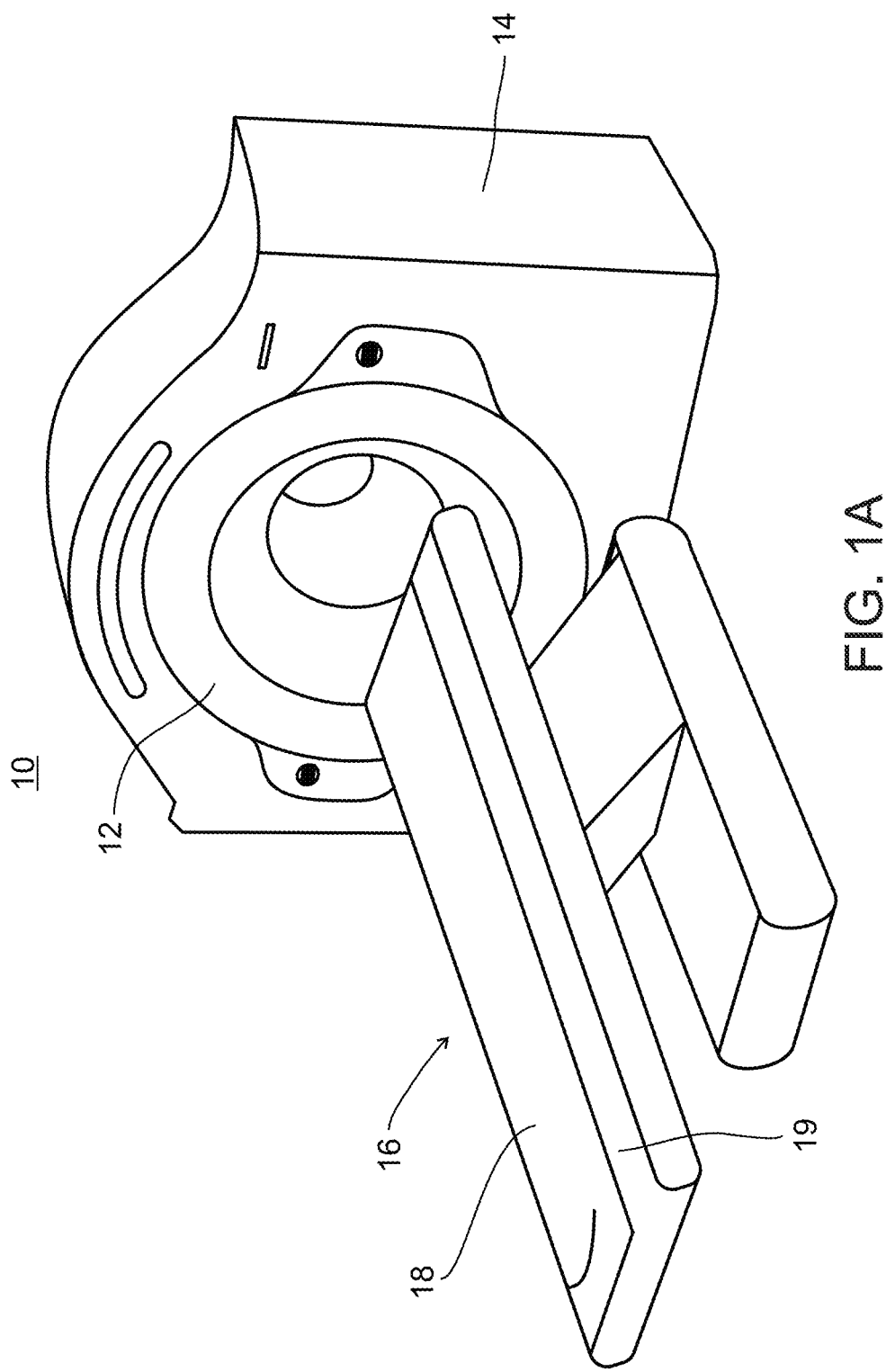

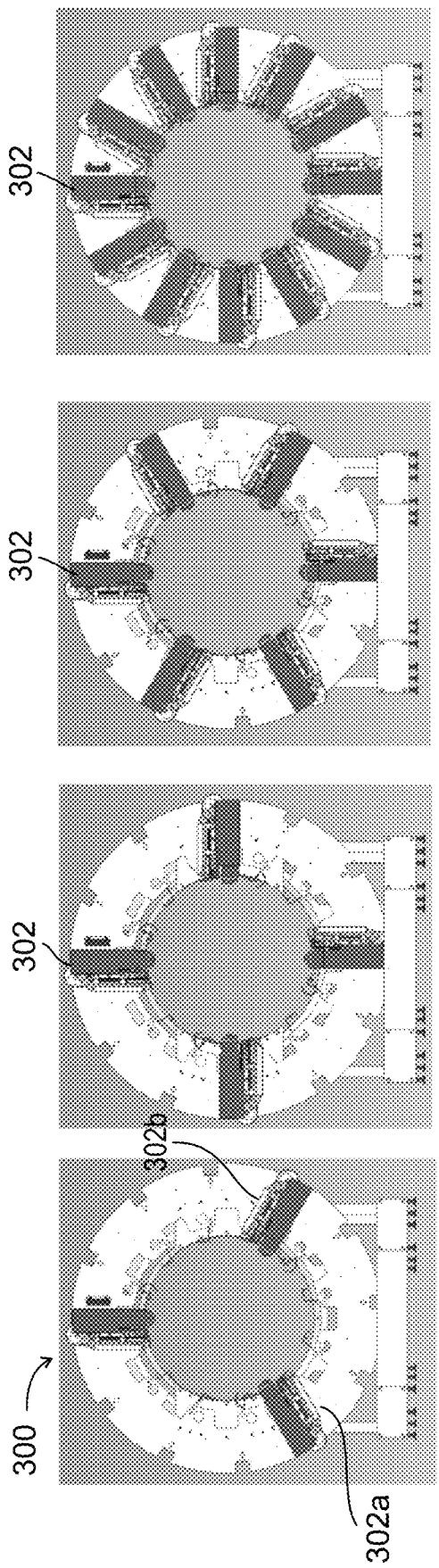

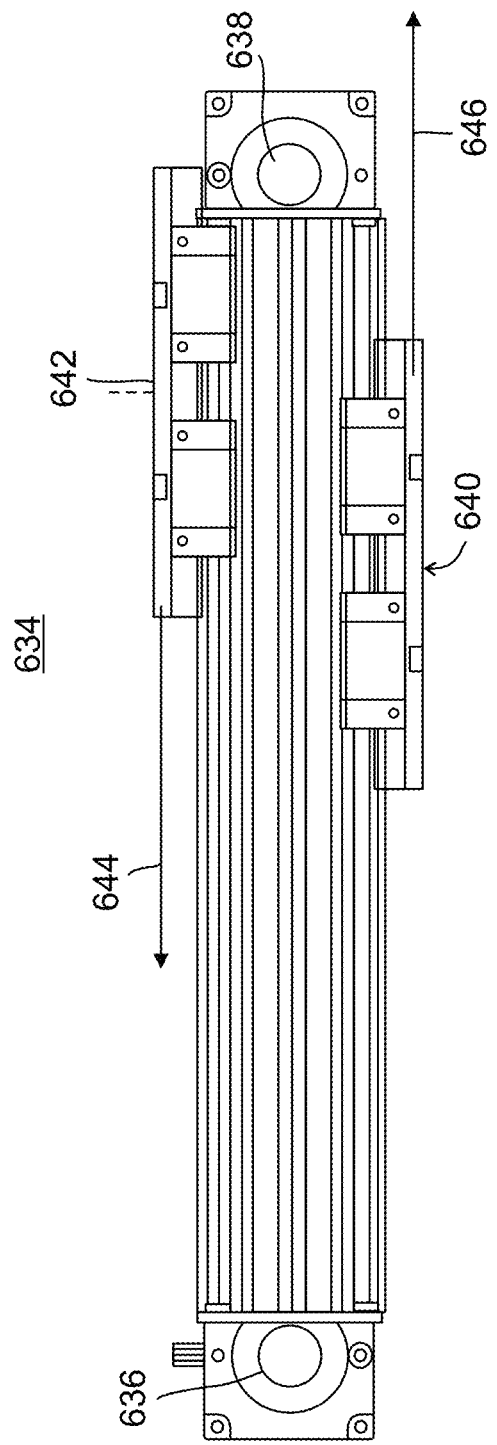

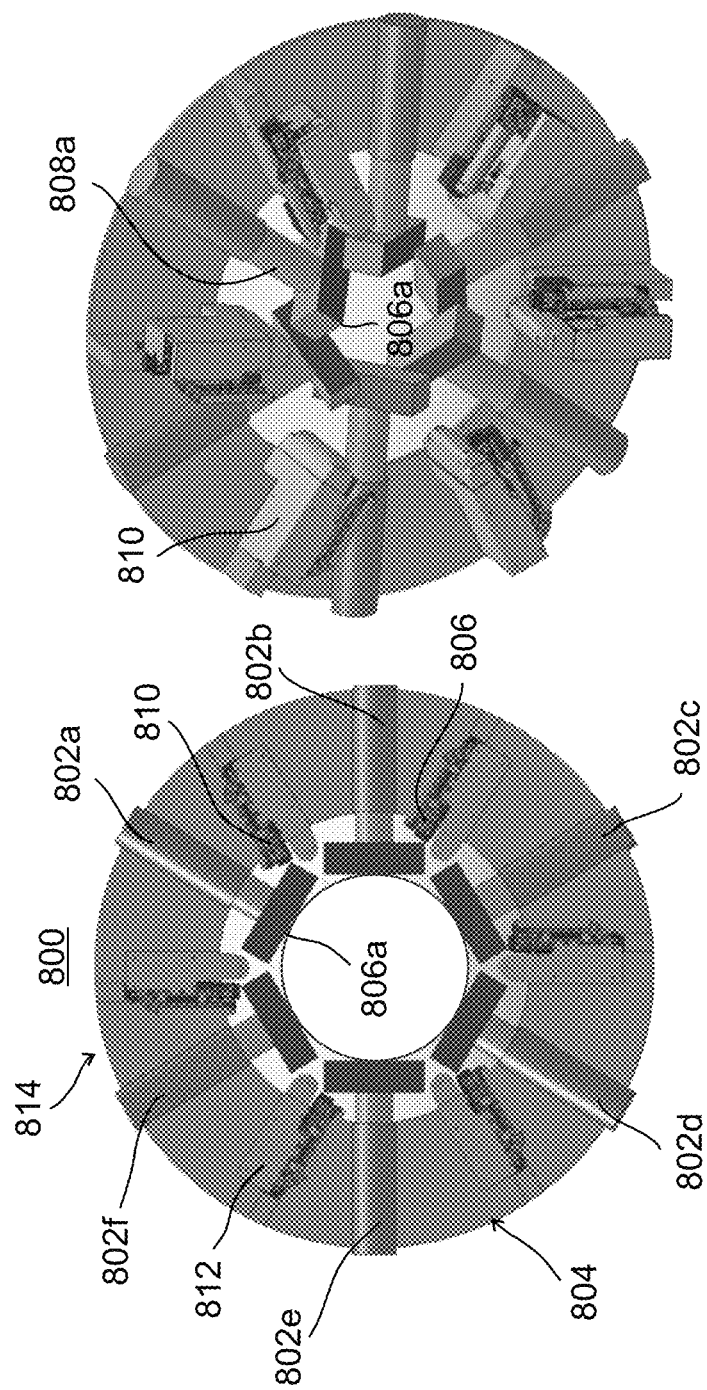

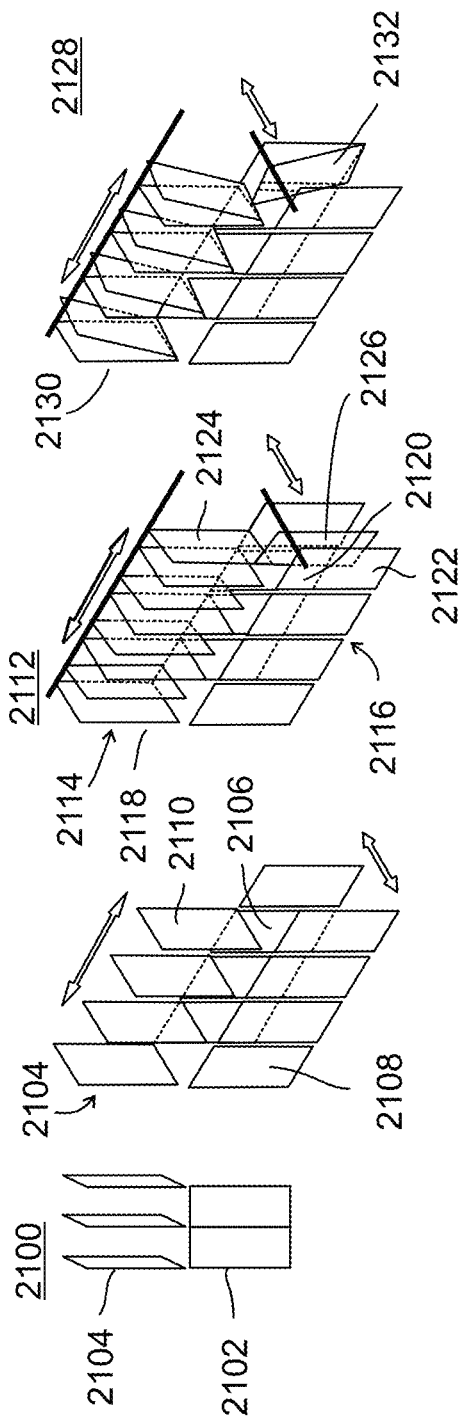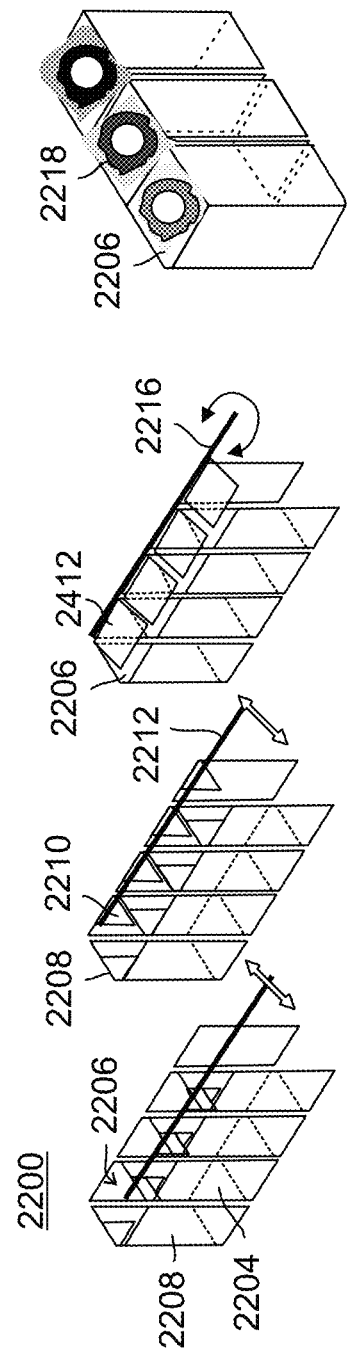

NUCLEAR MEDICINE TOMOGRAPHY SYSTEMS, DETECTORS AND METHODS

CROSS REFERENCE TO RELATED APPLICATIONS

This application is a National Phase of PCT Patent Application No. PCT/IB2013/053721 having International filing date of May 8, 2013, which is a continuation in part of, and claims the benefit of priority under 35 USC 119(e) of U.S. Provisional Patent Application No. 61/644,120 filed on May 8, 2012, U.S. Provisional Patent Application No. 61/646,333 filed on May 13, 2012, and U.S. Provisional Patent Application No. 61/788,394 filed on Mar. 15, 2013. The contents of the above applications are all incorporated by reference as if fully set forth in their entirety.

FIELD OF THE INVENTION

The present invention, in some of its embodiments, relates to apparatus and methods of tomography in the field of nuclear medicine (sometimes referred to herein as "N-M tomography"), and more particularly to N-M tomography systems as a whole, collimated detector configurations for N-M tomography systems, and methods of using N-M tomography systems and detectors. In some embodiments, the invention relates to modular N-M tomography systems and to methods of upgrading existing N-M tomography systems. In some embodiments, the invention relates to dual use SPECT-PET N-M tomography systems and detectors.

BACKGROUND OF THE INVENTION

In General

Systems and methods for medical imaging based on detection of particles emitted by decay of radioactive tracer compounds injected into the bloodstream of a subject have become important diagnostic and research tools, for example, in the fields of cardiology, oncology, and neurology, as well in pre-clinical (e.g., small-animal) studies.

There are two major types of such imaging systems, single photon emission tomography (SPECT) and positron emission tomography (PET). SPECT and PET systems both rely on detection of gamma-ray photons resulting from decay of radio-isotopes, the concentration of which in tissues is indicative of metabolic or other processes within the tissues. For example, tumors are characterized by high metabolic activity and therefore high uptake of the tracer compound, and correspondingly, higher gamma photon emission, while normal tissue exhibits relatively lower metabolic activity and therefore lower uptake of the tracer compound and lower photon emission.

Emission data is obtained at multiple positions around and along the region of interest (ROI) to produce data representing a succession of 2D images or projections which are then converted by use of suitable computerized image reconstruction algorithms into 3D images.

FIG. 1A illustrates schematically major external features of an exemplary N-M tomography system, generally designated at 10. The illustration is broadly representative of the major external features of both conventional SPECT and PET systems, and of some embodiments of the present invention.

System 10 is comprised of a gantry 12 mounted in a stationary frame 14, and a patient carrier 16 including a patient bed arranged to move vertically within the gantry, and axially through the gantry on a track 19. In some installations, patient carrier 16 is stationary, and gantry 12 is axially moveable along the patient carrier.

In conventional SPECT systems, gantry 12 is a ring-like structure arranged to rotate in frame 14 around an axis that runs along the length of the patient carrier 16. (For convenience, this will be referred to herein as the "system axis" or the "patient axis".) The emission detectors in SPECT systems, or "cameras" as they are usually referred to, are typically comprised of a small number, for example, one to four detector units configured as flat plates, sometimes square and sometimes rectangular, extending longitudinally in the direction of the system axis, i.e., into the plane of FIGS. 1A-1B. When two detector units are used, they are often positioned 90 degrees apart on the gantry.

Relative axial movement between the gantry and the patient bed produces the succession of 2D emission projections from which the 3D images are reconstructed. After reconstruction, a "slice" corresponding to an axial position may be selected.

FIG. 1B shows another SPECT system configuration that is particularly useful for cardiac studies of various kinds. The device, generally denoted at 20 employs an adjustable chair 22 as the patient carrier. The detectors are located in a housing 24 moveably attached to a main system housing 26.

The detector housing 24 is generally L-shaped, and the detectors shown by dash lines 28 extend transversely to the housing and generally along the patient axis in an arc around the patient's torso.

A SPECT system configured as illustrated is available commercially at the time of filing of this application from the applicant hereof under the name D-Spect®.

As noted above, the external features of conventional PET systems are similar to those of conventional SPECT systems as illustrated in FIG. 1A. However, the detector heads of a PET system are typically mounted on a non-rotating gantry ring surrounding the patient bed. In typical commercial installations, the gantry ring is fully populated by a large number of closely spaced detectors, each comprised of one or more individual detector elements having small areas, to provide 360 degree coverage around an ROI. PET detectors typically do not include collimators.

Other configurations have also been proposed. U.S. Pat. No. 6,137,109 pertains to SPECT and positron coincidence detection (PET) systems having a small number of detector heads, e.g., two or three, arranged in a polygonal configuration around a gantry. Provision is made for the detector heads to be moved radially toward the patient examination area and tangentially on the gantry to preset the bore size, before an examination is performed.

Cherry, et al., *Physics in Nuclear Medicine*, Third Ed. p. 346, shows a PET system having a gantry ring partially populated by a small number of detector heads arranged in a uniformly or non-uniformly spaced relationship on the ring. In such constructions, to obtain data needed for full image reconstruction, i.e., to provide full 360 degree coverage, the gantry must be rotated to a succession of angular positions. However, a typical gantry installation including detector head positioning mechanisms can weigh hundreds of kilograms, and repositioning the gantry between images can require several minutes. This can be a significant factor in the time required for a scan. Possibly due to the lower efficiency and prolonged acquisition time, fixed-diameter rotating-only partly populated gantries have not been adopted commercially.

A PET installation also generally includes a cyclotron (not shown) which is needed for production of the isotopes used as tracers on site, or at a nearby facility. These isotopes have very short half-lives, i.e. they decay quite rapidly, and often cannot practically be used if produced off-site at a distant facility.

Some Differences Between PET and SPECT Systems and Methods:

SPECT and PET systems are structurally and functionally different in several important respects, and have generally different advantages and limitations.

Basic Physics:

In PET imaging, as a radioactive isotope of the tracer undergoes decay, it emits a positron, an antiparticle of the electron with opposite charge. The emitted positron travels in tissue for a short distance (typically about 1 mm), losing energy as it travels, to a point where it can interact with an electron. The interaction annihilates both the electron and the positron, producing a pair of gamma ray photons having energies of (typically) 511 KeV that move in approximately opposite directions. These high energy photons are detected as a "paired event" (often referred to as "coincidence") by an opposed pair of detectors. Signals from the detectors are collected and temporally correlated to find such pairs and used to generate or reconstruct the 3D images.

For SPECT imaging, radioactive decay of the tracer isotope results in emission of single gamma-ray photons without the intermediate step of positron-electron annihilation. These photons typically have energies in the range of about 40-245 KeV, and are detected as singular events.

Radiotracers:

Isotopes used in PET imaging typically have short half-lives (i.e., exhibit rapid decay). Examples include carbon-11 (approximately 20 min half-life), nitrogen-13 (approximately 10 min), oxygen-15 (approximately 2 min), fluorine-18 (approximately 110 min), or rubidum-82 (approximately 1.27 min). The most commonly used radiotracer in PET imaging is fluorodeoxyglucose (also called FDG or flude-oxyglucose), an analogue of glucose labeled with fluorine-18.

For SPECT imaging, the radioisotopes can be a simple soluble dissolved ion, such as a radioisotope of gallium. Alternatively, and most commonly, a marker radioisotope is attached to another compound which is of interest for its ability to bind in a medically interesting way to tissue under investigation.

Typical tracers used in SPECT imaging include technetium-99m1 (the most commonly used), iodine-123, or iodine 131, or indium-111. These isotopes are heavier than those used in PET and exhibit half-lives measured in hours or even days.

As noted above, cells exhibiting high metabolic activity, for example, cancer cells, typically strongly absorb the radioisotope. In both PET and SPECT imaging, the intensity of the gamma-ray emission provides a measure of concentration in the tissue.

Detectors:

Since both PET and SPECT imaging involve detection of gamma photons, both can utilize detectors that function by the same basic operating principle. The original SPECT detector was the so-called "Anger Camera" (named after its inventor) developed in the 1950's, and while the technology has evolved over time, detectors employing the operating principle of the Anger camera are still used in the majority of commercial SPECT installations.

FIG. 2A shows schematically the construction of an Anger Camera as configured for SPECT imaging, generally designated at 30. Camera 30 is comprised of a detector element 32, usually formed of a thallium-doped sodium iodide (NaI:Tl) crystal optically coupled to an array of photomultipliers (PMT) 34 positioned behind detector element 32. Typically, there are 30-60 or more PMTs depending on the sizes of the detector and the PMTs, arranged in a square or rectangular array.

NaI:Tl crystal 32 functions as a scintillator to convert gamma-ray emissions from a radioactive tracer that has been injected into the blood stream of a subject 36 to visible or near ultraviolet light pulses. PMTs 34 convert the light pulses produced by crystal 32 into electrical output signals which are provided to a computer 38 programmed according to a desired algorithm to reconstruct a succession of 2D slice images into an ultimate 3D image. The 3D image is then stored electronically and/or provided to a visual display unit 40.

Many or all of PMTs 34 simultaneously detect the (presumed) same flash of light to varying degrees, at intensities generally depending on their position relative to the actual emission event. In conventional practice, spatial information about the locations of the gamma photon emissions is obtained by placing a collimator 42 in front of the detection crystal/PMT array. The collimator consists of a thick sheet of lead, typically 1-3 inches thick, with thousands of adjacent holes through it which limits the direction from which the photons can reach crystal 32. The holes are sometimes defined by septa, which block radiation at other directions. In some cases, the collimator is a machined metal plate.

SPECT cameras and especially Anger-type SPECT cameras, use collimators to ensure that photons striking the detectors do so at a relatively narrow range of angles. However, the collimator absorbs a substantial percentage of the incident photons. This limits the sensitivity of the camera system, thereby increasing the time required to obtain sufficient data for a good image. Other methods of image localization, for example, different collimator configurations, and other scintillation detector materials have been proposed but the classic Anger camera still dominates in commercial use. Compton cameras do not use a collimator for detecting the direction, instead scattering of the gamma ray from one set of detectors is detected by a second set of detectors and the path of the gamma ray reconstructed therefrom.

Also known are direct conversion semiconductors that respond directly to gamma-ray photons to produce electrical output signals, thus eliminating the need for the PMTs. Silicon-based devices, sometimes referred to as silicon photomultipliers (or SiPMs) are described in Roncali et al., *Application of Silicon Photomultipliers to Positron Emission Tomography*, Ann Biomed Eng. 2011 April; 39(4): 1358-1377, the content of which is hereby incorporated in its entirety herein. One example of direct conversion detectors are detectors formed of cadmium zinc telluride (CZT) or other materials.

FIG. 2B is a block diagram that illustrates schematically major electronic features of an exemplary conventional PET system, generally designated at 50. Illustrative system 50 includes a detector signal input unit 52 which receives and pre-processes the signal outputs of the detector heads received over a set of signal paths 54, As will be understood, for PET scans, a main function of input unit 54 is to perform coincidence detection of paired signals. As will also be understood, for SPECT imaging, the detector head outputs are processed without the need for coincidence detection.

Output signals from Input Unit 22 are provided to an Image Reconstruction Unit 56, typically a suitably programmed microprocessor-based system, by which the 3D images of the ROIs are created from the detected photon patterns.

The reconstructed images are provided to a display subsystem 58, typically including a user interface, e.g., a keyboard and mouse or other input device (not shown) and a display unit 58.

The operation of the system of FIG. 2B is controlled by a system controller 30, which is typically comprised of a suitably programmed microprocessor, possibly the same one that performs image reconstruction.

As mentioned above, PET imaging relies on coincidence detection of two oppositely traveling photons, and therefore different detector configurations are conventionally used for PET and SPECT imaging. One notable difference is that collimators are not needed for PET imaging since the required spatial resolution results from the coincidence detection process. The absence of a collimator also results in improved sensitivity.

Correspondingly, different image reconstruction algorithms are used for PET and SPECT imaging. One PET image reconstruction algorithm known to those skilled in the art include ML-EM algorithm. Among SPECT image reconstruction algorithms known to those skilled in the art are iterative reconstruction and back projection.

Possibly relevant discussions of PET detector technology may be found in Lewellen, *Recent Developments in PET Detector Technology*, Physics in Medicine and Biology, 53(2008) R-287-317, 11 Aug. 2008. Other discussions possibly relevant to PET technology may be found in Cherry, et al., supra.

A comprehensive survey of SPECT detector technology may be found in *Petersen and Furenlid, SPECT detectors: the Anger Camera and Beyond*, Physics in Medicine and Biology, 56(2011) R-145-182, 9 Aug. 2011 and in Cherry, et al., supra.

The contents of each of these documents are incorporated herein by reference as if fully set forth.

Both conventional PET and SPECT systems are widely used in the fields of oncology and neurology, while SPECT systems are commonly used in cardiology, bone scan imagining, and pre-clinical studies. Another factor relevant to choice of one or the other modality is availability of the isotopes and tracers. Tc-99m is very commonly available for SPECT while F-18 is commonly available for PET.

Each modality is commonly accepted to have certain advantages and limitations. For example, PET systems have historically provided better spatial resolution and faster examination, but are generally much more expensive than SPECT systems, mainly due to the large number of detector elements needed to fully populate the gantry, and the complex coincidence circuitry, but also partially due to the fact that the cyclotron itself is costly and requires high-level technical support.

SPECT systems yield good results for many general purpose applications, including in the fields of cardiology and small-animal pre-clinical imaging. For example, because the gantry rotates during a scan, obtaining full 180 degree coverage may be easier. However, despite technological advances, conventional SPECT systems still provide lower resolution images than PET systems, and consequently, the SPECT images are generally less detailed than PET images due at least in part to scatter and attenuation of the lower energy of the photons. A SPECT scan also typically takes longer than a PET scan, and requires a patient not to move for a longer time, or even to be immobilized and limits the ability to visualize rapid functional changes. Also, the PET tracers' high energy of the photons results in spatial resolution that is less dependent on distance to the ROI.

Further, since SPECT detectors generally require collimators, there is an inherent tradeoff between resolution and sensitivity.

Another limitation of conventional N-M tomography systems, especially PET systems, is that reducing the number of detector heads to avoid the high cost of fully populating the gantry ring as in U.S. Pat. No. 6,137,109 and in Cherry et al. mentioned above sometimes results in reduced spatial resolution and/or longer scan times for scans of small ROIs in systems having a bore size large enough to accommodate obese patients. This limitation is often addressed by the purchase of separate systems for examining patients of large girth and for examining small ROIs.

Yet a further issue concerns the high initial cost of an N-M tomography system. Often, a customer has a limited budget or limited needs which results in purchase of a system having limited capability. For example, a facility faced with budgetary limitations might choose to invest initially in a SPECT or a PET system, but not both, depending on patient volumes and a decision to focus on cardiology or oncology and/or neurology. However, as financial resources or needs change, an entirely new system may need to be purchased. The same thing may happen when technical advances dictate a need for improved capabilities.

Commonly owned technology that may be generally relevant to SPECT imaging, protocols and doses, reconstruction and multi-dimensional imaging and image processing and is optionally used together with some embodiments of the invention may be found in one or more of the following International (PCT) or U.S. published applications or issued U.S. patents:
PCT Published Applications:
WO/2006/129301; WO/2007/010537; WO/2007/010534; WO/2010/004536, WO/2007/010537; WO/2007/010534; WO/2007/010537; WO/2008/010227; WO/2010/004536
Published U.S. Applications:
2004/0015075; 2004/0054248; 2004/0204646; 2007/0194241; 2009/0112086; 2008/0042067; 2008-0230705; 2008-0128626; 2008-0230702; 2009-0201291; 2009-0304582; 2010-0021378; 2010-0142774; 2011-0026685; 2011-0112856; 2012-0106820; 2012-0172699
U.S. Patents
6,173,201; 6,368,331; 6,567,687 7,652,259; 7,705,316; 7,705,316; 7,826,889; 7,872,235; 7,968,851; 7,970,455; 8,000,773; 8,036,731; 8,094,894; 8,111,886; 8,280,124; 8,338,788

SUMMARY OF THE INVENTION

According to an aspect of some embodiments of the invention, there is provided an N-M tomography system having a support for a subject of an examination procedure, a plurality of detector heads, a carrier for the detector heads, and a detector positioning arrangement operable to position the detector heads including rotation thereof to adjacent or radially or circumferentially or axially overlapping positions before and/or during performance of a scan without interference or collision between adjacent detector heads to establish a variable bore size and configuration for the examination.

According to some embodiments, the detector heads include detectors which do not move relative to said heads during acquisition.

According to some embodiments, the system includes a processor which uses data collected by all of said detector heads, for image reconstruction.

According to some embodiments, the detector positioning arrangement is operable to move at least some of the detectors toward and away from the subject carrier to determine the detector bore size.

According to some embodiments, the movement of at least two detector heads is off-center of a central axis of said bore and not towards any common parallel axis of said bore.

According to some embodiments, the movement of at least one detector heads is not along a straight line.

According to some embodiments, the detector positioning arrangement is operable to move at least some of the detectors to a desired rotational orientation relative to respective longitudinal axes thereof.

According to some embodiments, the detector positioning arrangement is operable to tilt at least some of the detector heads to a desired orientation relative to respective longitudinal axes thereof.

According to some embodiments, the detector positioning arrangement is operable to adjust the bore size preliminary to a scan, or in steps at selected axial and/or circumferential positions during a scan, or continuously as the scan proceeds.

According to some embodiments, the detector positioning arrangement is comprised of separate mechanisms to extend and retract and to angularly orient the detector heads.

According to some embodiments, detector-bearing parts of at least some detector heads are tilted by rotation around an axis parallel to a system axis.

According to some embodiments, one of the separate mechanisms for extending and retracting, and angularly orienting the detector heads is associated with each detector head.

According to some embodiments, the detectors heads are all PET detector heads or all SPECT detector heads, or a combination of SPECT and PET detector heads or dual purpose detector heads.

According to some embodiments, the system includes a drive mechanism to rotate the detector heads around the subject carrier to provide 360 degree coverage around the patient carrier with substantially no gaps for a selected bore size.

According to some embodiments, the detector heads are positioned non-uniformly around the detector carrier.

According to some embodiments, the detector positioning arrangement is operable to orient the detector heads angularly to prevent interference between adjacent detector heads when the detector heads are extended to a desired position.

According to some embodiments, the detector carrier is comprised of two or more rings spaced apart from each other by an air gap along a longitudinal axis of the subject carrier with detector heads mounted on each ring.

According to some embodiments, the detector carrier is a single ring with detector heads axially spaced on one side of the single ring, or on opposite sides of the single ring.

According to some embodiments, a plurality of pairs of PET detector heads are spaced circumferentially around the detector head carrier, such that adjacent pairs of PET detector heads are in a spaced relationship on the longitudinal axis of the subject carrier.

According to some embodiments, at least some of the detector heads are circumferentially or laterally moveable along a path near the periphery of the detector carrier.

According to some embodiments, the detector carrier is configured to accommodate a variable number of detector heads.

According to some embodiments, the system includes a controller which controls the detector positioning arrangement to provide movements of the detectors.

According to some embodiments, each detector head is associated with its own detector positioning arrangement.

According to an aspect of some embodiments of the invention, there is provided an N-M tomography system having a plurality of detector heads mounted on a detector carrier that is configured to be populated by a variable number of detector heads and a data processing unit responsive to signal outputs from the population of detector heads to reconstruct a tomographic image from the signals.

According to some embodiments, the detector carrier of an existing system is configured to receive additional detector heads or replacement detector heads having different operational characteristics as part of a system upgrade.

According to some embodiments, the detector carrier includes mounting receptacles to which the additional or replacement detector heads can be operatively attached.

According to some embodiments, the detector heads include signaling mechanisms that indicate the presence of a detector head installed at a particular position on the carrier, and/or the functional characteristics of the installed detector heads.

According to some embodiments, the data processing unit is responsive to the signaling mechanisms.

According to an aspect of some embodiments of the invention, there is provided an N-M tomography system having a plurality of detector heads mounted on a detector carrier, wherein the detector carrier is configured to be populated by detector heads of variable type and/or quality; and a data processing unit responsive to signal outputs from the population of detector heads to reconstruct a tomographic image from the signals.

According to an aspect of some embodiments of the invention, there is provided a method of using an N-M tomography system that includes a support for a subject of a tomography procedure and a detector arrangement comprised of plurality of detector heads that are adjustably positionable on a detector carrier, in which the method involves selecting a bore geometry for the detector array according to a particular region of interest of a subject of a procedure by extending and angularly orienting the detector heads such that adjacent detector heads do not interfere with each other and, scanning the region of interest at successive axial positions relative to a patient carrier.

According to some embodiments, the bore size is selected by one or more of: extending at least some of the detectors toward the subject carrier, rotating at least some of the detectors relative to respective longitudinal axes thereof, tilting at least some of the detectors to a desired off-axis orientation relative to respective longitudinal axes thereof, and moving at least some of the detector heads circumferentially or laterally relative to the periphery of the detector carrier.

According to some embodiments, the selected bore geometry is varied as a scan proceeds.

According to some embodiments, the bore geometry is varied for at least some axial positions.

According to some embodiments, the bore geometry is varied continuously as the scan proceeds at a particular axial position.

According to some embodiments, the detector carrier rotates as the scan proceeds at a particular axial position.

According to an aspect of some embodiments of the invention, there is provided a method of upgrading an existing N-M tomography system that includes a support for a subject of a tomography procedure, a detector arrangement comprised of a plurality of SPECT detector heads and/or PET detector heads, in which one or more additional detector heads of a desired type are installed in receptacles at pre-existing coupling positions on the detector carrier.

According to some embodiments, the method further includes installing adjacent PET detector pairs in receptacles at different axial spacing relative to a subject carrier.

According to some embodiments, the method further includes positioning at least one additional detector carrier in spaced relationship with an existing detector carrier along a longitudinal axis of the subject carrier.

According to some embodiments, an existing detector head is replaced in the field, with a detector head of different quality or type.

According to an aspect of some embodiments of the invention, there is provided a detector unit for a Nuclear Medicine (NM) imaging system having a detector element responsive to gamma ray photons to provide an electrical output signal and a collimator formed of first and second sets of septa extending in two directions that intersect to define an array of collimator cells, in which the septa are moveable to change the geometry of the collimator to increase and decrease the spatial resolution of the detector unit.

According to some embodiments, the septa of the first set are equally spaced from each other and the septa of the second set are equally spaced from each other.

According to some embodiments, the spacing between the septa of the first set is equal to the spacing between the septa of the second set.

According to some embodiments, the spacing between the septa of the first set is unequal to the spacing between the septa of the second set.

According to some embodiments, all the septa of the first and second sets are respectively parallel to each other.

According to some embodiments, all the septa of at least one of the sets are not parallel to each other.

According to some embodiments, the septa of at least one of the sets are moveable to increase the length thereof relative to a surface of the detector element.

According to some embodiments, the septa are moveable to increase or decrease the septa spacing in one and/or both directions relative to a surface of the detector module.

According to some embodiments, the collimator is formed of a plurality of parts spaced from each other in a direction perpendicular to a surface of the detector element, each part being formed of first and second sets of intersecting septa, and the spacing is increased or decreased by moving one or both parts parallel to a surface of the detector element.

According to some embodiments, the collimator is formed of two or three spaced parts.

According to some embodiments, the collimator is formed of three parts perpendicularly spaced relative to the detector element, wherein the septa of the intermediate part are tiltable.

According to some embodiments, at least some the septa in one or both sets are tiltable relative to a surface of the detector element.

According to some embodiments, one end of the collimator cells includes a shutter to adjust the effective size of the area exposed to incoming photons.

According to some embodiments, the shutter is slidable or tiltable or in the form of an iris.

According to some embodiments, the septa are comprised of plates having spaced slots therein, wherein the spacing of the slots in the septa of the first set match the spacing of the septa of the second set, and the spacing of the slots in the septa of the second set match the spacing of the septa of the first set.

According to some embodiments, the septa of the first set are oriented orthogonally to the septa of the second set.

According to some embodiments, the spacing of the septa of the first and second set is non-uniform whereby collimator cells at different locations in the collimator are of different sizes.

According to some embodiments, the collimator cells are square.

According to some embodiments, the collimator cells are rectangular.

According to some embodiments, the septa in the first and/or second sets are of non-uniform thickness.

According to some embodiments, the septa of the first and second sets are of different lengths.

According to some embodiments, the septa of the first and/or second sets are respectively of varying lengths.

According to some embodiments, the detector element is pixilated.

According to some embodiments, the septa are positioned at the borders of each pixel, whereby the collimator cells are aligned with the detector pixels with one pixel per collimator cell.

According to some embodiments, the spacing of the septa of the first and/or second sets is greater than the pixel pitch.

According to some embodiments, the spacing of the septa of the first and/or second sets is smaller than the pixel pitch.

According to some embodiments, the septa of the first and/or second sets are respectively not parallel to each other.

According to some embodiments, the collimator cells are of different sizes and are also of different in size from the size of the detector element pixels.

According to some embodiments, the pixels are arranged in a square matrix or a rectangular matrix.

According to some embodiments, the detector element is a single crystal scintillator and is optically coupled to an array of PMTs.

According to some embodiments, the detector element is an array of direct conversion semiconductor detectors.

According to some embodiments, the detector element is configured as an array of SiPMs.

According to some embodiments, the detector elements are formed of CZT or LYSO.

According to some embodiments, the septa are formed of tungsten.

According to some embodiments, the septa are configured to block less than 50% of 511 Kev radiation passing through at a thickness dimension thereof.

According to an aspect of some embodiments of the invention, there is provided a collimator for attachment to a Nuclear Medicine (NM) imaging system detector element responsive to gamma ray photons to provide an electrical output signal, formed by first and second sets of septa extending in two directions that intersect to define an array of collimator cells, in which the septa are moveable to change the geometry of the collimator to increase and decrease the spatial resolution of the detector unit.

According to an aspect of some embodiments of the invention, there is provided a collimator for attachment to a Nuclear Medicine (NM) imaging system detector element responsive to gamma ray photons to generate an electrical output signal, having a body defining first and second sets of septa extending in two directions, in which a thickness and/or height of the septa in one direction is different from a thickness and/or height in another direction.

According to an aspect of some embodiments of the invention, there is provided a detector unit for a Nuclear Medicine (NM) imaging system having a detector element responsive to gamma ray photons having energy in the range of about 40 KeV to 511 KeV, and a collimator configured to permit use of the detector for both PET and SPECT imaging.

According to some embodiments, the detector element is a scintillator and the detector unit further includes an array of PMTs optically coupled to the detector element to provide electrical output signals.

According to some embodiments, the detector element is a direct conversion element operative to generate an electrical output signal in response to impingement of a gamma ray photon.

According to some embodiments, an electronic signal processor is selectably operable to reconstruct a PET image or a SPECT image or operable to simultaneously reconstruct PET and SPECT images.

According to some embodiments, the circuitry is configured to selectively process a signal from the detector as a single photon event or as a coincidence event.

According to some embodiments, the geometry of the collimator is adjustable to provide high and low spatial resolution.

According to some embodiments, the collimator septa are formed of a material that absorbs PET energy photons with an efficiency of about 50 percent or less of its efficiency of absorbing SPECT photons.

According to some embodiments, the collimator septa are formed of tungsten.

According to an aspect of some embodiments of the invention, there is provided a method of imaging using an N-M tomography system, in which both PET and SPECT data from a target area are simultaneously collected using a single set of detectors.

According to some embodiments, the geometry and/or position of detector heads forming a detector array is adjusted relative to the target area.

According to some embodiments, multiple radiopharmaceutical tracers providing photon emissions having different energies are employed.

According to some embodiments, the detectors are comprised of radiation detector elements and collimators that are adjustable to provide different degrees of spatial resolution.

According to an aspect of some embodiments of the invention, there is provided a method of imaging using an N-M tomography system having a collimated detector unit, in which the configuration of the collimator septa are adjusted to provided a desired degree of spatial resolution; and SPECT imaging is performed using an algorithm that assumes a collection angle and a detection probability map according the adjustment of the collimator configuration, or PET imaging is performed taking account of a detection probability resulting from the adjusted variable septa geometry such that the probability is factored into the image reconstruction.

According to an aspect of some embodiments of the invention, there is provided a method of imaging using an N-M tomography system having a plurality of rotating detector units, in which the rotation of the detector units is adjusted to provide a desired degree of spatial resolution and/or bore size and SPECT imaging is performed using an algorithm that assumes a collection angle and a detection probability map according the adjustment, or PET imaging is performed taking account of a detection probability resulting from the adjustment such that the probability is factored into the image reconstruction.

According to some embodiments, there is provided an N-M tomography system in which the detector heads are formed by a detector element responsive to gamma ray photons to provide an electrical output signal and a collimator having first and second sets of septa extending in two directions that intersect to define an array of collimator cells that septa are moveable to change the geometry of the collimator to increase and decrease the spatial resolution of the detector unit.

According to some embodiments, the detector heads are formed of a detector element response to gamma ray photons having energy in the range of about 40 KeV to 511 KeV and a collimator configured to permit use of the detector for both PET and SPECT imaging.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions.

Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is an exemplary schematic illustration of major external features of a N-M tomography system;

FIGS. 3A-3D illustrate the concept of modularity of a detector head array in an N-M tomography system in the context of an exemplary SPECT or PET system according to some embodiments of the invention;

FIG. 6G illustrates an exemplary mechanism for extending and retracting a detector head according to some embodiments of the invention;

FIGS. 8A-8D illustrate another way to achieve variable bore size shown by way of example for a system operating in a PET mode according to some embodiments of the invention;

FIGS. 21A-21D illustrate resolution adjustment using an arrangement of layered or vertically tandem collimator sub-units or parts, in accordance with some embodiments of the invention;

FIGS. 22A-22D illustrate exemplary (but non-limiting) ways to vary the resolution of collimators according to some embodiments of the invention using adjustable shutters.

Figure 1B:
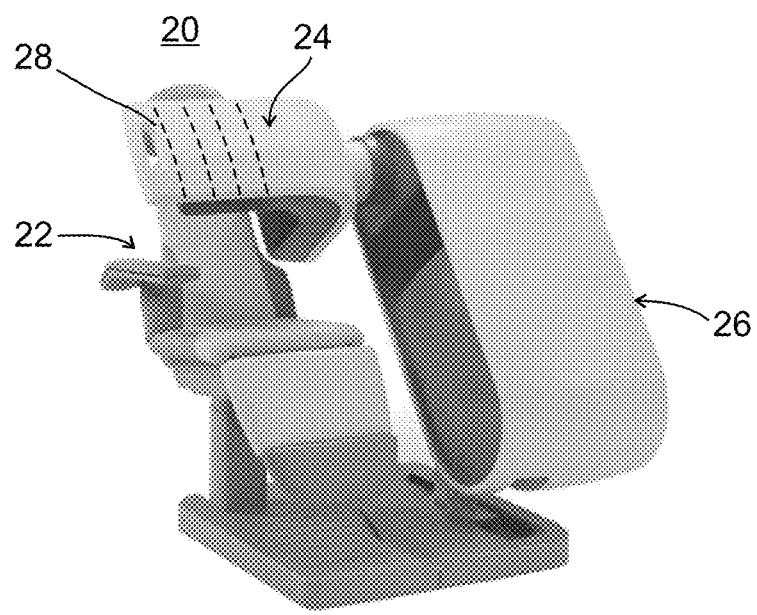
FIG. 1B is an exemplary schematic illustration of major external features of another commercially available SPECT system configuration.

In conjunction with the following detailed description of various aspects of some embodiments of the invention, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

DETAILED DESCRIPTION OF THE INVENTION

Introductory Overview

The present invention, in some of its embodiments, relates to apparatus and methods of tomography in the field of nuclear medicine (sometimes referred to herein as "N-M tomography"), and more particularly to N-M tomography systems as a whole, to detector configurations for N-M tomography systems, and methods of using and/or upgrading such systems and detector arrangements. In some embodiments, the invention also relates to methods of upgrading existing N-M tomography systems and detectors.

In an exemplary embodiment of the invention, there is provided a single system which is easily (e.g., field) upgradable and also capable of dual-mode functionality, e.g., having the capability of selectably operating in either SPECT or PET mode (or both) without materially sacrificing performance in either mode. In an exemplary embodiment of the invention, there is a provided a single detector that can be selectably operable in either a SPECT a PET mode with good resolution and sensitivity.

In an exemplary embodiment of the invention, there is provided a system to be capable of operating simultaneously in both a SPECT and a PET mode.

Some embodiments of the present invention are directed to the issues discussed above, and/or to other aspects of N-M tomography technology.

Aspects of some embodiments of the invention are equally applicable to single function SPECT and PET systems, and to dual function SPECT and PET systems, unless otherwise indicated.

An aspect of some embodiments of N-M tomography systems according to the present invention resides in detector systems comprised of multiple detector heads (for example, 3-18 heads), each head including multiple individual detector elements (for example, 4-10 or more individual detector elements). The detector units are arranged to form a bore defining a space within which the patient as a whole or a part of the patient's body, i.e., an ROI, is examined.

In some of such embodiments, the detector heads are moveable (e.g., during imaging and/or as a set up for an imaging session) relative to the patient carrier and/or to each other and/or to the gantry in various ways allowing adjustment of the size and/or shape of the bore according to the particular ROI without obstruction or collision of adjacent detector heads. In some embodiments, the systems are operable to adjust the size and shape of the bore during a scan.

Optionally, rapid reconfiguration (e.g., faster than 2 hours, 1 hour, 30 minutes, 10 minutes, 5 minutes per detector head) of the detector heads from one position and/or orientation to another for step and shoot operation is facilitated by a light-weight design of the detector heads and/or by counterbalancing.

Optionally, in some embodiments of the invention, the various degrees of freedom can also be implemented in a horizontal system, in which the patient stands or sits, e.g., such that system axis (as well as the main patient axis) is vertical or at an angle to both vertical and perpendicular, and the gantry is relatively horizontal (or at an angle, such as between 20 and 80 degrees to the horizontal.

In some embodiments of the invention, the system provides single-mode functionality, in which case, the detector heads are comprised of only SPECT detectors, or only PET detectors. In some embodiments, the system provides dual-mode functionality, in which case, the detector system includes separate detector heads carrying PET and SPECT detectors, or detector heads that include both PET and SPECT detectors.

Optionally, the detector heads are constructed of detectors that can selectably operate as either PET or SPECT detectors or both SPECT and PET detectors simultaneously. Optionally, such detector heads may include the detector elements, collimators, and/or circuitry that can operate, for example, in single photon detection mode and in coincidence mode. Optionally, timing circuitry is provided in a detector head and coincidence circuitry in a more central location such as a CPU. Alternatively, coincidence circuitry as well is provided in association with a detector head (e.g., module, possibly a head on an arm), optionally the head receiving data on other detections from another head, for example, via a system bus interconnecting heads.

In some embodiments, PET detector heads are T-shaped, or L-shaped (e.g., with wider part facing the bore), and SPECT detector heads are rod or I-shaped. The detector head include elongated stems that serve as the axis for extension/retraction and the detector elements arrayed on the ends of the stems in various polygonal configurations including square or rectangular or triangular, or in circular or arc-shaped configurations, or combination thereof. Optionally, in rest positions, the detector elements extend longitudinally in the direction of the system axis.

Optionally, the detector heads are comprised of a single detector element or a plurality of detector elements forming a pixilated detector.

For convenience, the terms "detector arrangement" or "detector system" or "detector unit" will sometimes be used in reference to multiple and single-detector heads, and to heads that carry SPECT and/or PET detectors, and without distinction as to detector head shape.

An aspect of some embodiments of N-M tomography systems according to the present invention resides in variable-geometry detector systems in which the detector heads are moveable relative to each other and to the gantry in various ways to improve sensitivity and spatial resolution for imaging different ROIs.

An aspect of some embodiments resides in variable-geometry detector systems in which the detector units are non-uniformly arranged on the gantry with (possibly) large gaps between them wherein the adjustability of the detector heads still provides full 360 degree detector coverage possibly without loss (or with improvement) of sensitivity and/or spatial resolution for differently sized and shaped ROIs and/or at different positions along the body of a subject under examination. In some embodiments of the present invention, such configurations possibly reduce the overall number of detectors needed for a given level of spatial resolution and sensitivity, and thus reduce the overall system cost.

The variable geometry features may allow trading off cost and imaging efficiency. The detectors represent a major component in the cost of a system, so being able to vary the bore size and shape according to the size of the patient and/or the location and/or the size of the ROI, may allow generating good images with a smaller number of detectors than would be needed in conventional fixed-geometry systems. However, for a larger ROI or a larger patient, longer imaging times may result from reducing the number of detectors. However, this may allow a majority of studies to be performed fast and/or at a lower cost.

In some embodiments, the detector heads are extended and retracted by a linear extension and retraction mechanism. Optionally, for operation in a PET mode, the detector heads are extended individually or in opposed pairs. Optionally, the opposed pairs are diametrically opposed.

Optionally, multiple detector heads are mounted on and/or moved together along a single arm for in-out and/or lateral motion.

Optionally, at least some of the detector heads are not moved and data for imaging is optionally collected from both moved and unmoved detector heads.

Optionally, a detector head includes electronic circuitry that supports more than one set of separate detector elements. For example, one detector head may include circuitry to support processing of signals from two detector heads which are connected by a data cable. In another example, a detector head is set up to support multiple types of detectors and/or collimators, which may be selectively mounted thereon. Optionally, an RFID code or other machine readable indicator on the detector and/or collimator serve to indicate to the processing circuitry (e.g., in arm or in main machine) which type of detection is available and/or to guide data acquisition, acquisition planning and/or reconstruction, according to the ability of the detector. Optionally, the indicator, or a different storage location includes a table or a set of parameters matching the type of detector and parameters or software for using the detector.

If the size and/or shape of the individual detector heads; (particularly but not exclusively in the case of PET detector heads) do not permit sufficient extension to reduce the bore size to a desired degree without collision or interference between adjacent detector heads, several options are available in accordance with some embodiments of the invention. In some embodiments, only some of the detector heads are extended. For example, every other detector head (i.e., one-half the total number of detector heads) are extended, and the others remain un-extended. Optionally, the un-extended detector heads are not used during the scan. Optionally, the un-extended detector heads and the extended detector heads are used during the scan.

Alternatively, the angular orientation of at least some or all of the detector heads may be varied relative to the axes of extension of the respective detectors to increase the amount that the detectors can be extended without collision. This can be advantageous since allowing a greater range of bore size adjustability can, potentially, better accommodate differently sized and shaped ROIs and ROIs at different locations along the subject's body. Optionally, the angular orientation of the detector heads can be varied either in pairs or individually. Further optionally, one or more of the heads that are connectable to the same arm can be angularly oriented independently or differently than other heads.

According to some embodiments of the invention, at least some of the detector heads are angularly adjustable to a desired orientation in a plane perpendicular to a longitudinal axis of the individual detectors. (This feature is generally referred to below as "rotation" relative to the longitudinal axis.) Typically, but not necessarily, depending on the shape of the detector head, the longitudinal axis corresponds to an axis of extension and retraction.

Optionally, the rotational orientation can be varied from a rest position by up to 90 degrees (or more) such that for some angles and detector dimensions, some or all the detector heads overlap. This may not only facilitate extending at least some of the detectors to obtain a smaller bore size, but may also result in obtaining good 360 degree coverage with a smaller number of detectors.

According to some embodiments of the invention, at least some of the detector heads are angularly adjustable to a desired orientation that is not in a plane perpendicular to a longitudinal axis of the detector heads. (This feature is generally referred to below as "tilting" relative to the longitudinal axis.) Optionally, the desired tilt angle is achieved by rotation around an axis parallel to an axis of elongation of the overall system.

According to some embodiments of the invention, increased reduction in bore size is achieved by axially spacing the detector heads on the gantry. Optionally, the detector heads are axially spaced on one side of a single ring on the gantry. Alternatively, the detector heads are arranged on opposite sides of a single ring. Alternatively the detector heads are arranged on one or two sides of two separately spaced rings comprised in the gantry.

Optionally, for example, in the case of a PET system, adjacent detector head pairs are located at different axial spacing to avoid interference between adjacent detector heads. Extension in combination with one of the orientation options may allow a reduced number of detector heads and/or detector head-pairs in the detector array while still providing good 360 degree coverage. This can significantly reduce the cost of the detector array. In addition, reducing the number of detector pairs allows the gantry to be constructed with open spaces between the detectors along the periphery of the gantry, which facilitates upgradability as described below.

It should also be noted that extension of the detector heads to create a smaller bore size generally has the effect of positioning the detector heads closer to the ROI, consequently, each detector head subtends a larger solid angle around the ROI, and is able to collect more photons emitted from the ROI. The result is that overall system sensitivity may be improved and/or a smaller number and/o size o detectors may be used. Such approaching is optionally used in PET and/or in non-tomographic imaging modes, such as planar imaging.

Positioning the detector heads closer to the ROI may also improve the spatial resolution by decreasing nonlinearity as discussed below.

An aspect of some embodiments of the invention resides in N-M tomography systems in which the detector heads include detector positioning arrangements that are operable to extend and retract and to angularly orient desired combinations of detectors. Optionally, the positioning arrangements are comprised of a first mechanism associated with each detector head to effect extension and retraction, and a separate mechanism to angularly orient the detector heads. Optionally, a single mechanism for extending and retracting and angularly orienting the detector heads is associated with each of the detector heads.

An aspect of some embodiments of the invention resides in N-M tomography systems in which the individual detector heads are translatable, e.g., movable laterally or circumferentially on the gantry, continuously during the scan and/or in steps so that the spacing between the detector heads can be changed. For example, each detector head can be translated 5, 10, 15, or 20 degrees, or a greater or lesser or intermediate amounts from a nominal equally spaced configuration. Optionally, each detector head is movable independently from the others, or jointly with one or some or all of the others. Optionally, in combined PET—SPECT dual function systems, either the PET and SPECT detector heads, or both are circumferentially movable. Optionally, the PET and SPECT detectors are located at (and/or attached to the gantry at) different axial positions, for example, on one or both sides of a single rotor disc, or on separate rotor discs, optionally to provide mechanical clearance.

As used herein, the term "circumferential movement" refers to rotation of the gantry ring or rings, and also includes movement of the detector heads on the gantry. Likewise, circumferential movement includes translational movement of each of the detector heads individually, i.e., independently, or in groups within the ring, and/or movement of an entire ring relative to other rings.

Translation of the detector heads can be advantageous in various situations. For example, on a gantry having a small number of detector heads e.g., as purchased by a customer with limited resources, there may be large gaps between detector heads. Similarly, when the system is constructed of a segmented gantry (optionally with each segment including more than one detector head) the segments can be moved radially outward so the bore is expandable when necessary (e.g. to accommodate an obese patient). In either case, the gaps between the heads may degrade data acquisition. Circumferential movement effectively shifts the gaps and allows capturing data from the gaps to complete the missing views.

Optionally, according to some embodiments, the gaps can be closed by rotation of the gantry or alternatively by relative rotation among the detectors, for example, by translating the detector heads circumferentially on a single-ring gantry, of in the case of a multiple-ring gantry, by rotating one or more of the rings relative to the others, to complete the full set of angles between pairs of detectors. Effectively, the bore is expanded radially and gaps are created, the circumferential motion (if any) allows the gaps to be filled. Optionally, the system is constructed so translation can occur during a scan or in steps for step and shoot operation.

In some embodiments, gaps (e.g., between 1 and 30 degrees, for example, between 2 and 10 or 20 degrees) in an axial direction and/or in a circumferential direction are tolerated. Optionally, reconstruction weights (e.g., for sensitivity) certain directions according to the presence and/or size of gaps therein.

A feature of some embodiments of N-M tomography systems according to the present invention resides in a gantry that is slidable and/or rotatable laterally, to capture an image from a "body slice" which is orthogonal or not orthogonal to the main body-axis, and/or move along the body of the patient, for example to capture "slice by slice".

In an exemplary embodiment of the invention, a controller can selectively move one or more of the detector heads alone, independently, in groups and/or separately but optionally in synchrony with other detector heads.

An aspect of some embodiments of N-M tomography systems according to the present invention resides in matching the detector bore to the ROI by making the extension and/or angular orientation adjustable while the scan is being performed.

A related aspect of some embodiments resides in detector arrays per se having detectors that are extendable and/or angularly adjustable during a scan.

By way of summary, adjustment of the size and shape of the bore as well as improved sensitivity and resolution is achieved by optionally providing one or more of the degrees of freedom listed below.

For the gantry (e.g., in either SPECT or PET operation unless otherwise noted):

(a) The gantry can be a full circle, or a partial circle.

(b) The gantry can include one ring or multiple rings. The planes defined by the rings may be parallel to each other, or non-parallel. In a PET mode, the gantry may be rotated circumferentially, either continuously during generation of data for a slice, or in steps (referred to herein as "step and shoot" operation).

(c) The gantry may move vertically relative to the system axis, or can be tilted (e.g., using a motor and/or a gear) to one or more non-vertical orientations, and/or to one or more orientations that are non-orthogonal to the system axis to obtain views that can overcome attenuation or other obstruction or scatter, or to obtain additional complementary information that helps stabilize the image reconstruction process.

(d) Optimally, some or all the adjustments mentioned above can be performed manually. Optionally or alternatively these adjustments can be motorized and controlled by the system controller.

For the Detector Heads (e.g., in SPECT or PET operation):

(e) Some or all the heads can move in and out, radially, i.e. extend and retract, to increase or decrease the bore size. The extension/retraction can be the same for all the detector heads, or may be different depending on the location of a particular ROI in the body;

(f) The detector heads can move laterally relative to each other and/or to the gantry. The movement of the detector heads can be linear or along a non-straight-line path, for example, a curved or piece-wise linear paths elected to avoid or reduce collisions between adjacent detector heads;

(g) The detector heads can be rotated around an axis which is substantially orthogonal to the system axis, e.g., around the axis of extension/retraction;

(h) The detector heads can be tilted in one or more planes relative to the axis of extension/retraction. Tilting can be effected by rotating the head around an axis which is substantially parallel to the system axis, or by rotation around an axis which is non-parallel to the system axis;

(i) The system controller can be programmed to move the detector heads in a manner that prevents collision during movement, for example, by calculating dynamics to predict a collision and slow down movement as needed. Optionally or alternatively, sensors are provide (e.g., IR or ultrasonic proximity sensors) at the sides of the detectors, to detect imminent collisions.

An aspect of some embodiments of the invention resides in PET systems or in dual purpose systems operating in a PET mode, in which the detector heads are arranged around less than the full 360 degrees of the gantry and in which the gantry rotates, e.g., as in typical SPECT systems. Optionally, the scan is performed at a succession of axial slices.

Optionally, the rotation is continuous at each axial position. Alternatively, the gantry rotates in steps of less than 360 degrees and is temporarily stationary at each step. Optionally the size of the steps is based on the size of the gaps between the detectors. Optionally, the continuous or stepwise gantry rotation during a PET scan is repeated for each of a succession of axial slice positions. Optionally, in embodiments in which PET detectors are mounted on more than one axially spaced rotor on the gantry, the rotational speed of each rotor may be the same or different.

An aspect of some embodiments of N-M tomography systems according to the present invention resides in the detector arrays being positionable at one or more desired distances from the patient's body. Optionally, positioning may be done before or during a scan, optionally continuously, or between axial slices.

An aspect of some embodiments of the present invention resides in N-M tomography systems that include proximity detection capability to prevent contact between the detector array and the body of the patient. Optionally, proximity detection capability is provided by contact sensors, or by acoustic sensors, or by IR sensors, or by optical sensors.

An aspect of some embodiments of the present invention resides in N-M tomography systems that include proximity detection capability to prevent contact between a detector and an adjacent detector and/or to prevent contact and/or pinching of body parts between detectors (e.g., if patient moves his harm into harm's way, for example, proximity detection capability is provided by contact sensors, or by acoustic sensors, or by IR sensors, or by optical sensors.

In an exemplary embodiment of the invention, contact sensors are acceptable, because detector motion uses low forces, detectors are low-weight and/or covered with a soft layer and/or detectors can be quickly stopped (e.g., using brakes or suitable motor/actuator action).

An aspect of some embodiments of N-M tomography systems according to the present invention resides in detector arrays that are allowed to make contact with the patient's body, but with such a low contact force and/or velocity that injury to the patent does not occur. In some such embodiments, the detector arrays are counterbalanced on the linear actuator arms so the force needed to extend the detector arrays is acceptably small (e.g., using a stepper motor which generates up to 3 Kg force only). Optionally, the extension force is small enough that the patient can move the detector array away from his or her body. Optionally, the actuator allows such back driving, for example, using gears which can be back driven or by a linear actuator which can be overridden by patient applied force. Further, because of the small mass of the individual detector heads, impact with the body is optionally small. Also because of the low mass, the velocity is easily reduced before impact.

An aspect of some embodiments of the present invention resides in N-M tomography systems having modular and/or scalable detector arrays. A related aspect of some embodiments of the invention resides in modular or scalable detector arrays per se.

Modularity can allow initial assembly of N-M tomography systems having detector arrays with a desired number of individual detector heads according to a particular customer's initial needs, and facilitates subsequent upgrading. This can give a customer the option, both at the time the system is acquired, and/or at the time of an upgrade, to trade off cost versus quality, for example, as described herein. For example, three, four, six, eight, twelve, or an intermediate or greater number of detector heads can be provided initially, and more added later as needs and/or financial resources of the customer change. Optionally or alternatively, detectors can be replaced with different and/or better detectors.

In an exemplary embodiment of the invention, either by way of identifying data provided by the added detector heads, or by information provided manually to the system controller, the software knows what detectors have been installed, and the information can be used in the course of data acquisition and/or image reconstruction.

In some embodiments, the detector arrays as originally assembled are for single-mode SPECT or PET systems. Optionally, the detector arrays as originally assembled include both SPECT and PET detector heads allowing dual-mode system functionality.

Optionally, as part of an upgrade, existing detectors may be replaced by better or improved detectors, for example, having faster circuitry, larger detection area, and/or better energy and/or spatial resolution. Optionally, detectors can be added and/or replaced when upgrading either a single-mode or a dual-mode system to improve the functionality of the system.

Optionally, an upgrade can convert a single-mode system into a dual-mode system. Optionally, x-ray CT capability may also be provided in new and/or upgraded single and dual-mode systems.

Optionally, features contributing to modularity according to some embodiments include, without limitation, one or more of the following:
  (a) The gantry which carries the detector array is rotatably mounted in the initially assembled system, whether it is single-mode (SPECT or PET) or dual mode;
  (b) Connection of the detectors to the coincidence processing electronics is through a rotatable coupling arrangement;
  (c) The image reconstruction electronics and/or the coincidence processing electronics are adapted to recognize the number and type (SPECT or PET) of detector heads in the detector array, either automatically, or by programming at the time of assembly or upgrading of an existing system;
  (d) The detector heads provide identification as to connection and/or type for auto-recognition by the electronics sub-systems;
  (e) A rotary drive system is easily installed as part of an upgrade;
  (f) The electronic sub-systems are modular to facilitate converting a single-mode system into a dual mode system.

Various ways to implement some of the above-described features will be apparent to those skilled in the art, especially in view of the exemplary methods of implementations are described below.

In some embodiments of the invention, PET detectors are used, i.e., that are used for detecting high energy photon pairs travelling in opposite directions by identifying the locations in which 2 photons hit 2 detectors simultaneously (up to photon travel time and detection time), thus enabling identifying the orientation from which the photon has been emitted at a much finer precision. For example, such embodiments allow detection along a line with a width of about 4-6 mm, taking into account the distance of the positron traveling until annihilated (about 2-4 mm), and the pixel width in each detector (for example 2-3 mm).

Optionally, however, in some embodiments, acquisition of PET (high energy) photons can be done without coincidence detection using "SPECT methodology" (detecting each photon separately) by providing a thick collimators and detector heads capable of detecting typical PET and SPECT photons.

Furthermore, coincidence detection circuitry can optionally include time-of-flight analysis circuitry to determine where along the estimated emission line the positron was emitted, for example at a longitudinal resolution of about 1-5 cm, for example 2-3 cm. For example, an optional system clock can be shared by the detector heads. As an optional alternative, processing is in central location which pre-calibrates travel time from each detector of signals.

In some embodiments, the electronic circuitry connected to some or all of the detector heads includes one or more of the following optional capabilities:
  (a) Photon characterization by energy level (for example, within all the range between 40 Kev and 511 Kev or more);
  (b) Detection time with resolution sufficient to determine coincidence with photon detection in another detectors,
  (c) Detection time with resolution sufficient to determine time of flight for obtaining high longitudinal resolution along the detected coincidence line;
  (d) Detection of count rate in case of high flux of photons, for example when a high intensity radiation source is activated such as X-ray source;
  (e) Optionally, the electronics include multiple separate channels that allow independent amplification and front-end processing for each detector or small group of detectors (e.g., 1-5 detectors) and/or a small number of pixels (e.g., between 10 and 1000, for example 100 pixels). A potential advantage is that malfunction of one or more pixels or detectors and/or blinding of one or more pixels or detectors by a "hot spot" (high intensity source) desirably will not prevent other detectors from properly function and detect photons emitted from other regions, for example as described in US patent publication 2008-0230702-A1.
  (f) Optionally, the processing channels may also be modular, for example, being field replaceable and/or include their own housings.

An aspect of some embodiments of the invention pertains to a method of using N-M tomography systems including detector arrays having some or all the adjustability features described herein that involves preparing the patient in the normal manner, setting up the system for an examination by adjusting the bore size and/or shape, then axially scanning the region of interest, optionally axially. Optionally the adjustment is achieved by extending at least some of the detector heads and, if necessary, angularly orienting at least some of the detector heads in the detector array according to the size and/or shape of the ROI and/or the axial position of the ROI along the body of the patient. Optionally, the angular orientation is adjusted by rotation of at least parts of some of the detector heads. Optionally, the angular orientation is adjusted by tilting at least some of the detector heads.

Optionally the adjustments can be made during scanning, for example in response to change in body cross-section, imaging mode.

Optionally, the method applies to single and dual-purpose systems.

In a system providing dual-mode functionality, the method further optionally includes selectable operating the system in a SPECT or in a PET mode.

In some embodiments, the method involves providing a plurality of additional detector units that include built-in mechanisms for extension/retraction and angular orientation. Optionally, the additional detector units are mounted in alternating relationship with the existing detector units on the gantry. Optionally, if the pre-existing system does not provide automatic detection of the number and type of detector units, the method further includes adding automatic detection or programming the emission detector subsystem according to the number and type of detector units in the upgraded system.

Optionally, the position adjusting arrangement provided is operable to extend and retract the detector units, and/or to alter the angular orientation of the detector units by rotation and/or tilting at least some of the detector units. Optionally, the position adjusting arrangement includes separate extension/retraction and angular orientation mechanisms. Optionally, each added detector unit includes its own mechanisms for extension and retraction, and/or for rotating or tilting.

Optionally, the detector units of the upgraded system are mounted so that some of them in the upgraded detector array are axially spaced from others, but on one side of a gantry ring. Optionally, some of the detector units in the upgraded detector array are mounted on opposite sides of a detector carrier ring. Optionally some of the detector units in the upgraded system are mounted on axially offset detector carrier rings.

It should be understood, that upgradability as described herein is feasible in systems that do not contain scalable detector arrays, but the benefits may be attenuated since the entire preexisting detector array may need to be replaced, and the emission processing and/or image reconstruction sub-systems may have to be reprogrammed or even replaced.

An aspect of some embodiments of the present invention resides in N-M tomography systems in which the detector units are capable of responding to photons in a range of energies including both PET and SPECT ranges. Optionally, the detectors and associated emission data processing systems are selectably responsive to PET or SPECT photons, or, simultaneously responsive to PET and SPECT photons to generate or reconstruct visual 3D images of regions of interest (ROI) of a patient being examined.

In such embodiments, and also in other exemplary embodiments described herein, parts of the data processing systems are optionally contained within or mounted on the detector units.

In exemplary embodiments described herein, the radioactive emission detector is comprised of a scintillator optically coupled to an array of photomultipliers. Alternatively, the detector is a direct conversion semiconductor array, or a silicon photomultiplier (SiPM) (see: Roncali et al., supra).

Optionally, in the exemplary embodiments described herein, the emission detector elements are pixilated. Alternatively, at least some detector elements are non-pixilated.

Optionally, in the exemplary embodiments described herein, the emission detector elements are formed of a known material including, but not limited to, Lutetium Oxyothosilicate (LSO), Lutetium Yittrium Oxyothosilicate (LYSO), Cadmium Zinc Telluride (CZT), Cadmium Telluride (CdTe), Cesium Telluride (CsTe), Cesium Iodide (CsI), or of any other suitable and desired material presently known or hereafter discovered or created.

An aspect of some embodiments of the present invention resides in detector units including collimators that permit selectable operation in either a PET or SPECT mode, optionally without physical reconfiguration thereof. Optionally, the detector units are operable to simultaneously produce PET and SPECT images.

Optionally, in such embodiments and in other exemplary embodiments described herein, the collimators are formed of a material that effectively blocks photons having energy in the range used for SPECT imaging, but is relatively transparent to photons having energy in the range used for PET imaging. Optionally, the material forming the collimators blocks no more than about 50% of incident PET photons. Optionally, the collimators are formed of Tungsten, or Tungsten Carbide or Lead or Gold or depleted Uranium or a combination of these materials. Optionally, the amount of blocking for PET detection is selected so that at angles or directions where a higher sensitivity is desired, there is less blocking.

An aspect of some embodiments of the present invention resides in detector units including collimators having adjustable geometry that permits changing the spatial resolution of the detectors. Optionally, such adjustment permits the detector units to be selectably operated either as PET or SPECT detectors, or optionally to simultaneously produce PET and SPECT images.

Optionally, according to some embodiments, the collimator geometry can be varied in one or more of the following ways:
  a) increasing the length of the septa forming the collimator cells (the term "length" referring to the height of the collimator perpendicular to the plane of the detector module);
  b) increasing the spacing of the septa (i.e., the pitch) in one and/or both directions relative to a surface of the detector element (optionally, by removing one or more septa);
  c) tilting some of the septa in one and/or both directions relative to a surface of the plane of the detector element;
  d) increasing or decreasing the pitch of the septa (i.e. the distance between adjacent septa walls) in one and or both directions relative to a surface of the detector element: the pitch can be decreased, for example, by forming the collimator of two or more relatively moveable parts parallel to the plane of the detector element;
  e) forming the collimator with a shutter to adjust the effective size of the area exposed to incoming photons: optionally the shutter is slidable or tiltable or in the form of an iris.

Optionally, the detector element has a planar surface relative to which the septa are moveable.

In some embodiments, these modifications are carried out while the collimator is attached to the detector. In some embodiments, the collimator is removed, modified and reattached. In some embodiments, the reconfiguration is provided in a laboratory and/or during manufacture. Optionally, the collimator-detector pair is pre-configured at multiple collimator states.

In an exemplary embodiment of the invention, a pressure clamp and/or a screw clamp and/or a locking rod (through the septa) mechanism are used to hold septa in place relative to a body of the collimator.

An aspect of some embodiments of the present invention resides in detector units including collimators that have a first set of leaves in a first arrangement and a second set of leaves arranged to intersect with the first set. Optionally, an average height perpendicular to a detector surface and/or an average thickness of leaves of the first and second sets are different. This may result in different viewing angles in different direction and/or different amount of PET sensitivity in different directions.

An aspect of some embodiments of the present invention resides in a method of imaging comprising using an N-M tomography system to collect PET and/or SPECT from a ROI using a single set of detectors. Optionally, PET or SPECT data are collected simultaneously. Optionally, when PET and SPECT data are collected simultaneously, PET and SPECT images are generated simultaneously using separate electronic subsystems.

In an exemplary embodiment of the invention, the amount of axial, circumferential and/or radial overlap at least 5%, 10%, 20%, 30% or intermediate or greater percentage of the dimension and/or detector area of the detector head. Optionally or alternatively, the overlap is less than 90%, 80%, 50%, 40% or smaller or intermediate percentages thereof.

Rotation around an axis of a detector can be for example, 10, 30, 40, 70 or smaller or intermediate degrees.

Optional Features of Some Embodiments of the Invention:

The discussion below concerns further optional features of some embodiments of the invention according to the aspects of the invention discussed above. It should be understood that one or more of these features may be combined with any embodiments of the detector units and methods described herein above and/or below and/or provided with other systems, unless otherwise clearly stated:

a. Multiple detector heads arranged around a gantry which are moveable relative to the patient carrier and/or to each other and/or to the gantry to create a variable-geometry bore over a wide range of sizes without obstruction or collision of adjacent detector heads.

b. Adjustability of the bore geometry during a scan, optionally between steps of a step-and-shoot scan, or between axial positioning of the gantry for acquisition of data for a succession of axial slices. Optionally, adjustment may be performed both between step-and-shoot positions and between axial positions, or "on the fly" according to a pre-set program for a specific patient scan, both during scan or in a sequences scan scenario.

c. Rapid reconfiguration of detector geometry facilitated by light-weight design of the detector heads and/or by counterbalancing the detector units.

d. Variable bore geometry implemented in conventionally configured systems (with the patient lying on a horizontal carrier) and also systems, in which the patient stands or sits such that system axis (as well as the main patient axis) is vertical, and the gantry is relatively horizontal.

e. PET detector heads that are T-shaped, or L-shaped, and SPECT detector heads that are rod or I-shaped.

f. Detector heads including elongated stems that serve as an axis for extension/retraction with the detector elements arrayed on the ends of the stems in various polygonal configurations including square or rectangular or triangular, or in circular or arc-shaped configurations, or combination thereof. Optionally, in rest positions, the detector elements extend longitudinally in the direction of the system axis.

g. Detector heads that are comprised of a single detector element or of a plurality of detector elements, for example, pixilated detectors. For convenience, the terms "detector arrangement" or "detector system" will sometimes be used in reference to multiple and single-detector heads, and to heads that carry SPECT and/or PET detectors, and without distinction as to detector head shape.

h. Variable-geometry detector systems in which the detector units are non-uniformly arranged on a gantry with large gaps between them wherein the adjustability of the detector heads still provides full 360 degree detector coverage without loss of sensitivity and spatial resolution for differently sized and shaped ROIs and at different positions along the body of a subject under examination. In some embodiments of the present invention, such configurations possibly reduce the overall number of detectors needed for a given level of spatial resolution and sensitivity, and potentially reduce the overall system cost.

i. Detector heads that are extended and retracted by linear actuators. Optionally, in a PET mode, detector heads that are extended individually or in opposed pairs. Optionally, the opposed pairs are diametrically opposed. Optionally, multiple detector heads are mounted on and/or moved together along a single arm for in-out and/or lateral motion.

j. Detector arrays in which some of the detector heads are not moved and data for imaging is optionally collected from both moved and unmoved detector heads.

k. Detector heads that include electronic circuitry that supports more than one set of separate detector elements, e.g., of different types and/or geometric location.

l. Variable geometry detector arrays in which the detector heads; (particularly but not exclusively in the case of PET detector heads) are moveable in ways that permit bores small enough for efficient imaging of relatively small organs such as the brain, the throat or an extremity, without collision or interference between adjacent detector heads. Options include:

(i) making only some of the detector heads, for example, every other detector head extensible, (with the un-extended detector heads optionally used or are not used during the scan, (ii) making the angular orientation of at least some of the detector heads adjustable relative to the axes of extension of the respective detectors to increase the amount that the detectors can be extended without collision. Optionally, the angular orientation of the detector heads can be varied either in pairs or individually. Further optionally, one or more heads that are connectable to the same arm can be angularly oriented independently or differently than other heads, (iii) making at least some of the detector heads rotatable or tiltable. It should also be noted that extension of the detector heads to create a smaller bore size has the effect of positioning the detector heads closer to the ROI, consequently, each detector head subtends a larger solid angle around the ROI, and is able to collect more photons emitted from the ROI, The result is that overall system sensitivity may be improved.

m. making detector heads translatable, i.e., movable circumferentially on the gantry, continuously during the scan or in steps so that the spacing between the detector heads can be changed. For example, each detector head can be translated 5, 10, 15, or 20 degrees, or a greater or lesser or intermediate amounts from a nominal equally spaced configuration. Optionally, each detector head is movable independently from the others, or jointly with one or some or all of the others. Optionally, in combined PET-SPECT dual function systems, either the PET and SPECT detector heads, or both are circumferentially movable. Optionally, the detectors heads can be moved in one or more straight line segments or along a curve.

n. Locating translatable PET and SPECT detectors at different axial positions, for example, on one or both sides of a single rotor disc, or on separate rotor discs to provide mechanical clearance.

o. Configuring the detector arrays so that gaps between then can be effectively closed by rotation of the gantry. (As used herein, the term "circumferential movement" also refers to rotation of the gantry ring or rings, continuously and/or in steps) as well as by translating the detector heads circumferentially on the gantry to complete the full set of angles between adjacent detector heads. Optionally, the system is constructed so translation can occur during a scan or in circumferential steps (for step and shoot operation) or between axial positions.

p. Making the gantry slidable and/or rotatable laterally, to capture an image from a "body slice" which is orthogonal or not orthogonal to the main body-axis, and/or move along the body of the patient, for example to capture "slice by slice".

q. Providing for selective movement of one or more the detector heads alone, independently, in groups and/or separately but in synchrony with other detector heads.

r. The gantry can be fully circular, or a partial circle, as well as other shapes.

s. The planes defined by multiple gantry rings may be parallel to each other, or non-parallel.

t. The gantry may move vertically relative to the system axis, or can be tilted to one or more non-vertical orientations (e.g., be mounted on a motorized axle), and/or to one or more orientations that are non-orthogonal to the system axis to obtain views that can overcome attenuation or other obstruction or scatter, or to obtain additional complementary information that helps stabilize the image reconstruction process.

u. Gantry rotation is continuous at each axial position for both PET and SPECT imaging. Alternatively, the gantry rotates in steps, the size of which is optionally based on the size of the gaps between the detectors. Optionally, in embodiments in which PET detectors are mounted on more than one axially spaced rotor on the gantry, the rotational speed of each rotor may be the same or different.

v. Providing proximity and/or side detection capability to prevent contact between the detector array and the body of the patient. Optionally, proximity detection capability is provided by contact sensors, or by acoustic sensors, or by IR sensors, or by optical sensors, or in any other suitable and desired manner.

w. Permitting the detector heads to make contact with the patient's body, but with such a low contact force and/or velocity that injury to the patent does not occur.

x. Counterbalancing the detector heads so the force needed to extend the detector heads is acceptably and safely small. Optionally, the force is small enough so that a patient can easily resist the force or can move the detector array away from his or her body by hand if necessary. The optional small effective mass of the individual detector heads, allows the velocity to be easily reduced before impact.

y. The detector head counterbalancing mechanisms include adaptive motion feedback capability for safety control and acquisition continuation if the detector head is touched or pushed back, for example, by the patient.

z. Configuring the system so that the detector arrays are modular or scalable.

aa. Either by way of identifying data provided by the detector heads added as part of an upgrade, or by information provided manually to the system controller, the system software is made aware of what detectors have been installed, and the information can be used in the course of data acquisition and image reconstruction.

bb. The gantry which carries the detector array may be rotatably mounted in the initially assembled system, whether it is single-mode (SPECT or PET) or dual mode;

cc. The detector heads are connected to the processing electronics through a rotatable coupling arrangement;

dd. The gantry is configured so it requires only minimum disassembly for upgrading, including to facilitate installation of a rotary drive system, thereby helping to permit on-site upgrading;

ee. The electronic sub-systems are modular to facilitate converting a single-mode system to a dual mode system.

ff. Coincidence detection circuitry for PET imaging can include time-of-flight analysis circuitry to determine where along the estimated emission line the positron was emitted, for example at a longitudinal resolution of about 1-5 cm, for example 2-3 cm. For example, an optional system clock can be shared by the detector heads. As an optional alternative, processing is in central location which pre-calibrates travel time from each detector of signals.

gg. The electronic circuitry connected to some or all of the detector heads includes one or more of the following optional capabilities:
  (i) Photon characterization by energy level (for example, within all the range between 40 Kev and 511 Kev);
  (ii) Detection time resolution sufficient to determine coincidence with photon detection in another detector,
  (iii) Detection time resolution sufficient to determine time of flight for obtaining high longitudinal resolution along the detected coincidence line,
  (iv) Detection of count rate in case of high flux of photons, for example when a high intensity radiation source is activated such as X-ray source.

hh. The electronics include multiple separate channels that allow independent amplification and front-end processing for each detector or small group of detectors and/or a small number of pixels (e.g., between 10 and 1000, for example 100), such that any malfunction of one or more pixels or detectors and any blinding of one or more pixels or detectors by a "hot spot" (high intensity source) do not prevent other detectors from properly function and detect photons emitted from other regions. Optionally, the processing channels may also be modular.

An aspect of some embodiments of the invention resides pertains to a method of using an N-M tomography system including detector arrays optionally having some or all the adjustability features described herein. In some embodiments, both PET and SPECT imaging can be performed, either sequentially or simultaneously. Optionally, the method involves preparing the patient in the normal manner, setting up the system for an examination by adjusting the bore size and/or shape, then scanning the ROI. Optionally the adjustment is achieved by extending at least some of the detector heads and, if necessary, angularly orienting at least some of the detector heads in the detector array according to the size and/or shape of the ROI and/or the axial position of the ROI along the body of the patient.

In a system providing CT capability, the latter modality may optionally also be employed as part of a unified examination.

An aspect of some embodiments of N-M tomography systems according to the present invention resides in use of collimated detectors for PET imaging, with image reconstruction software that compensates for reduced off-axis sensitivity resulting from photon absorption by the collimator septa, for example, by weighting of photon counts according to their direction of impact.

Exemplary System Features:

Referring again to FIG. 1A, in some exemplary embodiments of the invention, gantry 12 is mounted so that in addition to conventional functionality by which it moves along the length of patient carrier 16 (or vice versa) to capture emission data from a succession of "slices" orthogonal to the length of the patient's body, (i.e., the body-axis), it is optionally also constructed so it can slide transversely (e.g., on a rail) or tilt relative to the body-axis (e.g., the rail is mounted on an axle or an actuator is provided at either end to raise/lower a side of the rail), to capture emission data in planes that are not orthogonal to the body-axis.

This capability can be advantageous, for example, if it is desired to acquire photons from viewing angles with less attenuation and scatter due to bones (e.g. taking different viewing angles to overcome attenuation and scatter by the ribs, etc), or to improve uniformity, quality and stability of the image reconstruction process by providing to the reconstruction algorithm information from additional viewing angles.

Modularity and Upgrade:

An aspect of some embodiments of the invention is modularity of the detector arrays. Referring now to FIGS. 3A-3D, several implications of this are described in the context of a detector array 300 for a SPECT system according to some embodiments of the invention. In the illustrated context, it should be understood that modularity applies to the design of detector array 300 such that it may be assembled from a desired number of individual detector heads 302a, 302b, etc. according to the specification of the customer.

FIG. 3A illustrates a detector array 300 with three individual detector heads 30 (two being a practical lower limit in conventional systems). FIGS. 3B-3D respectively illustrate systems employing detector arrays having four, six and 12 individual detector heads 302. Exemplary configurations of detector heads embodying features of the present invention are described below.

FIGS. 3A-3D also illustrate the trade-off resulting when increasing numbers of detector heads are provided: performance is increased in terms spatial resolution and/or sensitivity and/or speed of image data acquisition for a range of ROI sizes and shapes and longitudinal (axial) locations along the body of the subject of an examination, but at potentially significant increased cost for the detector heads.

Figure 4B:
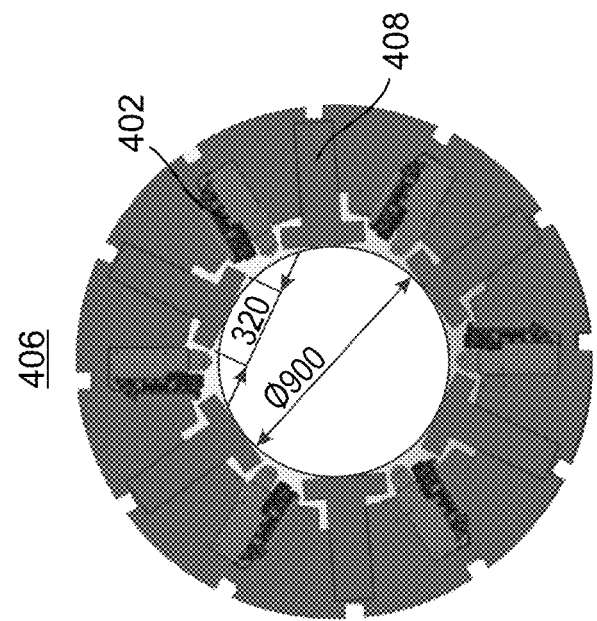
FIGS. 4A and 4B illustrate upgrading an as-built single-mode PET or SPECT system into a dual-mode SPECT+PET system according to some embodiments of the invention.
Figure 4A:
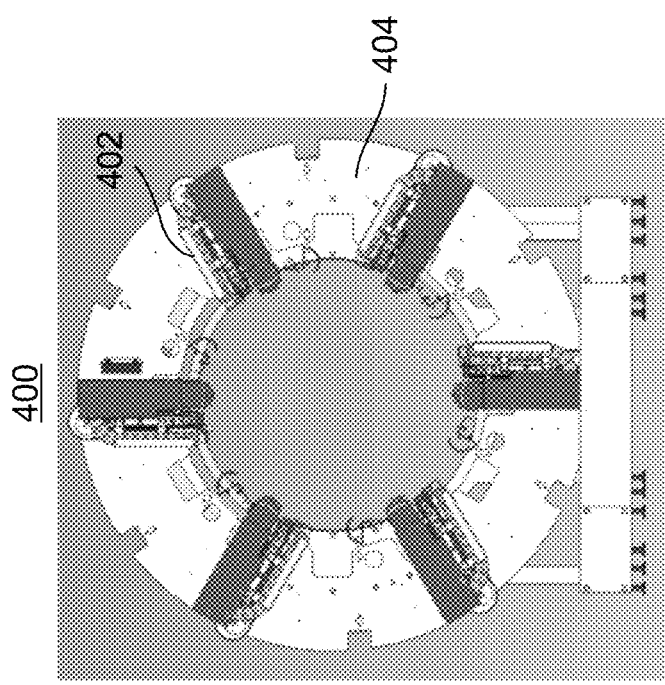

Another implication of modularity is illustrated in FIGS. 4A and 4B: a system can initially be assembled with a detector array 400 providing single-mode functionality (here illustrated as SPECT functionality) and can conveniently be upgraded into a dual-mode system that provides both SPECT and PET functionality.

Thus, FIG. 4A shows an as-built detector array 400 for a SPECT system having six detector heads 402 with considerable open space 404 between the individual detectors. FIG. 4B shows a detector array 406, for example, after an upgrade of detector array 400. Here, six PET detector heads 408 have been installed in alternating relationship with SPECT detector heads 402. As will be understood, FIG. 4B can represent an as-built configuration or an upgraded detector array comprised only of 12 PET detectors 408 or only of 12 SPECT detectors 402.

Figure 5:
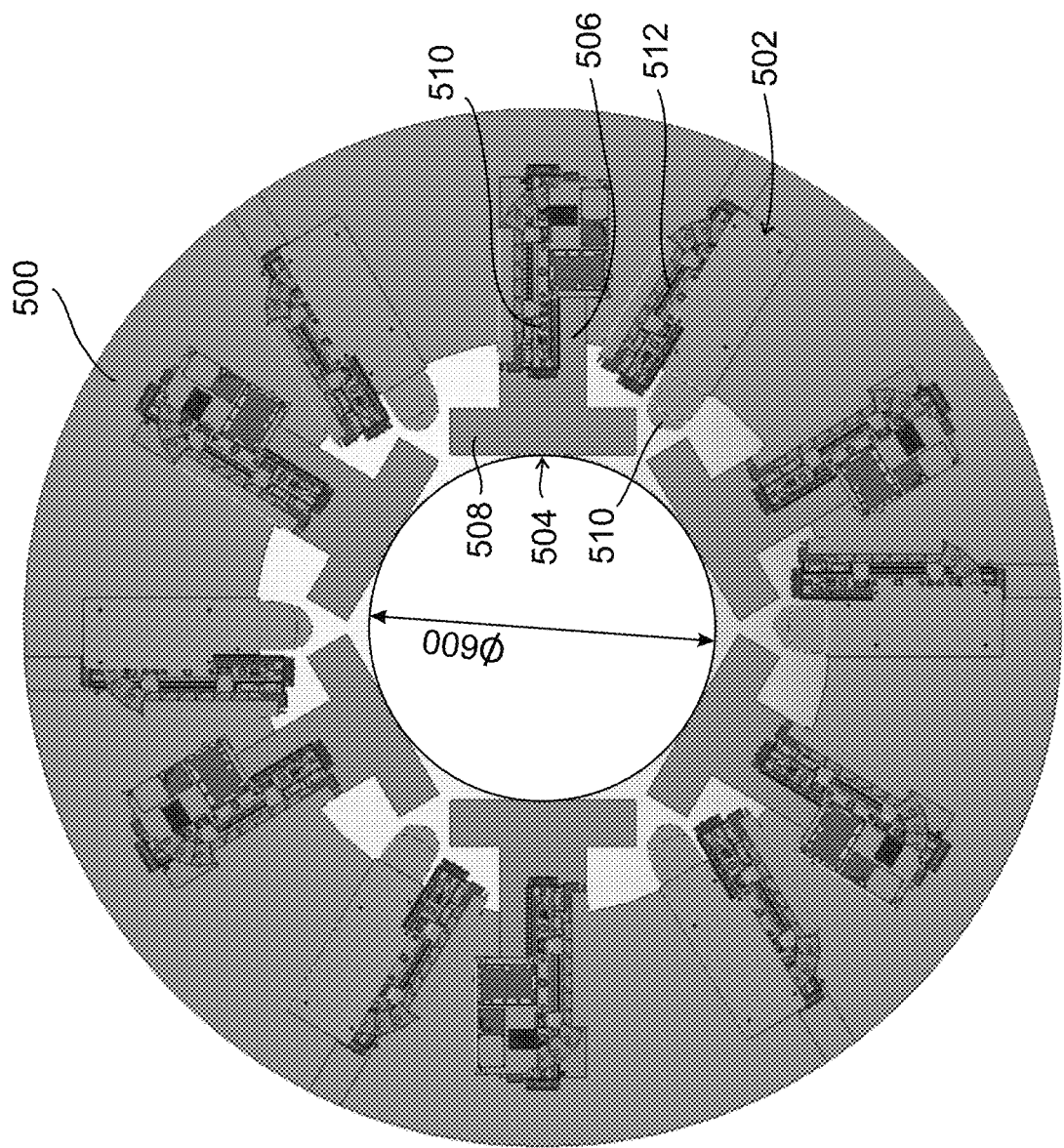
FIG. 5 is an enlarged version of FIG. 4B according to some embodiments of the invention.

In an exemplary embodiment of the invention, a modular attachable/detachable component includes a housing suitable for exterior viewing/environment, for example, with suitable paint and/or markings. In an exemplary embodiment of the invention, the attachment of the component to the rest of the system includes separate electrical, data and mechanical connectors. For example, plug-socket connectors may be used for power and data and a mechanical interlock used for mechanical connection. In some embodiments, the component will interlock to a movable part of the system. In an exemplary embodiment of the invention, two interlocks are used; one interlock providing alignment between the detector and the system (or gantry), for example, a plurality of pins matching recesses and/or other geometries and a second interlock provides interference to prevent retraction, for example, using one or more screws, bolts or a locking rod. Optionally, a separate element (from the alignment geometry), such as a rectangular rod, is used to convey forces between the system and a removable detector Basic Detector Head Configurations FIG. 5 shows exemplary details of SPECT and PET detector heads according to some embodiments of the invention mounted on one side of a single gantry 500. SPECT detector heads 502 are shown as rod or I-shaped with arcuate, e.g., approximately cylindrical photon-collecting surfaces 510 extending into the plane of the figure. PET detector heads 504 are shown as T-shaped with a stem portion 506 extending radially toward the system axis at the center of gantry 500 and a detector-carrying portion 508 oriented tangentially to the periphery of the bore.

It will be appreciated that other external configurations are also within the scope of some embodiments. For example, both the SPECT and PET detector heads can be L-shaped or otherwise have different shapes. Optionally, different detectors with different abilities have different shapes and/or sizes.

Optionally and preferably, in some embodiments, the detector-carrying portions 508 of PET detector heads 504 are configured as plates that extend in the direction of the system axis, i.e., into the plane of the figure. This can be advantageous, for example in that it allows a desired degree of overlap between slices as the emission data is being collected, or wider slice width, to perform faster body scan (in the case of multiple-slice scan).

The large detector head configuration for the PET detector heads 504 can be advantageous because for optimal and uniform PET image reconstruction, pairs of PET detectors sometimes need to cover as much as possible of the whole 360 degrees of possible photon emission from each location in the ROI, and/or with a sufficient axial extent. Having large detector surfaces for the PET detector heads may minimizes gaps in which coincidence lines are not covered and/or otherwise increase sensitivity, and may avoid reduced uniformity and/or sensitivity.

SPECT detectors, on the other hand can acquire 180 degrees around the ROI in several positions at different times, so, in some embodiments they can be narrower and move to obtain the necessary viewing angles. In an exemplary embodiment of the invention, care is taken, however, that the PET detectors are not so large that they obscure the view of the SPECT detectors when only the latter are in use.

Figure 2A:
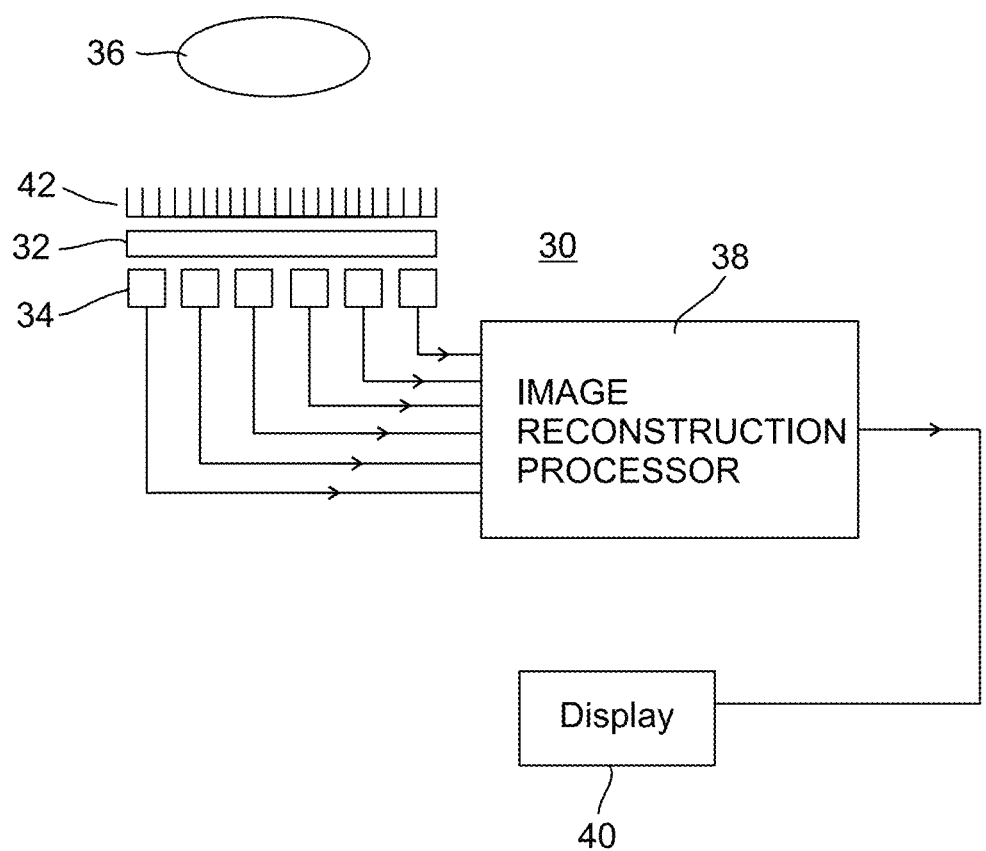
FIG. 2A is an exemplary schematic illustration of the layout of a detector unit, for example, an Anger camera for a SPECT system.
Figure 2B:
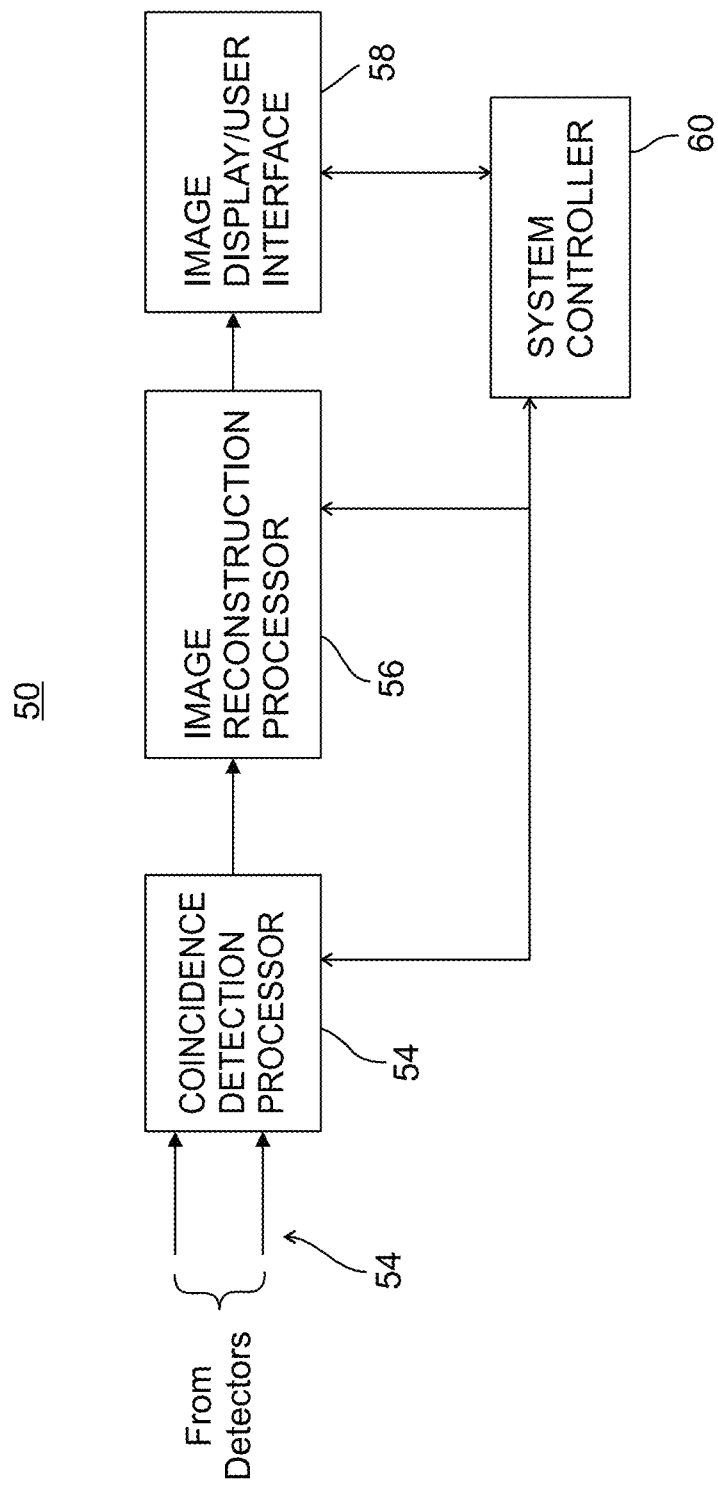
FIG. 2B is an exemplary schematic illustration of an electronic subsystem for z PET system.

As described herein, the dynamically variable geometry of the detector heads according to some embodiments of the invention facilitates optimizing or near-optimizing the size and/or shape of both the PET and SPECT detectors. Potentially contributing to optimization is the placement of the detectors on one or more gantry rings which can move and operate independently as discussed herein. In an exemplary embodiment of the invention, the system controller 30 (see FIGS. 2A-2B) may be programmed to plan and/or control the motion of the detectors heads according to a desired (e.g., optimal) data collection from the desired ROI, while optionally preventing adjacent detector heads from colliding and/or obscuring each other's field of view.

In some exemplary embodiments, the SPECT detector heads include detectors (e.g., radiation sensitive elements thereof) that cover overall about 1-40 cm, or 1-20 cm, for example, about 2-8 cm along the circumferential dimension, i.e., along the gantry, for example about 4 cm. In the axial direction, i.e., in the direction of the system axis, the SPECT detectors optionally cover overall about 10-40 cm, for example about 12-32 cm, or 15-30 cm, or 16-28 cm, or about 16 cm, or about 20 cm, or about 24 cm, or about 28 cm or intermediate sizes.

In some exemplary embodiments, collimators extend radially, i.e. toward the patient's body a distance of a few cm (e.g. 1-20 cm, 1-4 cm, for example about 2-3 cm).

In some embodiments, the SPECT detectors (with the collimator) of each such detector head are rotatable, for example, around an axis parallel to the system axis. In some embodiments, the overall space required to enable such free rotation of the head along the circumferential dimension can be about 6-15 cm wide, for example 7-12 cm, for example about 10 cm.

In an example, the PET detector heads include detectors that cover overall about 2-50 cm along the circumferential dimension, for example about 2-40 cm, or 2-35 cm, or 3-30 cm, or 5-28 cm, or 10-28 cm, or 15-25 cm, or 20-25 cm, and cover overall about 2-35 cm along the axial dimension, for example about 2-30 cm, or 2-25 cm, or 2.5-20 cm, or 2.5-17 cm, or 2.5-15 cm, or 3-10 cm, or 3-9 cm, or 3-8 cm, or 3-5 cm, for example less than 15 cm, and optionally less than 10 cm, or for example about 5 to 9 cm, or for example 7 to 8 cm.

Dynamically Variable Bore Geometry:

Conventionally, in both PET and SPECT systems, the bore size is not adjustable, and therefore the sensitivity and/or spatial resolution vary according to the particular ROI and body location. The conventional solution has been to provide a bore adequate to accommodate a full-body scan and accept degradation in performance when a smaller bore would have been preferable for a particular ROI as explained below. Another conventional solution has been special small-bore systems for brain or neck scans.

According to some embodiments of the present invention, N-M tomography systems are provided with a dynamically variable-geometry bore. Several ways to achieve this are implemented by providing the degrees of freedom for gantry configurations and/or detector head extension/retraction and/or angular orientation. In an exemplary embodiment of the invention, these are pre-selectable, i.e., before performance of a scan, and/or adjustable during the scan, either continuously or in steps.

FIG. 4B shows a 12 detector head system with alternating PET and SPECT detector heads on a circular gantry in which the heads are all in a fully retracted configuration providing a maximum bore size for both PET and SPECT operation. Optionally, a non-one to one relationship of the number of PET and SPECT is possible.

In the configuration shown in FIG. 5, all the PET detector heads 504 have been extended to provide a reduced bore size for PET operation. Alternatively only SPECT detectors are extended. It may be seen that FIG. 5 represents approximately the maximum extension possible without collision of adjacent heads to the illustrated size and configuration of the PET detector heads illustrated.

FIG. 5 also shows exemplary extension/retraction mechanisms 510 and 512 respectively for the PET and SPECT detector heads, described more fully below.

FIGS. 6A-6D, illustrate spatial resolution improvement that can be achieved when the bore size is increased or decreased to take account of the particular ROI and body location. The example shows a SPECT only system with 12 detector heads 602 on one side of a single-ring circular gentry 600, but the same benefits can be achieved in PET only systems, and in systems capable of both SPECT and PET operation.

Figure 6A:
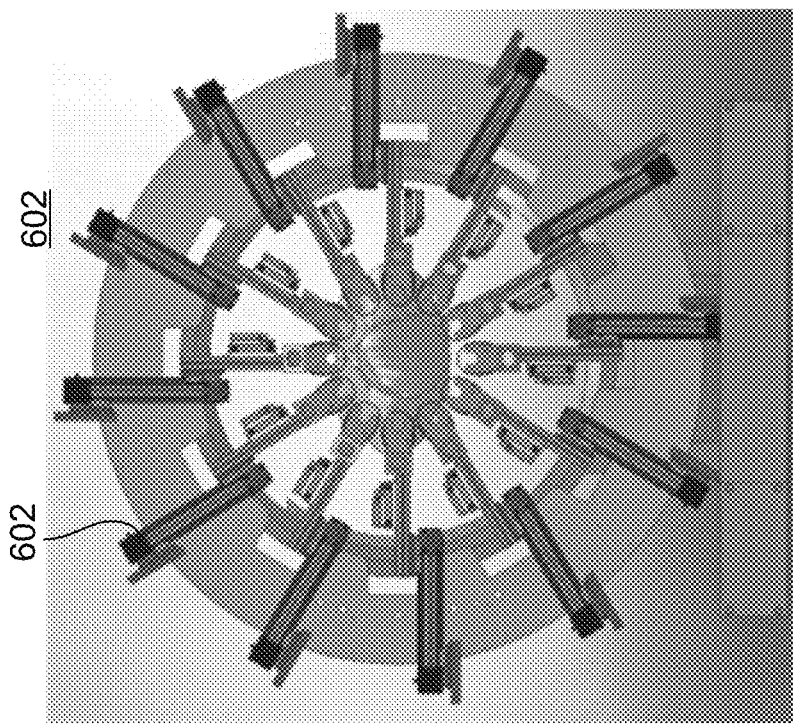
FIGS. 6A and 6B illustrate the concept of variable bore size according to some embodiments of the invention.
Figure 6B:
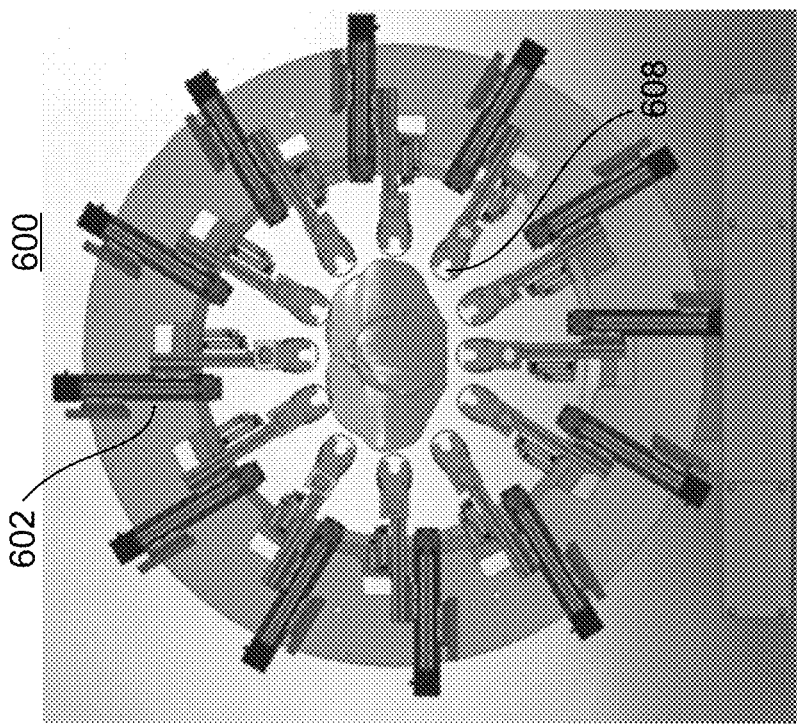

FIG. 6A shows detector heads 602 in a retracted configuration to provide a large bore, for example, a conventional 90 cm. bore, for performing a full body scan. FIG. 6B illustrates detector heads 602 fully extended to provide a small bore, for example, 20 cm., as it would be used, for example, when performing a brain scan or a scan of the neck.

It should be appreciated that the cross-section of an ROI will generally not be circular, particularly in the case of a body scan, so the possibility non-uniform resolution and/or sensitivity may exist. According to some embodiments of the invention, if desired (or for other reasons) this can be alleviated in some instances by varying the orientation of the detection surfaces dynamically during the scan. For the arrangement illustrated in FIGS. 6A and 6B, this can be achieved by rotating the detector-carrying portions 604 of detector heads 602 around an axis parallel to the system axis during a scan. The detectors can optionally be rotated individually or together. Since such rotation can effectively fill gaps between adjacent detector heads, it may also allow obtaining good sensitivity and resolution with a smaller number of detectors, and thereby result in a less costly system.

It should also be noted that in an exemplary embodiment of the invention, only the detector element bearing parts of the detector heads need to be moved. Since these are not heavy, rapid dynamic changes in orientation are practical.

Figure 6C:
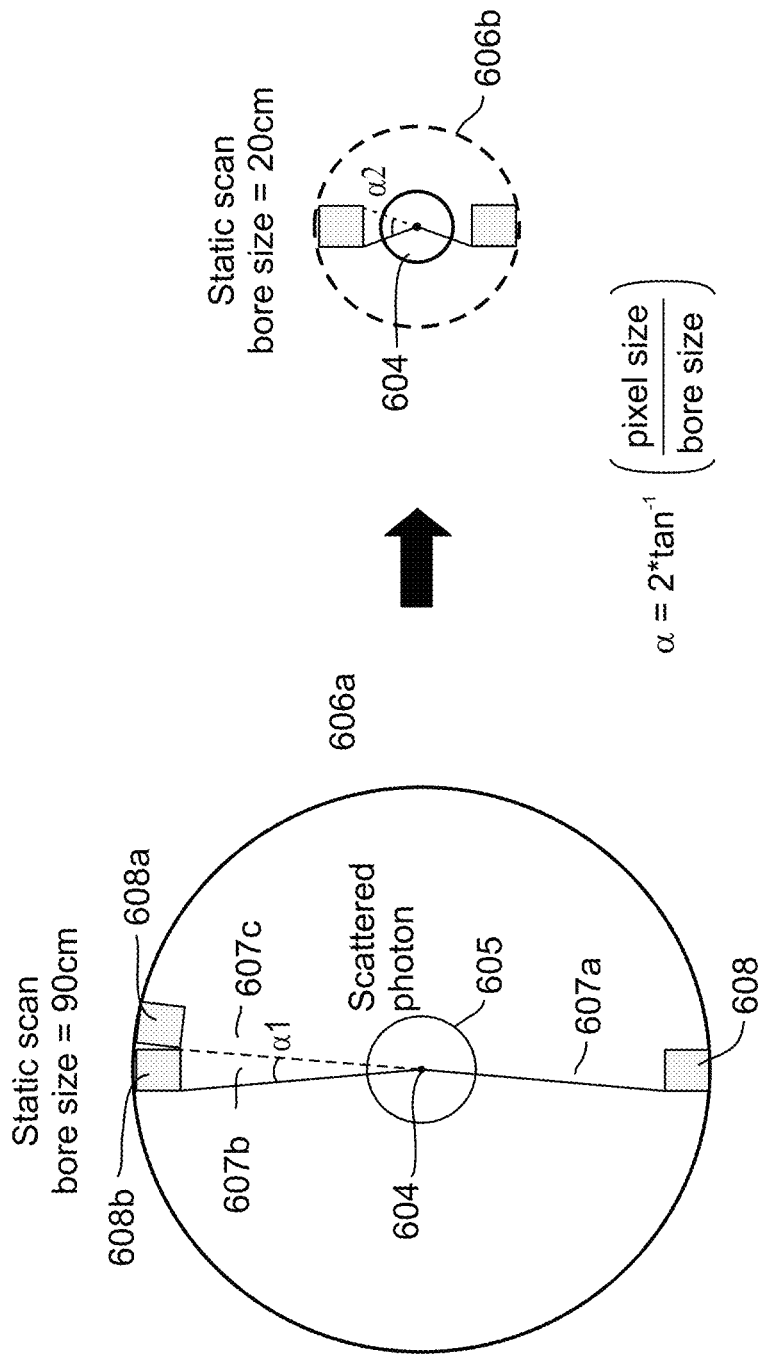
FIGS. 6C and 6D illustrate advantages of variable bore size as implemented according to some embodiments of the invention.

One potential effect (which may be beneficial) resulting from matching the bore size to the ROI being examined is an increase in the acceptance angle for incoming and/or scattered photons. This is illustrated in FIG. 6C. Here, a small ROI 604 is assumed to be centered in a bore 606a that is large compared to the ROI, or in a bore 606b that is closely matched to the size of the ROI. In an exemplary embodiment of the invention, an emission event 605 is assumed to be centered in ROI at 604. As a result of scattering the two photons travel along angularly displaced paths: 607a for the un-scattered photon and 607b for the scattered photon, instead of path 607c. The acceptance angle α, i.e. the angular error between paths 607b and 607c, is a function of the bore size and the detector pixel size according to the relationship:

$$\alpha = 2 * \tan^{-1}\left(\frac{\text{pixel size}}{\text{bore\_size}}\right)$$

In an exemplary embodiment of the invention, an acceptance angle α1 for the large bore can be increased to an angle α2 of, for example, up to about three or four times without degrading or decreasing resolution by reducing the bore size to match the ROI.

Figure 6D:
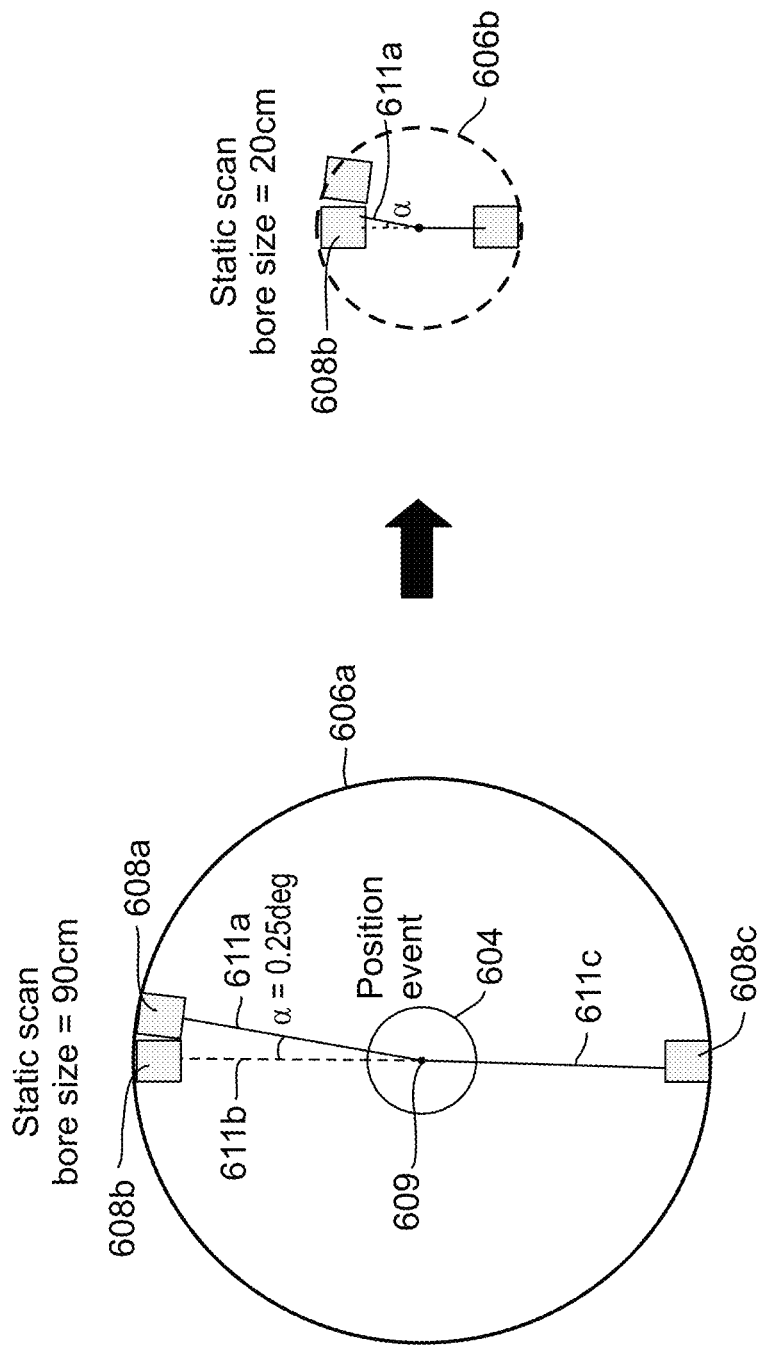

Another effect, potentially beneficial which may result from matching the bore size to the ROI being examined is illustrated in FIG. 6D. This relates to reduction of the so-called "non-co-linearity effect" resulting from residual momentum of the electron and positron annihilation. A positron event 609 produces emission of a photon pair that do not travel in exactly opposite directions. One photon travels along a path 611a instead of 611b and is detected by a detector head 608a instead of 608b, while the other travels along path 611c and is detected by detector head 608c aligned with detector head 608b. By decreasing the bore size from 90 cm to 20 cm, the photon on path 611a is detected by detector head 608b, whereby degradation of resolution due to non co-linearity can be reduced by a factor of up to, for example, 2 or 3 or more with a smaller bore size.

In general, the improvement factor is dependent on the starting and ending bore sizes. In the illustration it is reduced from 90 cm to 20 cm. The angle error due to non-colinearity is about ±0.25 degree. This error is estimated, for example, based on the energy range of the residual momentum of the electron and positron annihilation. The resolution degradation correspond to the shift between the theoretical event position (when colinearity is perfect) to the actual event position. The error can be estimated with simple trigonometry as Err=tan(alpha)*(Bore_size/2). The error for the 90 cm and 20 cm bore size can therefore be reduced by up to about 4.5.

Adjustment of bore size by extension and/or retraction of the individual detector heads may be achieved in various ways. A linear motion mechanism can be implemented, for example, with a DC or AC motor, or linear actuator, by a stepper motor or hydraulically. Position detectors, for example, limit switches, resettable counters, or digital or analog encoders, may be used to provide position feedback and/or avoid over extension and/or collision. The scope of the invention is not necessarily limited by these methods and other ways will be apparent to those skilled in the art as well.

Figure 6E:
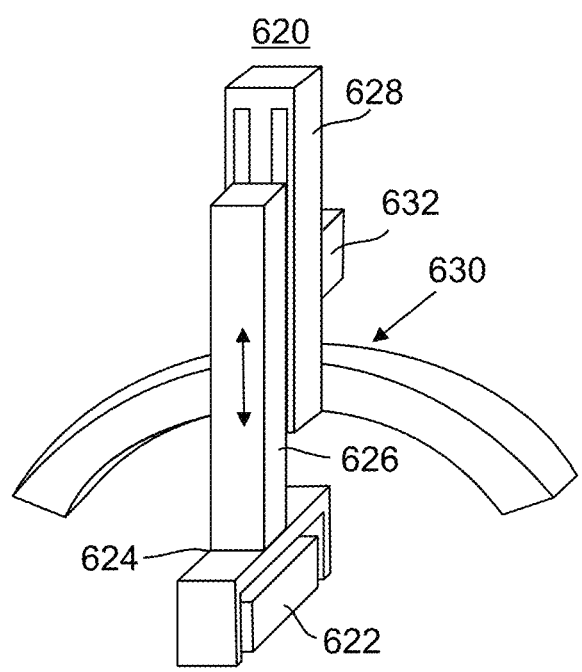
FIG. 6E is a side perspective view that illustrates schematically a linear motion mechanism according to some embodiments of the invention.
Figure 6F:
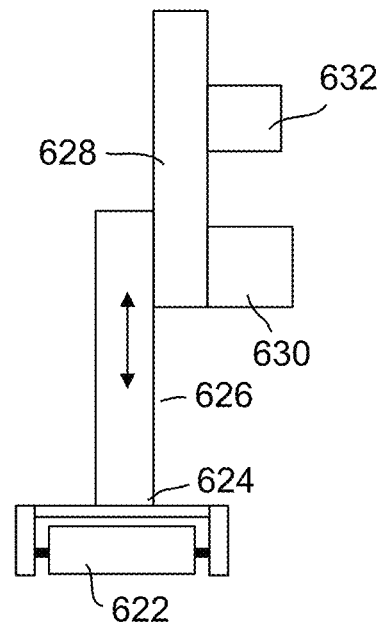
FIG. 6F is a side elevation of FIG. 6E.

FIGS. 6E-G illustrate an arrangement generally designated at 620 for extending and retracting a detector head 622, according to some exemplary embodiments of the invention. FIG. 6E is a top and side perspective view, FIG. 6F is a side elevation, and FIG. 6G illustrates an exemplary linear actuator.

Sub-assembly 620 includes a detector head 622 located at one end 624 of an arm 626, which is movably mounted on a linear rail 628 extending radially on a gantry 630. Within or (optionally) attached to the outside of arm 626 is a linear actuator arm 634 (FIG. 6G). Control of extension and retraction is provided by system controller 30 (see FIGS. 2A-2B).

A weight 632 chosen to balance the weight of detector head 622 and arm 626 is moveably mounted on rail 628 and attached to arm 626 for example, by a suitable pulley arrangement and belt or cable or in any other suitable and/or desired manner. For example, the weight can be between 0.5 Kg and 30 Kg, for example, between 3 Kg and 20 Kg, for example, 7 Kg. Optionally, the moving part of the detector weighs between 1 and 30 Kg. Optionally, the entre arm module weights between 2 and 50 Kg, for example, between 5 and 30 Kg.

Referring to FIG. 6G, in which some parts are omitted in the interest of clarity, in the illustrated example, arm 634 includes a driving member 636, for example, a sprocket, and a driven member 638 which may also be a sprocket. Input power is provided by a rotary actuator such as a motor described above (not shown) attached to sprocket 634. A chain (not visible in FIG. 6G) is carried by sprockets 634 and 636.

Attached to the chain are travelers 638 and 640, which respectively carry detector head 622 and its arm 626, and counterweight 632. As will be appreciated, in an exemplary embodiment of the invention, when the chain is driven, the detector head and counterweight move in opposite directions, as indicated by arrows 644 and 646.

Such an arrangement allows use of a very small force for extension and retraction while gravitation does not produce any motion or resistance since the counterweight provides a balancing counter force equal to the projection of the total force (vector) along the path of linear motion.

In some exemplary embodiments, for a detector head weighting about 20 kg, counter-balance can be provided by a weight of approximately 19.5 kg, so a force of only about 0.5 kg will be needed to be employed for moving the detector head.

Such a very gentle force potentially reduces risk of patient injury in case of a collision. Moreover, in case of a collision, the patient can typically easily resist such gentle force and/or move the arms away regardless of their orientation.

Additional or alternative collision avoidance protection may be provided by proximity sensors of various types. Some options include pressure sensors, acoustic, e.g., ultrasound sensors, and optical sensors mounted on the detector units and coupled to control the actuator motor in a suitable manner. In one example, a controller receives an alert when the distance is below a certain threshold. In another example, the motor is stopped (or a brake activated or motor disengaged) by a dedicated electrical circuit reading the sensor.

In some embodiments, the detector heads are brought into close proximity to the patient's body, e.g., within less than 20 cm, or less than 10 cm, or less than 5 cm or within 1-2 cm or in substantial contact or larger or smaller or intermediate distances.

Optionally, in some embodiments, contact with the patient's body is allowed, but the allowable force on the body/skin is limited, for example, to less than 1000 g, or less than 200 g, or less than 50 g, or less than 10 g or intermediate contact forces. In an exemplary embodiment of the invention, the contact area is at least 1-10 cm squared, optionally by having detector not have sharp edges in direction of body.

In an exemplary embodiment of the invention, consideration is given to assuring that adjacent heads do not interfere mechanically or operationally. FIGS. 7A and 7B, 8A-8D, 9A-9C, 10A and 10B, and 11A-11C illustrate exemplary design solutions according to some embodiments of the invention.

Figures 7A, 7B:
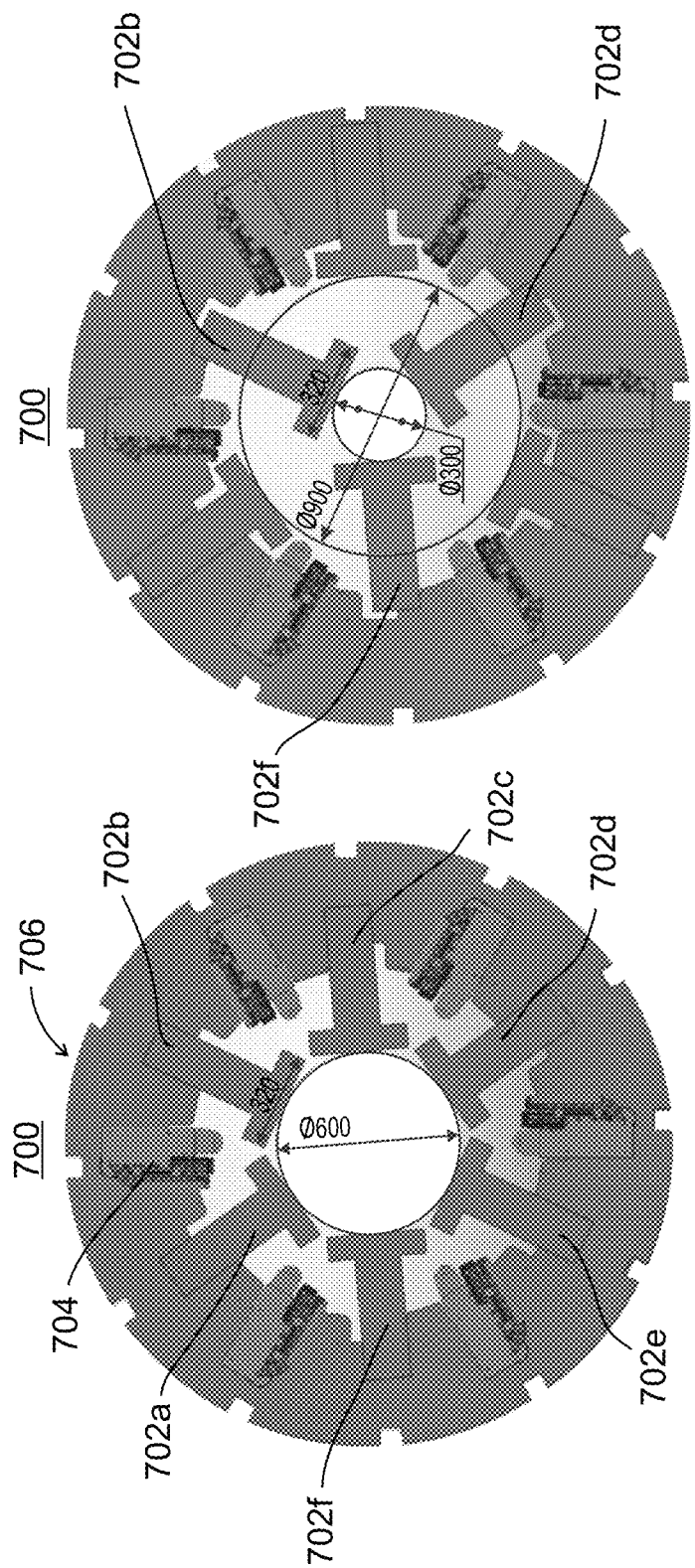
FIGS. 7A and 7B illustrate a way to achieve variable bore size shown by way of example for a system operating in a PET mode according to some embodiments of the invention.

FIGS. 7A and 7B illustrate a dual-mode system 700 comprised of a detector array 706 comprised of six PET detector heads 702a-702f arranged in three pairs 702a,d, 702b,e, and 702c,f and six SPECT detectors 704. System 700 is illustrated as being used in PET mode. In FIG. 7A, The PET detectors comprised in array 706 are in and extended operating configuration for example suitable for performing full body scans. However, because of the shape of the PET detectors, FIG. 7A is also about the minimum practical extension that is achievable due to the size and shape of the detector heads.

In an exemplary embodiment of the invention, the controller includes a geometry engine which simulates the space filling properties of the detectors so as to plan and/or monitor motion in a manner which avoids interference between moving (and/or unmoving components). Optionally or alternatively, the geometry engine also calculates lines of sight and/or obstructions. In an alternative embodiment, allowable paths and/or positions (e.g., for one or more detectors) are pre-calculated and provided to the system, which uses such paths and/or positions.

To achieve a smaller bore size with detector array 706, only some, for example one-half of, or any subgroup of, the detector heads, for example, detector heads 702b, 702d, and 702f, are extended, as illustrated in FIG. 7B. The other detector heads 702a, 702c, and 702e remain in a fully retracted position. In some embodiments, only the extended detector heads are used. In other embodiments, all the detector heads are used, but the sensitivity and/or resolution of the extended detector heads may be not the same as for the un-extended detector heads. This is optionally accounted for in the course of processing the emission data.

Figure 8B:
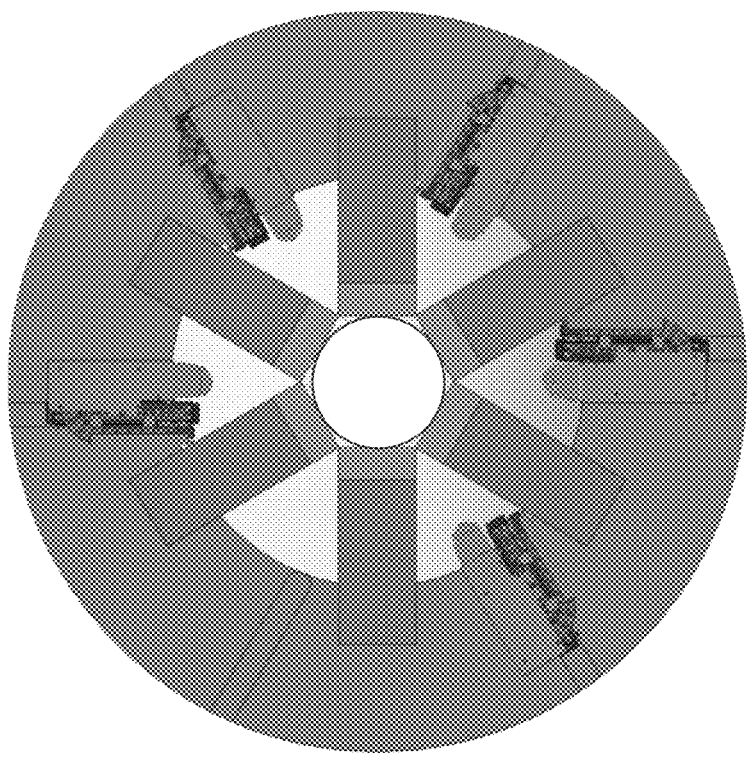

FIGS. 8A-8D illustrate other ways to achieve smaller bores, one such way, again in a dual-mode system being operated in a PET mode. FIG. 8A shows the detector element carrying portions of PET detector heads 806a, 806c, and 806e rotated 90 degrees around their respective longitudinal axes (i.e., in a plane perpendicular to the longitudinal axes. Compared with FIG. 7A, it may be seen that a smaller bore is achieved.

FIG. 8B shows a configuration in which all the PET detector heads 802 have been rotated by 90 degrees, allowing the greatest reduction in bore size.

Figure 8C:
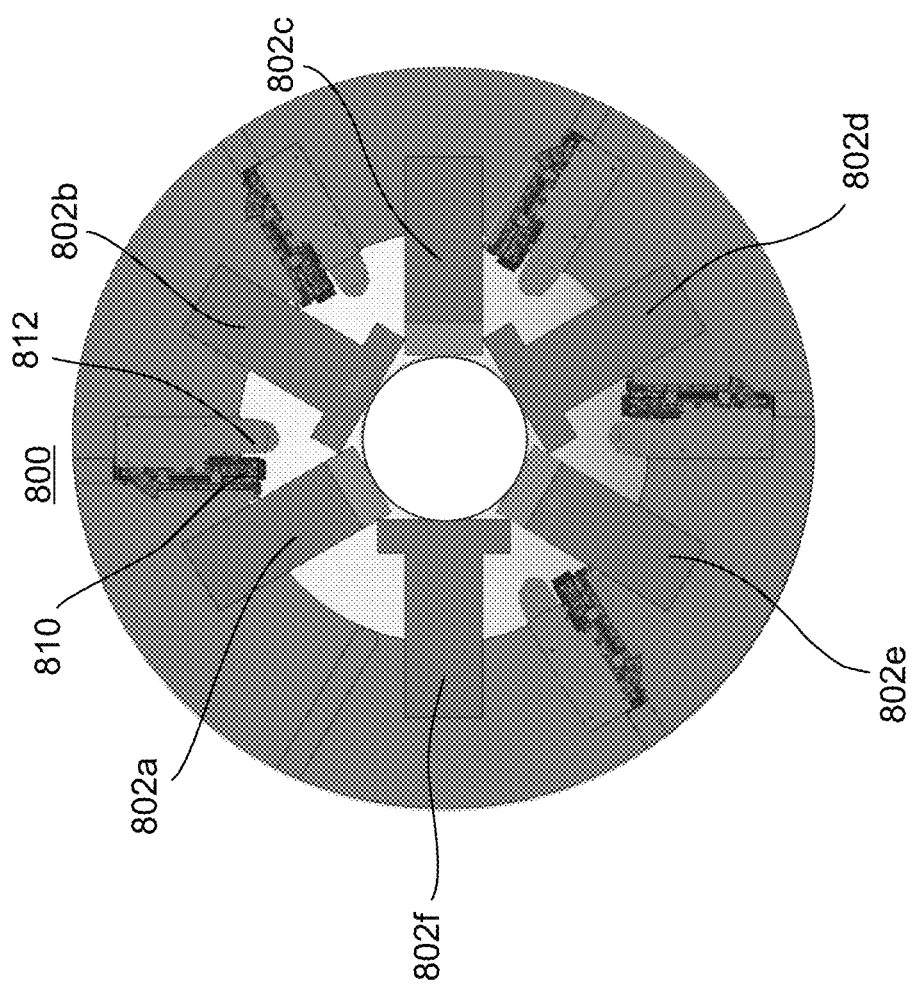

FIG. 8C represents a situation in which all of detector PET heads 802 have been rotated by less than 90 degrees, for example, 45 degrees.

Such rotation may take place, for example before during or after extension, and/or during a scan as described below.

FIG. 8C illustrates the effect of rotating the PET detector heads 806a-806f to an angle between 0 degrees and 90 degrees relative to the orientation in FIG. 8A, followed by extension. As may be seen from FIG. 8C, such rotation can result in overlap of adjacent detector heads.

In some embodiments of the invention, as the angle of rotation increases toward 45 degrees, the overlap increases, but decreases as the angle of rotation increases further toward 90 degrees, at that point, the limiting case of no overlap is reached, as illustrated in FIG. 8B.

The rotation shown in FIGS. 8A-8D can be implemented in various ways. For example, small bidirectional motors (not shown) may be mounted on gantry 814 and connected through a position tracking arrangement, for example, using encoders and/or limit switches coupled to detector shafts 808a, etc. Optionally, each detector head unit may include a built-in rotation actuator. Other mechanical arrangements may also be used, for example, a hydraulic arrangement, or manual adjustment may be also be employed. Optionally, for this and/or for actuators for extension and retraction, the motors are controlled by the system controller.

Figure 9C:
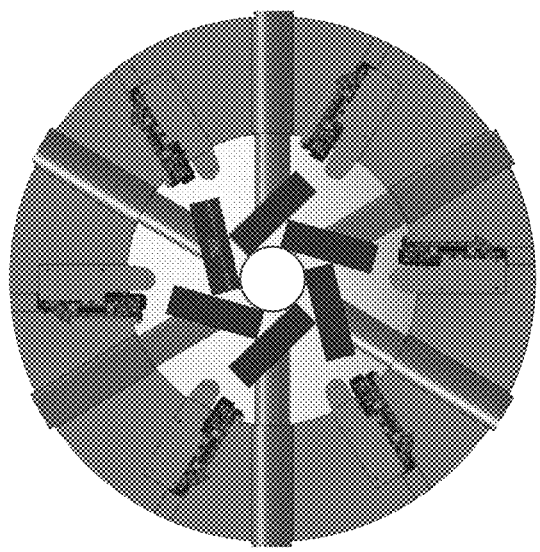
FIGS. 9A-9C illustrate yet another way to achieve variable bore size shown by way of example for a system operating in a PET mode according to some embodiments of the invention.
Figure 9B:
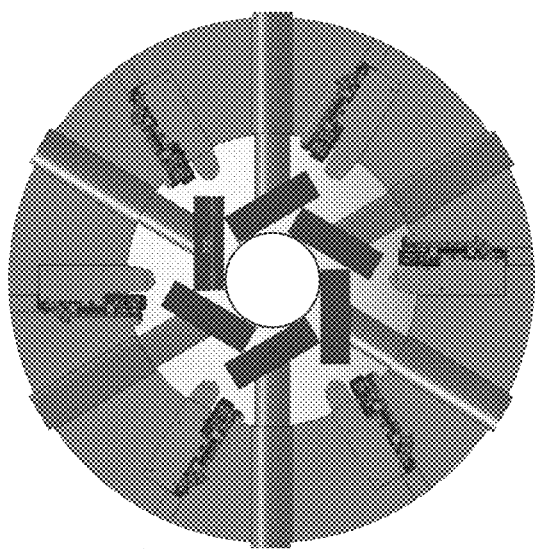
Figure 9A:
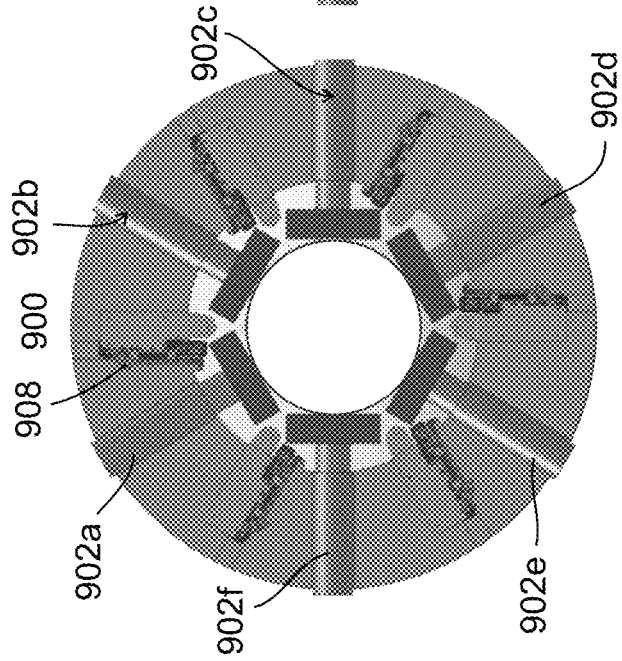

Another way of reducing bore size is illustrated in FIGS. 9A-9C. FIG. 9A illustrates a system 900 in which the individual detector heads 902a-902f in a detector array 906 are partially extended, for example, for a full-body PET scan, and also are oriented in planes perpendicular to the respective axes of elongation of the detectors as in the other embodiments described up to now. However, it should be noted that the extension illustrated in FIG. 9A is about the greatest possible extension since attempted further extension is blocked by peripheral contact between the detector heads.

In an exemplary embodiment of the invention, to create clearance for further extension and reduction of the bore size, the detector heads are tilted out of the perpendicular planes by pivoting them around axes that run parallel (and/or perpendicular and/or other axes that are in the plane of the detector) to the longitudinal axis of the system, e.g., in the direction parallel to direction of relative movement by which the successive axial slices are produced. As a consequence, as illustrated in FIG. 9B, adjacent detector heads, e.g., heads 904a and 904b overlap peripherally allowing a degree of extension of detectors 902a-902f not achievable with the heads in the respective perpendicular planes as illustrated in FIG. 9A.

Optionally, to achieve yet further reduction in bore size, heads 904a-904f are tilted even further as illustrated in FIG. 9C thereby increasing the overlap and allowing additional extension.

The tilting shown in FIGS. 9A-9C can be implemented in various ways similar to those employed in the embodiments of FIGS. 8A-8C, as will be understood by persons skilled in the art.

It is noted in these and other embodiments, that the detector plane need not be flat. For example, it may be curved being a section of a cylinder, a sphere and/or other conic section and/or other curved and/or piecewise linear shape.

Figure 10B:
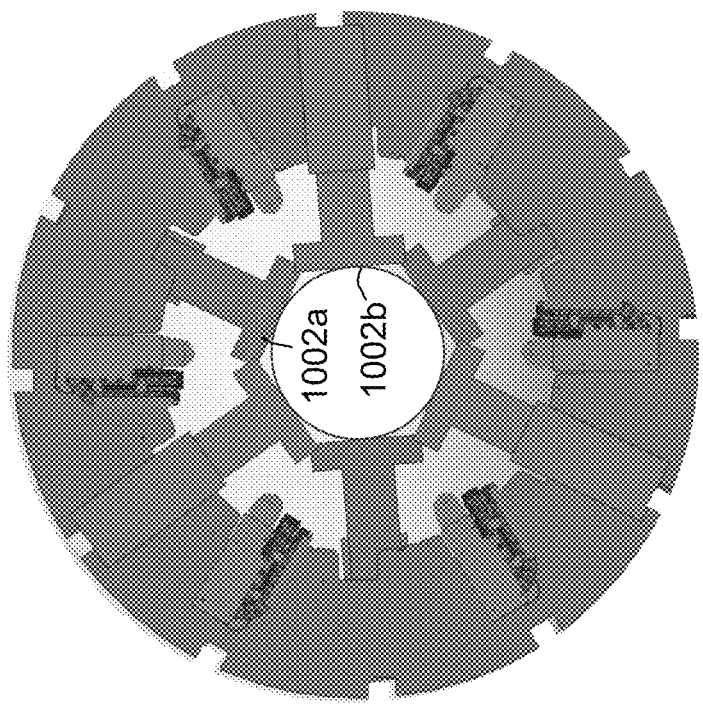
FIGS. 10A and 10B illustrate still another way to achieve variable bore size shown by way of example for a system operating in a PET mode according to some embodiments of the invention.
Figure 10A:
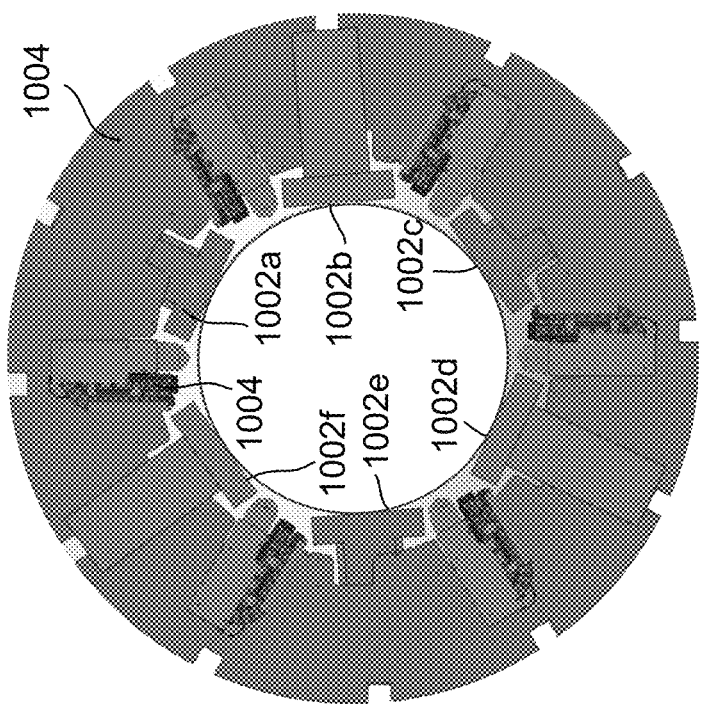

FIGS. 10A and 10B illustrate a detector array 1000 employing a further way of achieving a wide range of bore sizes, which is optionally used together with other methods as described herein. Here, detector array 1000 includes six PET detector heads 1002a-1002f and six SPECT detector heads 1004a-1004f mounted on a gantry ring 1006. To accommodate the shape of the PET detectors, detector head pairs 1002a, 1002d and 1002c, 1002f are located in a first plane on the gantry, while intervening detector head pairs 1002b, 1002e, are located on a second plane spaced axially from the plane of the other two pairs.

FIG. 10A illustrates extension of the PET detectors to achieve a first desired bore size. To achieve a smaller bore size, the detectors are extended as desired, as shown in FIG. 10B. Because of the axial spacing, even after the detectors have been extended sufficiently that they would come in peripheral contact if they were situated in a single plane, further extension is possible because the axial spacing allows the tip of one detector, for example 1002a, to pass behind the adjacent tip of the next detector 1002b.

As will be appreciated, suitable modification of the programming of the coincidence detection sub-system may be made to account for the axial spacing. In some embodiments the programming does not need to be modified (but only parameters or look up tables) since it just needs to note the non-uniform viewing when determining relative counts/normalizing from different areas (e.g., using sensitivity maps and/or other calibration maps).

Figure 11C:
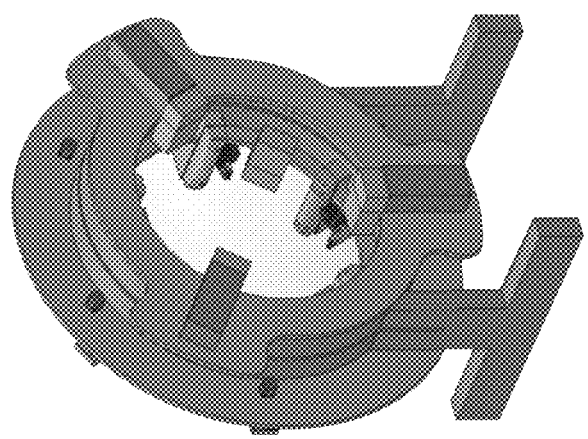
FIGS. 11A-11D illustrate still another way to achieve variable bore size according to some embodiments of the invention.
Figure 11B:
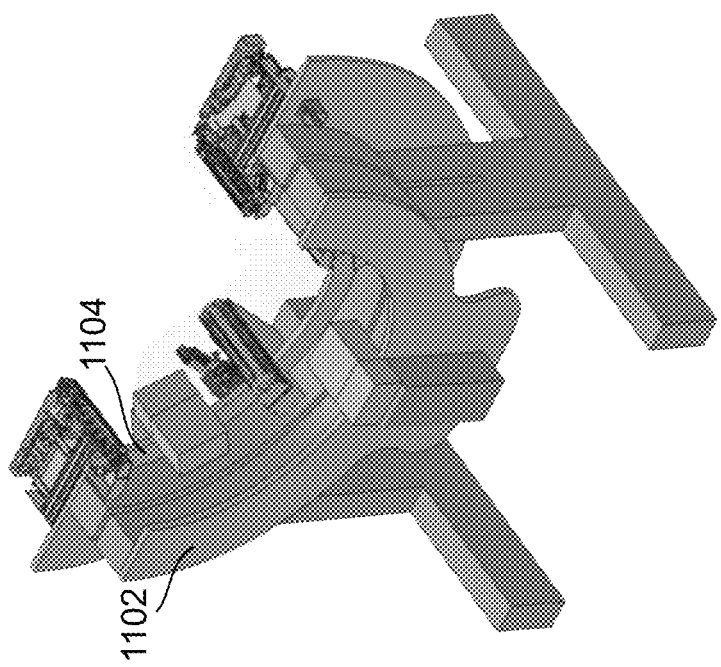
Figure 11A:
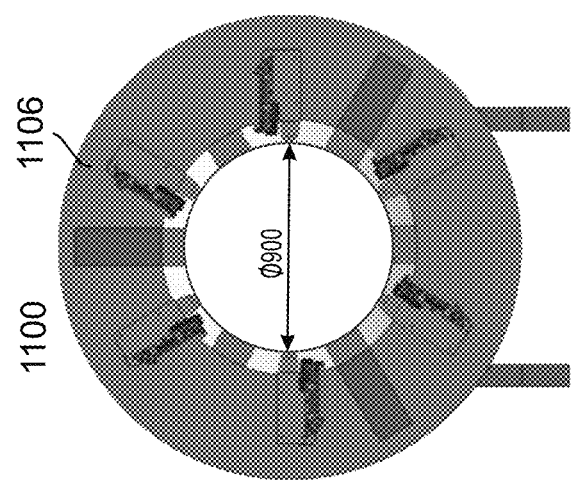

FIGS. 11A-11C illustrate another arrangement for achieving a wide range of bore sizes involving axial spacing, which may be used, for example, alone or with other methods described herein. FIG. 11A is an end view of assembled detector array 1100. FIG. 11B is a perspective view with the top portion cut away and FIG. 11C is a perspective view rotated 90 degrees from that of FIG. 11B to show internal construction details.

Here, detector array 1100 is comprised of six PET detectors 1102 and six SPECT detector heads 1104. To accommodate the shape of the PET detectors, detector pairs 1002a, 1002d and 1002c, 1002f are located on a first ring 1106 of a gantry 1108, while intervening detector pair 1102b, 1102e, is located on a second ring 1110 spaced axially from the ring of the other two pairs. Optionally, since ring 1110 carries only one PET detector pair, all the SPECT detectors may be mounted on that ring.

Figure 11D:
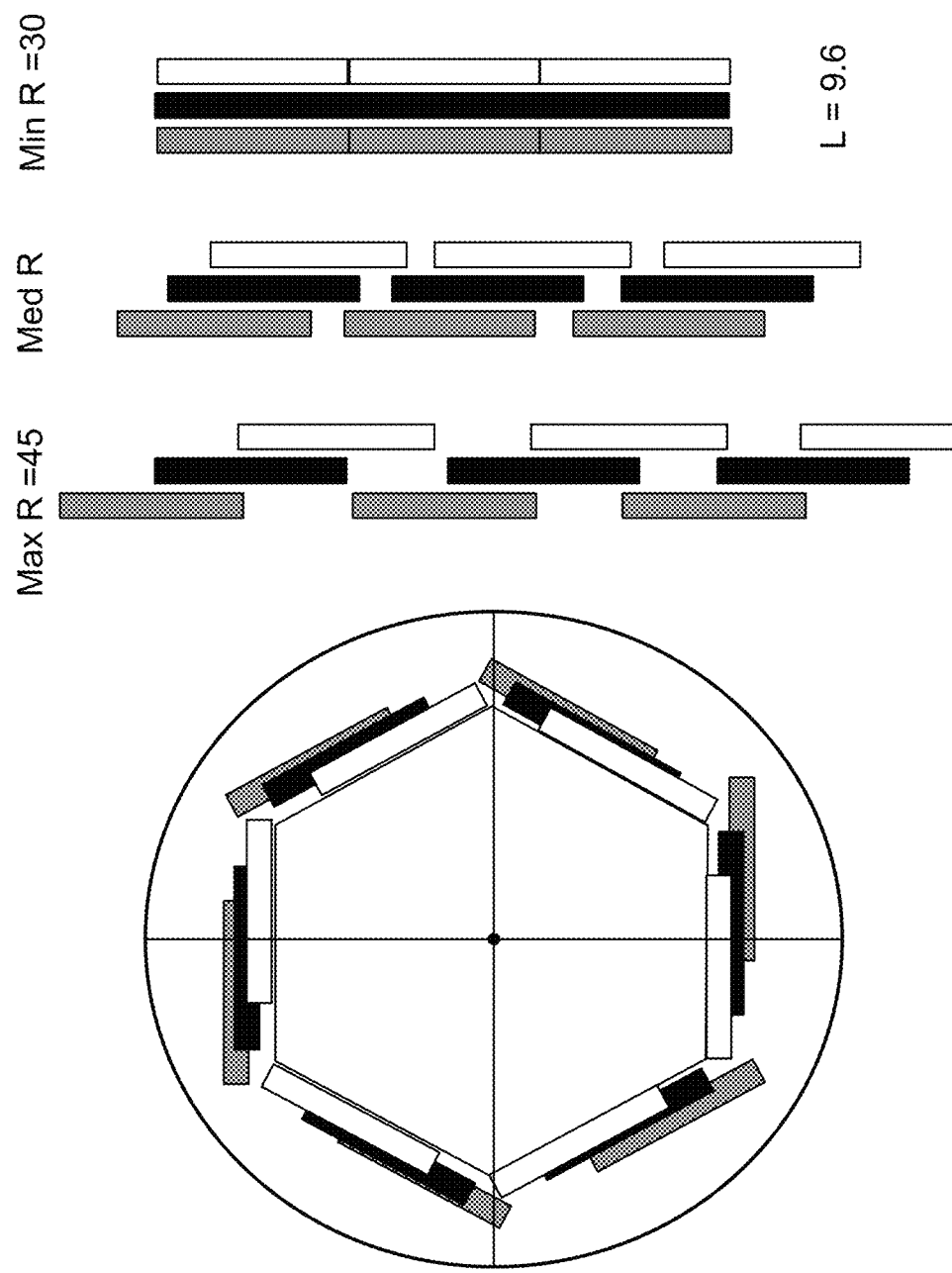

Optionally, more than two rings may be provided. FIG. 11D shows an embodiment in which the detector heads are arranged in three layers, either on one ring or on three separate rings. Additional rings, for example, 3, 4, 5, 6 or more may be provided (and optionally added in a modular manner). In an exemplary embodiment of the invention, the detectors on different rings are of different types, sizes and/or qualities.

Figure 12A:
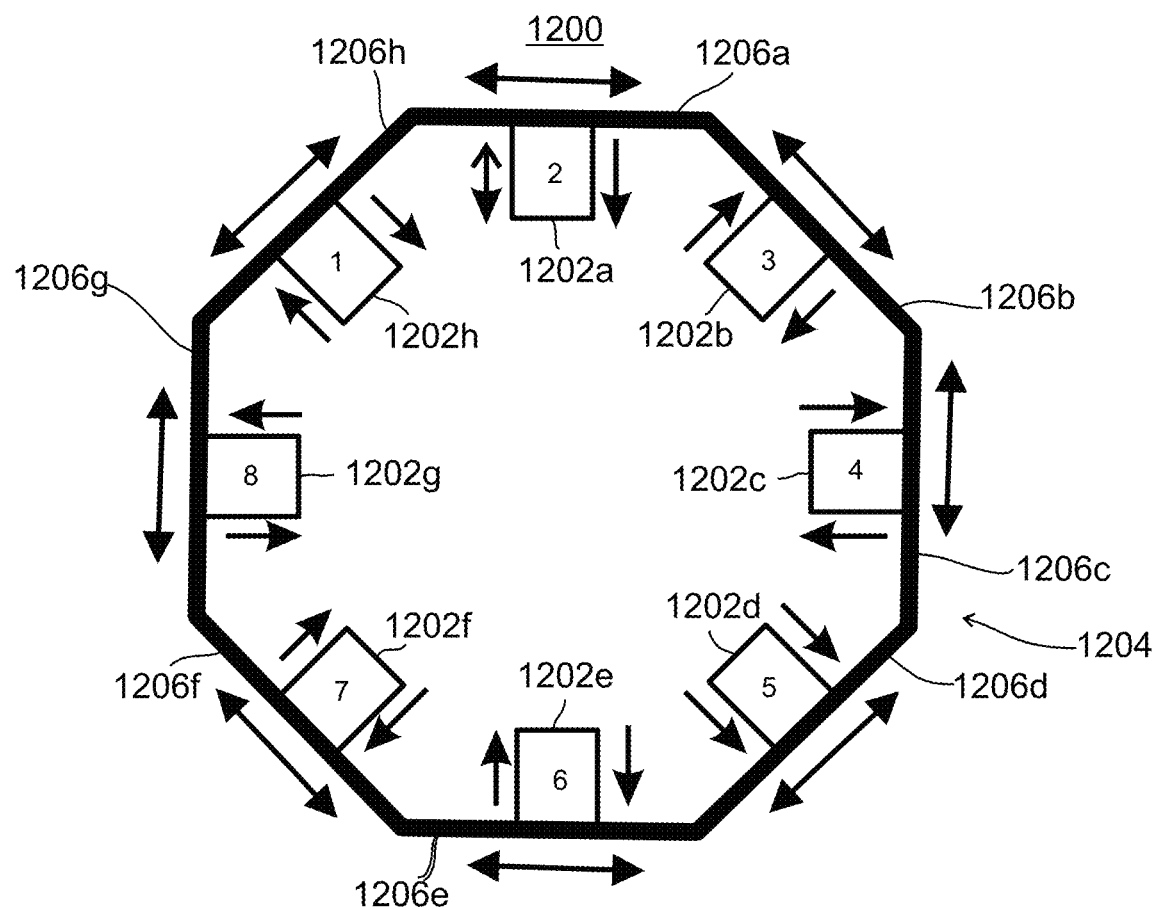
FIG. 12A illustrates an exemplary embodiment in which detector heads are translatable linearly on a gantry.

Detector Head Movement on the Gantry and Gantry Rotation:

A potential benefit of the variable geometry aspect of some embodiments of the invention is the possibility of obtaining good resolution and sensitivity around the entire ROI with a reduced number of detector units that are laterally or circumferentially moveable on a gantry. FIG. 12A illustrates schematically one way of translating detector heads on a gantry. Here, eight detector heads 1202a-1202h are slidably mounted on a track assembly 1204 comprised of separated track segments 1206a-1206h.

In an exemplary embodiment of the invention, heads 1202 may be moved along their respective track segments by a linear motion arrangement similar to that described in connection with FIG. 6G, or by any other suitable and desired arrangement.

Various movement options may be provided, as will be apparent to those skilled in the art in light of the disclosure herein, for example, but not limited to (a) prepositioning (b) steps of a step and shoot regimen, (c) adjustment of position between axial slices, and (d) "on the fly" adjustment during gantry rotation or a spiral scan. It should be recognized that combination of the indicted or other options are also contemplated. Further it should be recognized that the detector heads may be positioned either uniformly or non-uniformly around the gantry. Movement over any desired range depending on the number of detector heads possible, for example, 20 degrees (i.e., ±10 degrees from a central position). The described arrangements are applicable to PET and SPECT detector heads as well as dual purpose heads as described below.

Figure 12B:
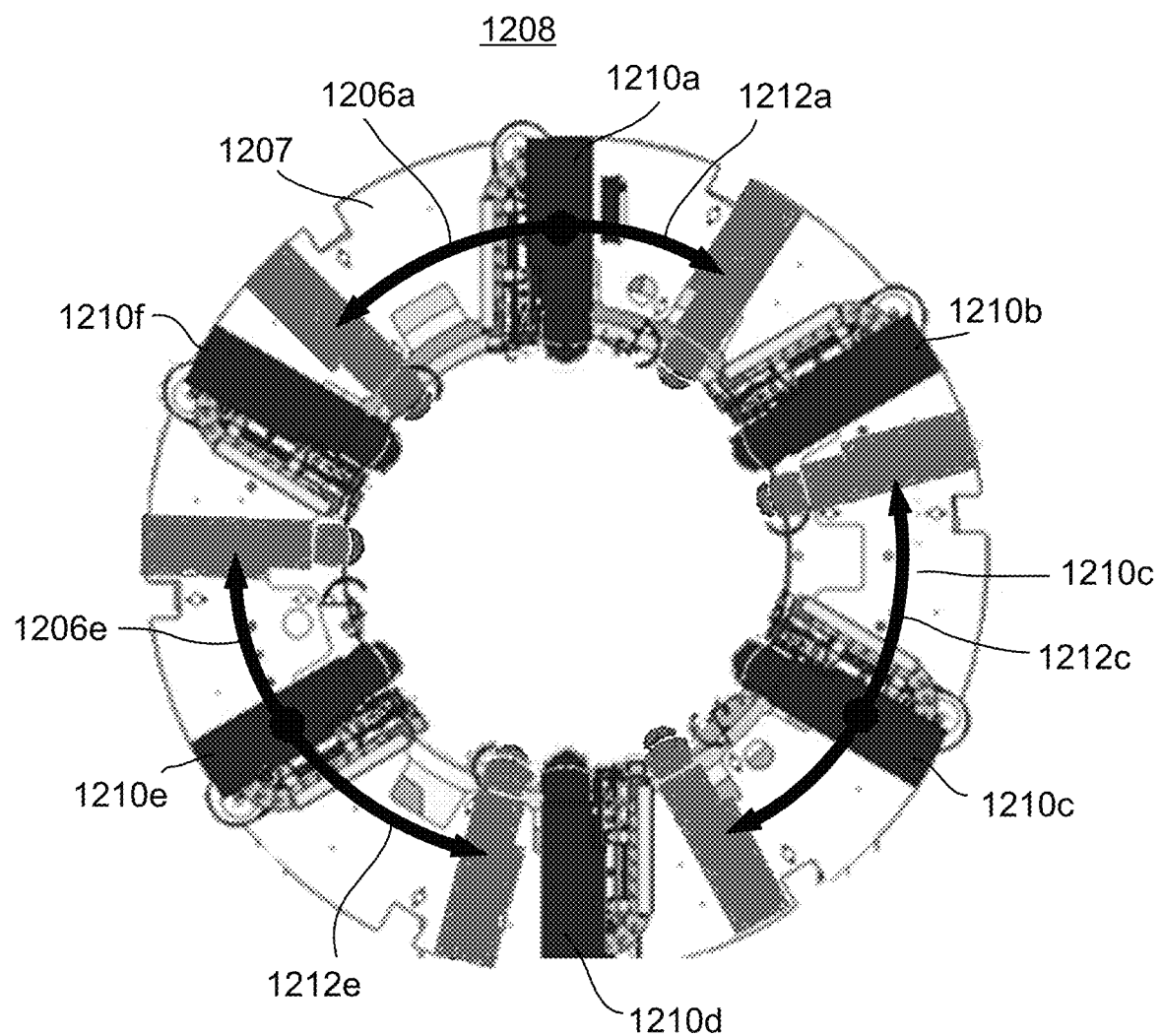
FIG. 12B illustrates an exemplary embodiment in which detector heads are translatable circumferentially on a gantry.

FIG. 12B illustrates an alternative arrangement in which the detector head move circumferentially on the gantry. Here, a detector array 1208 mounted on a gantry 1209 includes six detector heads 1210a-1210f. With respect to at least some designs, the concepts being described are equally applicable to PET and SPECT detectors. As in other embodiments described, the detector heads can be extended and/or retracted, and/or optionally rotated or tilted, to vary the bore size.

In an exemplary embodiment of the invention, for example, to achieve a variation in spatial resolution around the ROI, some of the detector heads, for example detector heads 1210a, 1210c, and 12104, are moveable circumferentially on gantry 1209 as indicated by arrows 1212a, 1206c, and 1212e. As a result, in the embodiments of both FIGS. 12A and 12B, there can be more detectors in some areas, and in other areas, there can be fewer detectors. Optionally, detector heads can be concentrated in the wide areas to provide enhanced resolution in those areas. Optionally or alternatively, different detector head qualities are used in different areas, for example, to support non-uniform data collection protocols.

A possible benefit of the translational embodiment of FIG. 12A is that it may be easier to implement. Arcuate motion, or translation over a range of ±about 15 to 30 degrees, for example, ±20 degrees from a central position can give good results.

Figure 13:
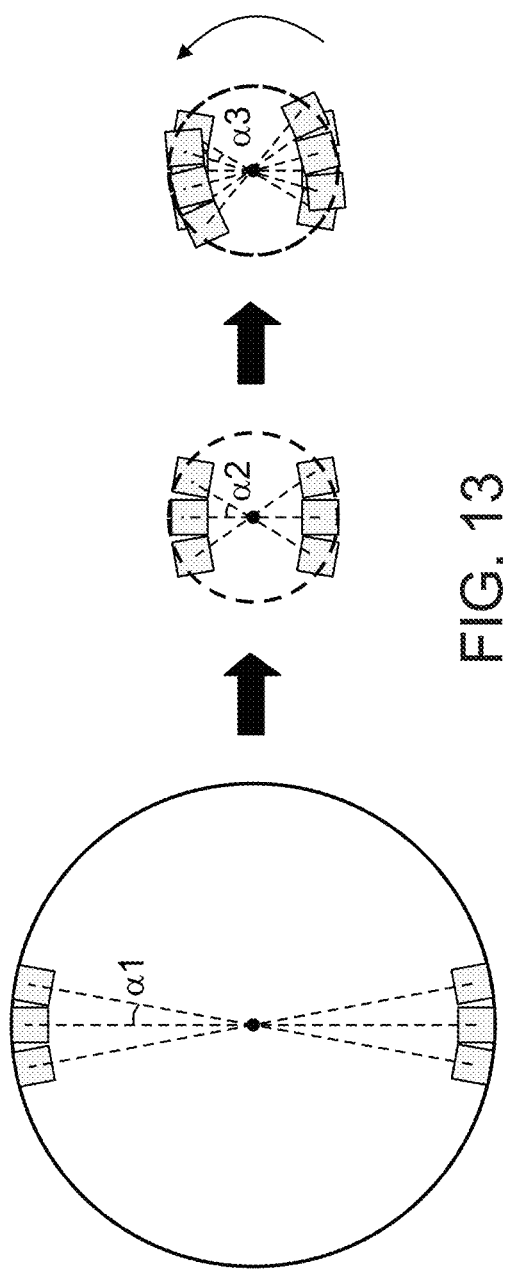
FIG. 13 illustrates benefits of continuous rotation of a detector carrier according to some embodiments of the invention.

Another way to enhance resolution around an ROI with a reduced number of detector heads is to provide gantry rotation for PET operation as in SPECT operation. This concept is illustrated in FIG. 13. In a non-rotating system, reducing the bore size from the conventional 90 cm to 30 cm for a small ROI for a particularly configured detector head results in a larger angle of acceptance $\alpha 2$ as compared to $\alpha 1$, but may decrease the angular resolution, e.g., as previously noted. However, if the gantry is continuously rotated, or continuously rotated during imaging of successive axial slices, e.g., with the same number of detector heads, and a bore size of 30 cm, the angle of acceptance $\alpha 3$ can be made smaller, for example, smaller than even $\alpha 1$, and the lost angular resolution can be recovered. Optionally, the speed of rotation is selected according to the desired acceptance angle. In an exemplary embodiment of the invention, with a rotating gantry, the detector array can be configured with a number of detector heads arranged over less than the full 360 degrees around the ROI, for example, over between 180 and 320 degrees. In a static system, that would result in a potentially large gap in coverage. Rotation assures that emission events from all parts of the ROI will be detected as the detector array rotates, even though generation of the image data may require more time.

A rotating gantry can also be provided in embodiments in which the detector heads are mounted on axially spaced gantry rings and/or translatable on the gantry, yielding the benefits of both a wide range of bore configuration adjustability and increased angular resolution with fewer detector heads. Optionally, the two gantry rings can be arranged to rotate at different speeds.

Figure 14:
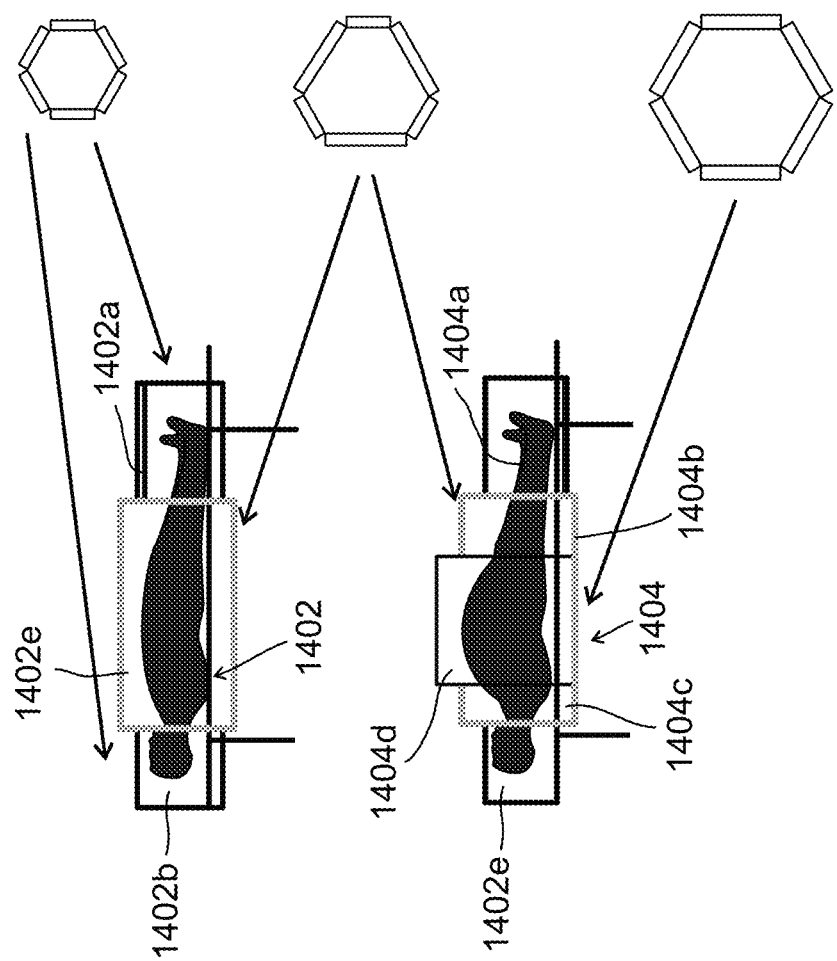
FIG. 14 illustrates an arrangement for dynamically varying the bore size during a scan.

FIG. 14 illustrates a potential benefit of varying the detector geometry during a full-body scan. For a normal patient 1402, a small bore is used for the slices in the regions 1402a and 1402b of the lower legs, neck, and head, and a larger bore size for the region 1404c of the upper legs and the torso. In contrast, for an obese patient 1404, a larger number, for example, four bore sizes gives better results. Thus, for regions 1404a and 1404e covering the lower legs, the head and the neck, a first bore size is used. For regions 1404b and 1404c covering the upper legs and the upper torso, a second larger bore size is used. For region 1404d covering the lower torso and the chest, a third bore size, even larger than those for the other regions is used.

A further option is to vary the bore size on-the-fly as the scan proceeds, resulting in a bore size that dynamically follows the contour of the patient's body.

It should also be noted that for an ROI that is relatively small, decreasing the bore size can be facilitated by making the patient carrier transversely adjustable or with a part that is narrower than the overall width.

Figure 15:
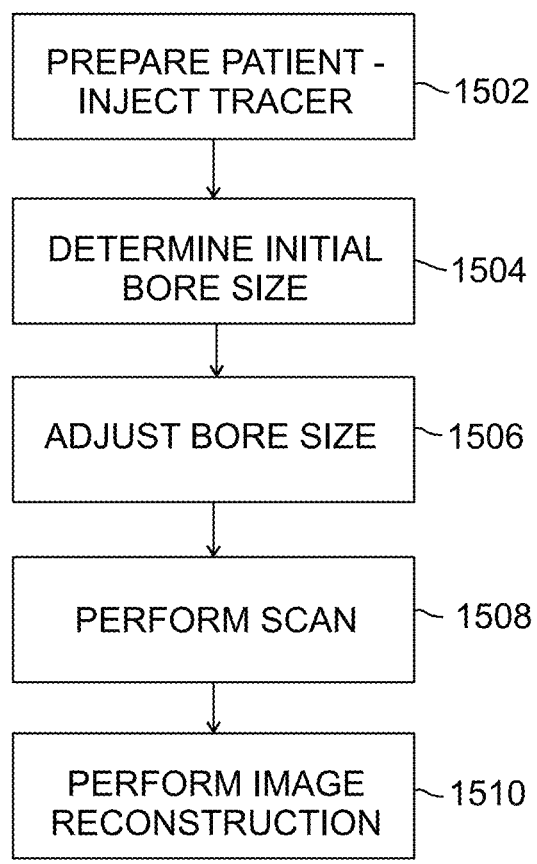
FIG. 15 is a flow diagram illustrating use of an N-M tomography system according to other embodiments of the invention.
Figure 16:
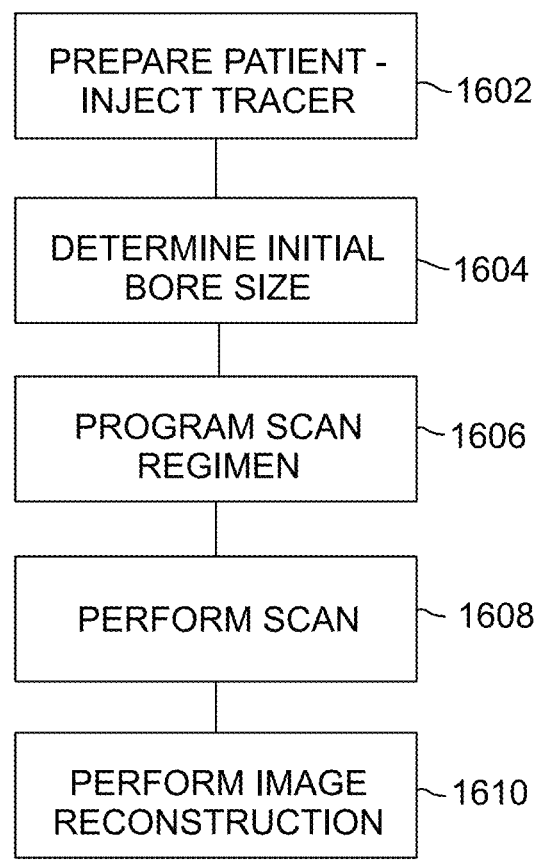
FIG. 16 is a flow diagram illustrating use of an N-M tomography system according to some other embodiments of the invention.

Exemplary Method of Use:

While it is believed that the method of use of the various embodiments described above should be apparent to those skilled in the art from the foregoing description, this may be summarized in conjunction with the flow diagram of FIGS. 15 and 16. For purposes of discussion, it is assumed that a PET procedure or a SPECT procedure is to be performed either in a single or dual mode system, but it should be understood that the discussion is also applicable to simultaneous performance of PET and SPECT procedures.

As shown, at 1502, suitable preparation of the patient, including injection of the radioactive tracer is optionally undertaken. At 1504, optionally while (and/or before, and/or after) the tracer is circulating through the bloodstream to the ROI, the size and shape of the ROI is determined, for example by a conventional transmission CT. Optionally, the CT may be performed using a CT capability (e.g., using an x-ray or radiation source) included in the N-M tomography system itself, or by use of a separate CT system.

At 1506, the bore geometry and if necessary, the configuration of the collimator septa are adjusted to accommodate the size, shape, and location of the ROI and the desired spatial resolution according to the nature of the procedure being performed. Depending on the required size of the bore, the detectors are extended as needed. If the detectors cannot be extended sufficiently to provide as small enough bore, only some of the detectors are extended. Alternatively, according to the features of the particular system, the detectors are rotated and/or tilted to the required angular orientation, and optionally then the detectors are extended.

At 1508, after sufficient time (and/or during this time) for the tracer to travel through the patient's bloodstream to the ROI, the scan is performed, and at 1510, the image reconstruction is performed.

FIG. 16 illustrates a more complex scan procedure, again applicable in general to a PET or a SPECT procedure, or simultaneous performance of both PET and SPECT procedures. Here, 1602 and 1604 are the same as 1502 and 1504, but at 1606, a scan regimen is programmed for in-scan detector and collimator geometry variation. This may include one or more of the following features:
  a) Preliminary bore size adjustment;
  b) Continuous gantry rotation during the scan or at each axial slice;
  c) Gantry rotation speed adjustment;
  d) Continuous bore size adjustment (both extension and angular orientation of the detector heads) during the scan at particular axial positions, or continuously over the entire scan;
  e) Variable positioning of the detector heads on the gantry (initially or over the course of the scan);
  f) Variable collimator configuration initially and/or over the course of the scan.

At 1608, after sufficient time for the tracer to travel through the patient's bloodstream to the ROI, the scan is performed according to the programmed regimen, and at 1610, the image reconstruction is performed.

Detector Unit Arrangements and Configurations:

Referring again to FIGS. 2A-2B, it will be recalled that a conventional SPECT detector unit is comprised of an emission detector element 32 in the form of a scintillator that provides an optical (or electrical) light pulse in response to impingement of a gamma-ray photon, an array of photomultiplier tubes (PMT) 34 that convert the optical light pulses into electrical signals from which the images are reconstructed and a collimator arrangement 42 with openings aligned with the PMTs to provide a narrow acceptance angle for each PMT, i.e., to ensure that photons striking the detectors do so at a relatively narrow range of angles. Alternatively, the scintillators and the PMT can be replaced by a direct conversion semiconductor detector, for example, a SiPM as described herein.

Conventional PET detector units can be similarly configured, but do not include a collimator array because incidence angle information is extracted based on coincident detection of two photons emitted by a single radioactive decay.

Scintillation detector elements are typically formed as unitary structures, and such structures are also employed in some embodiments of the invention. Alternatively, the detector elements according to some embodiments are pixilated, e.g., formed of an array of discrete small detector pixels. This can be advantageous particularly for PET imaging, in that it enables identifying the orientation from which the photon has been emitted at a much finer precision, for example, along a line with a width of about 4-6 mm, between two locations of coincident detections taking into account the distance of positron travel before annihilation and the pixel width.

In an exemplary embodiment of the invention, dual use (PET and SPECT) detector systems are provided.

In an exemplary embodiment of the invention, pixilation may in some cases facilitate optionally providing time-of-flight analysis circuitry for PET operation to determine where along the estimated emission line the positron was emitted, for example at a longitudinal resolution of, for example, about 1-5 cm, for example 2-3 cm (e.g., by measuring such time per pixel or group of pixels).

Optionally, the electronic circuitry connected to some or all of the detector units can also provide photon energy characterization (e.g. energy level) within the entire SPECT and PET range of about 40 KeV to 511 KeV, and detection of count rate in case of high flux of photons, for example when a high intensity radiation source is activated such as X-ray source, and/or detection time resolution sufficient for coincidence and time of flight detection.

Optionally, the signal processing electronics can also include multiple separate channels that allow independent amplification and front-end processing for each detector or small group of detectors and/or a small number of pixels (e.g., between 10 and 1000, for example 100), such that any malfunction of one or more pixels or detectors and any blinding of one or more pixels or detectors by a "hot spot" (high intensity source) do not prevent other detectors from properly functioning and detect photons emitted from other regions. One suitable way to achieve this is shown in commonly assigned U.S. Pat. No. 8,445,851 commonly owned herewith, the content of which is hereby incorporated herein in its entirety as if fully set forth. The detector pixels can be arranged in various configurations according to embodiments of the invention. In an example, the detector can be configured as a symmetrical matrix of 8×8 pixels, 10×10 pixels, 12×12 pixels, 16×16 pixels 20×20 pixels, 32×32 pixels, or larger or smaller or intermediate sized matrices. Alternatively, the pixels may be arranged in asymmetric configurations, for example 16×32 pixels, 16×64 pixels, 8×16 pixels, and other larger, smaller or intermediate sized configurations.

In a non-limiting example, detector pixels have dimensions in the range of about 0.1-20 mm, for example, about 0.2-15 mm, for example 0.5-10 mm, for example 1-5 mm, for example 1-2 mm or 2-3 mm or 2-4 mm.

While in an exemplary embodiment of the invention the pixels are symmetric (e.g., square), this need not be the case, for example, the pixels may be elongate in a certain direction, for example, having a factor of between 1.1 and 4 or more between two orthogonal dimensions thereof.

In another non-limiting example, the pixel pitch (i.e., spacing between pixels), is symmetrical in two directions, for example, about 2.5 mm or about 1.25 mm or about 1 mm, or about 2 mm or about 3 mm, or larger, or smaller or intermediate values. In another example, the pixel dimension in one direction is different than the dimension in another direction, for example 2×3 mm, 1.5×2.5 mm, 2×2.5 mm, etc.

In some exemplary embodiments, the detectors have dimensions in the range of about 1 cm to about 15 cm, for example in the range of 2 to 8 cm, for example in the range of 3 to 5 cm, for example 4 cm.

Exemplary Reconstruction Variations

In some exemplary embodiments of the present invention photons are detected by solid state detectors and electronic circuitry that are configured for acquisition of single photons of typical SPECT energy levels, and/or single photons of high energy such as 511 KeV, and/or coincidence detection of pairs of photon received as a result of a single positron emission from the radiopharmaceutical. In exemplary embodiments of the invention detector modules are capable of detecting more than one of these modes, for example detecting a wide range of energies single photons such as from 40 KeV to 511 KeV. In other exemplary embodiments of the invention detector modules are capable of detecting 511 KeV photons both as single events (if coincidence of a pair of photons was not detected) and as coincidence photons detection.

In an exemplary embodiment of the present invention a collimator is used on the detector which provides wide collection angle of 511 KeV, but with some preferred orientation of detection (for example, about 20%, or 30%, or 50%, or 70%, or 100% or 150% or 200% or 300% higher probability in a certain direction (e.g., having an angular aperture of between 0.001 and 10 degrees in a largest dimension) compared with most other directions, for example about 100% higher, which is about twice the probability, in a main direction).

In an example, information from photons that are detected as part of a coincidence is processed by the reconstruction algorithm as being probably received from a location along a line of sight between the two detection locations, and information from photons that were detected only in one location with no detection of the coincidence can be either ignored or being processed in a SPECT-like probability analysis based on the detection probability function ("functional", detection probability map) which depends on the collimator properties and its preferred orientation.

In an example, the reconstruction algorithm combines information from both SPECT-like analysis and coincidence-like analysis. In an example, the analysis based on individually detected photons (as a single detected photon, and/or as each of a pair of coincidence photons) is used to form an interim information, for example interim reconstruction of the radiopharmaceutical distribution in 3D volume, and that interim information is used as a prior information to a further 3D image reconstruction based on coincidence analysis. In this approach, for example, analysis based on one approach is either fully integrated with, and/or iteratively integrated with, and/or used as a prior info for, analysis based on the other approach. In an example, PET-like analysis serves as prior knowledge for SPECT-like analysis. In an example, SPECT-like analysis serves as prior knowledge for PET-like analysis. In an example, the SPECT-like analysis and the PET-like analysis are iteratively performed, either one providing for preprocessing or prior knowledge for the other, or one serves for post-filtering of the other, or algorithms merged with one-another, or any combination thereof.

In an exemplary embodiment of the invention, when reconstructing data from multiple energies, a priori probability of correlation between two energies is optionally used. For example, for a given body structure, the apriori probability of a SPECT event (or event at one energy) may be different from the a priori probability of a SPECT or PET event at a different part of the structure and/or at the same part. Optionally, a previous image is used as an input to indicate the differences in radiopharmaceutical distributions at the different detected energies. In one example, heart muscle is detected using one energy and a diseased location in the heart is detected using another energy. Reconstruction of the shape and/or location of the heart using the first energy may be used to limit (e.g., anchor) the other energy to fit within the boundaries of the heart as reconstructed by the first energy or as matching a model sized and shaped using the first energy.

In an exemplary embodiment of the present invention the reconstruction algorithm is adaptive to take into account variable location of the detectors. Unlike conventional PET, where the algorithm assumes that detectors positions and orientation is known and fixed in advance, and in particular the relative location and orientation of the detectors is known (one detectors relative to the other detectors), in an example of the present invention the algorithm forms probability distribution maps that factor the de-facto location of the detectors during the acquisition, as customized per patient and/or instant of time.

In an example, the distance between detectors and the body, the location of the detectors in space and the relative position of the detectors (one relative to others) varies from one detector to another and from one patient to another. Moreover, in an example, the algorithm is configured differently than conventional PET-reconstruction algorithms to form probability maps for photons to be detected by a detector, to be calculated based on the location and orientation of the detector during the acquisition. The probability to obtain coincidence detection changes as the detectors move and are positioned closer to the body, as the line of sight between any two detectors becomes different than that which was pre-fixed in conventional ring-based detectors.

In an example, a 3D image reconstruction algorithm calculates a probability function ("the functional") of a radiopharmaceutical for a voxel (a small volume in a certain 3D location in space) to emit a positron that converts to 2 photons (following annihilation of the positron) that would be detected as a coincidence event by a pair of pixels (one from each of two opposing detectors), taking into account the position of the detectors and their orientation as a result of the detector motion in-out towards the body. In an example, the probability of detection as a single photon event is calculated too, taking into account, for example, the position of the detectors as a result of the detector motion in-out towards the body and/or collimator or detector design. In an example, the orientation of the detectors is also being used as part of the calculation of the probability function.

In an example, the detectors also move laterally, for example by motion of the gantry and/or linear motion and/or rotation thereof, and the reconstruction algorithm forms the probability functions taking into account the gantry lateral motion and its effect on the position and orientation of the detectors. In some examples, such motion is done before photon acquisition begins, and the algorithm accounts for it. In another example, such motion occurs during photon acquisition process, and the algorithm accounts for it by having the probability function calculated to take into account the dynamic changes due to the relative motion during the scan.

In an example, the detectors rotate around one or more local axes, for example by rotating around an axis of rotation per detector structure (or per group of detectors), for example, independently rotating detectors (or groups) around an axis which is more-or-less parallel to the main axis of the patient body. In this example, the reconstruction algorithm forms the probability functions taking into account the detector rotation. In some examples, such rotation is done before photon acquisition begins, and the algorithm accounts for it. In another example, such rotation occurs during photon acquisition process, and the algorithm accounts for it by having the probability function calculated to take into account the dynamic changes due to the orientation changes during the scan.

In an example, a combination of the some or all of above components of the reconstruction algorithm is used to enable adaptation of the reconstruction algorithm and use of the probability functions taking into account the ability of the detectors to move before and/or during the scan. For example, the adaptation is provided using a sensitivity or energy correction and/or by modifying the model of the detectors used in reconstruction. As noted herein, in some cases planning or RT acquisition is modified, for example, to ensure a sufficient photon count from a desired location, to ensure a desired quality, to avoid data collection from undesired regions and/or to ensure stability of reconstruction.

In another example of the present invention the system is capable of simultaneously acquire high energy (e.g. PET, 511 KeV) and lower energy (SPECT, X-Ray) photons. In an example, such simultaneous acquisition of photons from multiple energy levels allows simultaneous image acquisition of multiple radiopharmaceuticals. For example, simultaneous imaging of radiation from PET isotope (e.g. radiopharmaceutical based on one or more of F-18, C-11, N-13, O-15, Rb-82, Cu-62, Ga-68, Iodine), and from a SPECT isotope (e.g. radiopharmaceutical based on one or more of $Tc^{99m}$, $Tl^{201}$, $I^{123}$, $In^{111}$). In an example, the acquisition of photons emitted by two or more radiopharmaceuticals is simultaneous, and the image reconstruction algorithm generates 3D images of the distribution of two or more radiopharmaceuticals within the ROI, thus avoids problems associated with registration of images from different sources that are acquired by different systems and/or at different time.

While the term PET has been used for convenience, other coincidence detection methods may be used. Similarly, other single photon detection methods than SPECT may be used.

Such a system as described herein may be selectively operated, for example, in a single mode (coincidence or non-coincidence) and/or in a dual mode.

In an exemplary embodiment of the invention, for coincidence detection, time stamps per photon are obtained at about microseconds or sub-microsecond resolution, and time-of-flight processing is optionally obtained if timestamp is obtained at sub-nanosecond resolution. In these cases, a processing means, such as a central CPU (in this or other embodiments) can identify the matching photons and analyze the coincidence emission line, and if available also the estimated position along the line based on time-of-flight calculation.

Collimator Arrangements and Configurations:

FIGS. 17-22D illustrate exemplary collimator configurations, including, for example designs that are adjustable to provide high and low spatial resolution. This capability may be advantageous for SPECT imaging using N-M tomography systems providing adjustable bore geometry as discussed below, and also to permit selectably using the same detector units for PET or SPECT imaging, or for both PET and SPECT imaging simultaneously. In some embodiments, no physical adjustment is applied, for example, using software correction to adapt the received signal for different desired collimation conditions.

Figure 17:
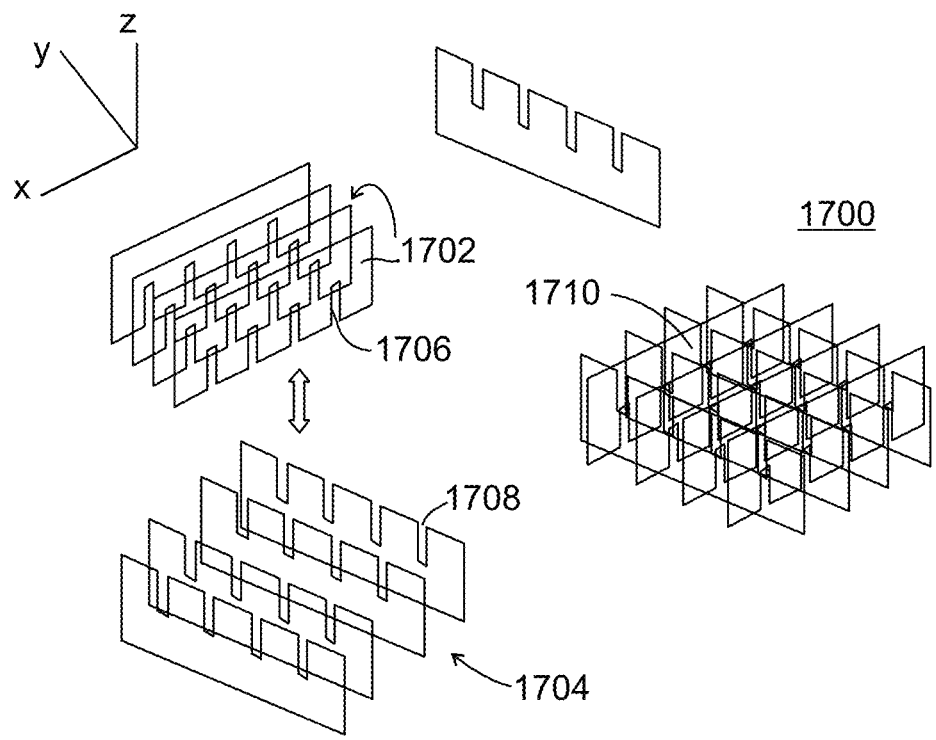
FIG. 17 illustrates the construction and assembly of a basic collimator.

Referring first to FIG. 17, there is shown a representation of an exemplary basic adjustable collimator designated 1700. For reference purposes, the Z-direction is taken as perpendicular to the plane of the sensor element and the Y-direction is the direction parallel to the machine or patient axis, The X-direction is orthogonal to the Y and Z axes, and with the Y-axis defines a plane parallel to the plane of the sensor element. It is note that non-rectangular collimators may be used, for example, hexagonal.

As illustrated in FIG. 17, collimator 1700, is formed of two orthogonal sets of septa 1702 and 1704. Septa 1702 lie in X-Z planes (spaced in the Y-direction). Septa 1704 lie in Y-Z planes (spaced in the X-direction). Septa 1702 are formed with slits 1706 at spaced intervals in the X direction. Septa 1704 are formed with slits 1708 at spaced intervals in the Y direction. The spacing between slits 1706 corresponds to the X-direction spacing (or multiples thereof) of septa 1704, while the spacing between slits 1708 corresponds to the X-direction spacing (or multiples thereof) of septa 1702.

Septa 1702 and 1704 fit together as shown to form an "egg-crate" array of collimator cells 1710 that can easily be assembled. As illustrated, the spacing of septa 1702 (in the Y direction) and 1704 (in the X direction) are the same so that cells 1710 are square. However, it should be understood that the septa spacing can be different in the X and Y directions so that cells 1710 are rectangular. Another variation is to make the slit spacing and/or the spacing of septa 1704 non-uniform allowing different size cells at different locations in the collimator. These variations are simple to achieve with the illustrated design. A plastic frame (not shown, optionally positioned between the collimator and the ROI) is optionally used to press the septa together and against the detector, for example, using one or more screws to provide the pressure. Other attachment mechanism may be used as well, for example conneceters which interconnect the speta and/or attach a flange at the end of one or more septa to the detector.

Figures 18A, 18B, 18C:
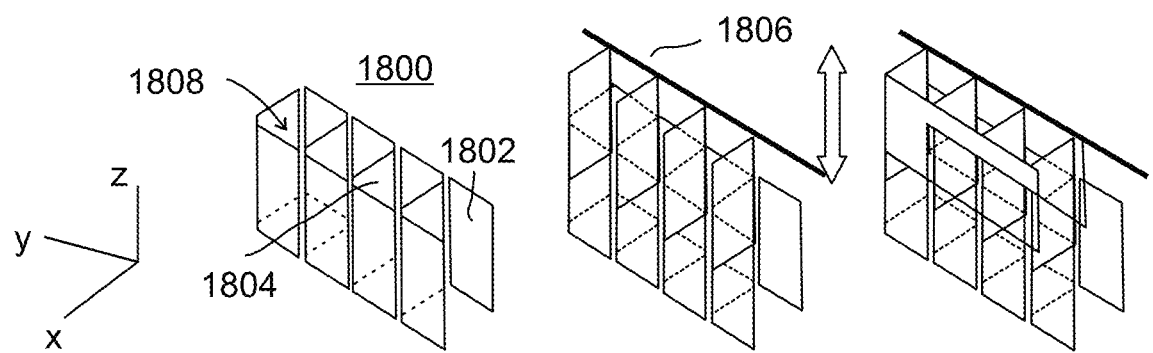
FIGS. 18A-18C illustrate some exemplary (but non-limiting) ways to vary the resolution of collimators according to some embodiments of the invention by lengthening or shortening the collimator septa.

18A-22D illustrate exemplary (but non-limiting) ways to vary the resolution of collimators according to some embodiments of the invention. Before proceeding to a description of some of these embodiments, the following points should be noted:

1. FIG. 18A shows a fragment 1800 of a collimator formed by spaced Y-Z plane septa 1802 and X-Z plane septa 1804. These define collimator cells 1806 (four of which are shown) that provide photon travel paths to the detector element. For simplicity, FIGS. 18A-22D show only part of a single row of the collimator. The full collimator generally includes multiple (e.g., 4, 10, 20, 30 or intermediate or greater numbers) parallel rows like 1800. Also, while only four cells 1806 are shown, the actual number of cells (as well as the number of parallel rows 1800) will depend on the overall dimensions of the emission detector element, and the pitch of the septa (e.g., the spacing between septa or septa centers).

2. In some embodiments, the septa pitch in the Y-direction is the same as that in the X-direction whereby the individual collimator cells 1806 are square. Alternatively, the septa pitch in the Y-direction is different from that in the X-direction whereby the individual collimator cells 1806 are rectangular. Alternatively or additionally the pitch can be variable in the X and/or Y directions. In some embodiments the septa are not straight. For example, the arrangement may be of radially (e.g., extending from one or more points) arranged fixed septa and circular speta mounted thereon. Optionally or alternatively, one or more septa may be inclined away from a perpendicular to the detector.

3. In some embodiments, in addition to or instead of different pitch in the X and/or Y directions, and/or variable pitch in the X and Y directions, the septa thickness may be different in the X and/or Y directions. As an additional or alternative option, the septa thickness may be variable in one or both the X and Y directions. As another alternative or additional option, the septa length may be different in the X and Y directions. As yet another alternative or additional option, the septa length may be variable in one or both the X and Y directions. The variation within a detector collimator for one or more of these parameters may be, for example, within a factor of 1.1, 2, 3, 4, or intermediate or greater factors. Thus, some embodiments provide non-uniformly sized and/or shaped collimator cells.

4. Collimator configurations and geometry variations as illustrated in FIGS. 18A-22D can be used with both pixilated and with non-pixilated detectors.

5. Conventional PET detectors do not include collimators. However, it has been found that certain materials, for example, tungsten and the others mentioned above more efficiently absorb photons having energy in the 40-250 KeV range emitted by tracers used for SPECT imaging than the high energy (511 KeV) PET photons. Forming the collimator septa of such materials helps make it possible to use detectors having collimators as described herein for both PET and SPECT imaging with only slightly less efficiency (i.e., sensitivity, e.g., 30%, 20%, 10% or intermediate or smaller reduction of sensitivity) in the PET mode, but with wider effective viewing angle (i.e., angle of acceptance) since the high energy photons are able to pass multiple septa, for example, 3, 4, 5 or 6 septa. Stated differently, despite the decrease in detection probability (resulting from decreased sensitivity as the angle of acceptance increases), useful SPECT detectors can still provide high effective sensitivity for PET detection.

6. In exemplary embodiments, blockage for PET energies is less than 80%, 60%, 50%, 20% or intermediate percentages depending, for example, on the acceptance angle, septa design, and/or material as described herein. As a specific non-limiting example, the collimator may be formed of tungsten septa about 0.2 mm in thickness, and having 1.03 mm square cells, with a pitch of 1.23 mm and height in the Z-direction of 14.5 mm, and overall horizontal septa length of 10.8 mm.

7. Use of wide angle reconstruction techniques for SPECT imaging, for example, the ML-EM algorithm, allows a single adjustable-geometry collimator to be used for SPECT imaging for multiple distances between the detector and the target area, e.g., a range factor of 1.5, 2, 3, 5 or intermediate or greater values. Suitable known reconstruction techniques for PET imaging include without limitation, FBP (filtered back projections), iterative algorithms with or without PSF (point spread function), and modeling. These may also permit collimated detector units formed for example, of tungsten septa to be used for PET imaging to detect photons over a range of detector angular extent along the system axis, for example, e.g., a range factor of 1.5, 2, 3, 5 or intermediate or greater factors.

8. It should further be noted that conventional SPECT algorithms assume a collection angle and a detection probability map (resulting from the collimation and perhaps other factors) that is part of the algorithm. In PET imaging, as the detectors are exposed to the entire imaged volume, the coincidence line is used for the reconstruction process. However, in the some of the exemplary embodiments, the variable septa geometry affects PET reconstruction to some extent, in steps—sensitivity being changed (and generally reduced with some steps) as the detection angle increases. In an exemplary embodiment of the invention, the algorithms suitable for PET image reconstruction advantageously take account of the septa configuration to attribute to photons coming from a particular coincidence line a detection probability, such that the probability is factored into the calculation: lower probability means that the source in that direction is actually "hotter"/"brighter" than it looks. Therefore, the value attributed to radiation received by a particular pixel is related to the counts received from that direction divided by the probability of detection from that location. This concept is valid for both SPECT and PET reconstruction because the probability of detection varies in different angles related to the existence of the collimator and the septa configuration, but also the fact that different angles of detection hit different effective thickness of septa, the fact that collimation may be variable, and/or the variable geometry of the detector heads as previously described.

FIGS. 18A-18C illustrate an embodiment in which spatial resolution is enhanced by lengthening the Y-Z plane septa 1802 and/or the X-Z septa 1804 thereby narrowing the angle of photon acceptance.

In FIG. 18A, collimator fragment 1800 is shown in an un-elongated configuration which provides a wide angle of acceptance for SPECT imaging. for example, ranging from about 1 and about 30 degrees, and advantageously, between about 5 and about 15 degrees FIG. 18B shows elongation of the collimator in the Z-direction to reduce the angle of acceptance and thereby improve the spatial resolution. FIG. 18B shows extension of only the X-Z plane septa 1804, while FIG. 18C shows elongation of both the X-Z septa and the Y-Z septa. It should be understood that alternatively for the situation illustrated in FIG. 18B, the Y-Z plane septa 1802 can be extended instead of X-Z plane septa 1804.

Extension and retraction of septa 1802 and 1804 may be achieved by any suitable and desired mechanism. This is shown schematically as a coupling rod 1806 for septa 1804, A small motor, for example a stepper motor or a multiple position relay (not shown) attached to coupling rod 1808 provides for step-wise movement. Alternatively, continuous adjustment can be provided, for example, by a suitable motor and position sensors. The septa can also be extended and retracted manually.

Extending either septa 1802 or 1804 as described can be useful, for example to increase resolution in a certain orientation—while possibly reducing sensitivity in that direction. Retracting the septa does the opposite. In an exemplary embodiment of the invention, tilting of speta (e.g., by moving a bore-side thereof while using the detector side as a pivot) is used for when the detector is rotated out of plane during arrangements as described above. A louver-like mechanism may be used.

In an exemplary embodiment of the invention, the reconstruction algorithm is adapted for the collimator configuration, for example, based on a look-up table with different parameters for different collimator configurations. Optionally, a sensor which reports the collimator configuration or the command for collimator adjustment is used to calculate such parameters and/or as input to a reconstruction algorithm. Which uses such measurement to modify the reconstruction (e.g., sensitivity correction and desired count rate for stability of reconstruction and/or image quality).

In an exemplary embodiment of the invention, planning of data acquisition takes into account possible collimator variations, for example, by calculating desired configurations and/or by comparing options with different collimator arrangements.

In an exemplary embodiment of the invention, when acquisition depends on pervious acquisition, collimator and/or detector configuration are changed in a manner which preferentially provides data (photon detections) from a desired location and/or time and/or to preferentially block data from a certain location and/or time.

Figures 19A, 19B:
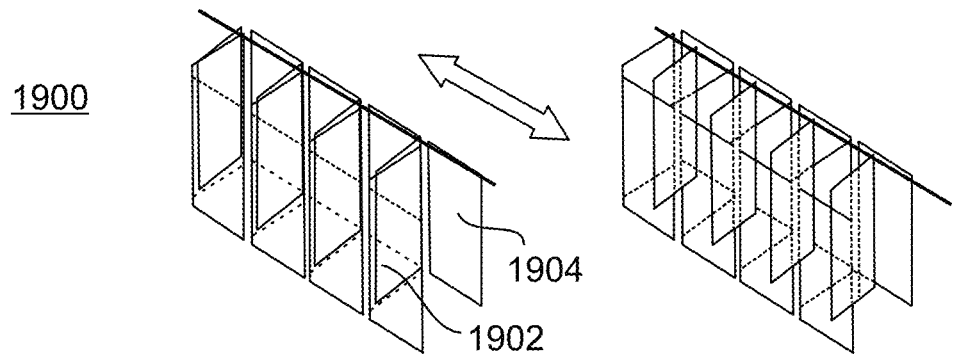
FIGS. 19A and 19B illustrate exemplary (but non-limiting) ways to vary the resolution of collimators according to some embodiments of the invention by sliding the septa laterally.

FIGS. 19A and 19B illustrate an embodiment in which the pitch of the septa is varied. FIG. 19A shows a collimator fragment 1900 comprised of X-Z plane septa 1902 and Y-Z plane septa 1904 defining collimator cells 1906. FIG. 19A shows a configuration in which the X and Y dimensions of the collimator elements are equal. FIG. 19B shows X-Z plane septa 1902 shifted in the Y-direction by one-half the septa pitch. Alternatively, Y-Z plane septa 1942 may be shifted (in the X-direction). In either case, the cross-sectional area of the opening in collimator cells 1906 is reduced by for example, 25-75 percent, for example, 50 percent thereby decreasing the acceptance angle and increasing the spatial resolution.

In some embodiments, both (some or all thereof) the X-Z and Y-Z plane septa 1902 and 1904 can be shifted, thereby reducing the area of the collimator cell openings, for example, by 75 percent, and further decreasing the acceptance angle and correspondingly increasing the spatial resolution.

Moving septa 1902 and/or 1904 can be effected using an arrangement similar to that described in connection with FIGS. 18A-18C (but adapted to provide Y-direction movement) or in any other suitable and desired manner.

Figures 20A, 20B:
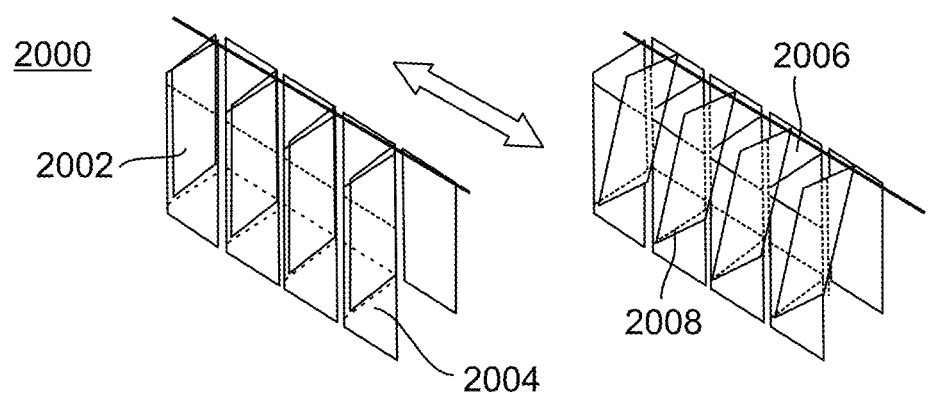
FIGS. 20A and 20B illustrate exemplary (but non-limiting) ways to vary the resolution of collimators according to some embodiments of the invention by tilting and/or shifting the septa.

FIGS. 20A and 20B illustrate another embodiment in which the pitch of the septa is varied. In FIG. 20A, a collimator fragment 2000, is formed by X-Z plane septa 2002 and Y-Z plane septa 2004 defining collimator cells 1906. As in FIG. 19A the septa pitch is the same for septa 2002 and 2004.

FIGS. 20A-20B show the upper ends of X-Z plane septa 2002 tilted in the Y-direction by one-half the septa pitch. Alternatively, Y-Z plane septa 1942 may be shifted (in the X-direction). In either case, the area of opening in collimator elements 1906 is reduced by, for example, by 25-75 percent, for example, 50 percent thereby decreasing the acceptance angle and increasing the spatial resolution.

The tilting may be achieved in generally the same manner as in the embodiments of FIGS. 18A-18C and 19A-19B, except that the bottom ends 2008 of septa 2002 are pivotally mounted. In some embodiments tilting provides a parallel collimation. In other embodiments, it provides a fan-in collimation or a fan-out collimation. Different adjustment and adjustment types may be provided for different detectors and/or for different parts of a same detector, for example, during a same session or even simultaneously, for example, responsive to ROI location, ROI type, time form injection of tracer and/or arm and/or bore geometry.

FIGS. 21A-21D illustrate resolution adjustment using an arrangement of layered or vertically tandem collimator sub-units or parts, in accordance with some embodiments of the invention. FIGS. 21A and 21B are respectively an end elevation and a side perspective view of a two part collimator fragment 2100 comprised of first sub-unit 2102 and a second sub-unit 2104 located above sub-unit 2102. In this context, the word "above" is to be understood as meaning closer to the detector element. Therefore, sub-unit 2102 is positioned closer to the source of radiation than sub-unit 2104.

Sub-unit 2102 is formed a first set of septa 2106 extending in an X-Z plane, and a second set of septa 2108 extending in a Y-Z plane. Sub-unit 2104, in contrast, is formed only of one set of septa 2110 extending in the X-Z plane. Alternatively, sub-unit 2104 can be formed of two sets of septa like sub-unit 2102.

Also, while sub-unit 2104 is above sub-unit 2102, alternatively, the sub-units can be reversed so that sub-unit 2102 is above sub-unit 2104.

FIG. 21B shows two ways the collimator cells of collimator 2100 may be decreased in size to provide a smaller acceptance angle, and therefore higher resolution for SPECT imaging: septa 2108 can be moved in the X-direction and septa 2110 can be moved in the Y-direction. If only septa 2108 are moved, the area of the cell openings is decreased by up to 50 percent. If both sets of septa 2108 and 2110 are moved, cell opening area can be decreased by up to an additional 25 percent.

FIG. 21C illustrates an alternative collimator configuration 2112 comprised of an upper sub-unit 2114 formed by X-Z plane septa 2118 and a lower sub-unit 2116 formed by X-Z plane septa 2120 and Y-Z plane septa 2122. In this embodiment, sub-unit 2114 includes a second set of X-Z plane septa 2124 positioned between septa 2110, and sub-unit 2102 includes a second set of Y-Z plane septa, one of which is shown at 2126 positioned between septa 2122. In this configuration, only intermediate septa 2114 and 2126 are moveable.

FIG. 21D shows a further alternative embodiment 2128 in which the septa are configured as in the embodiment of FIG. 21B except that the septa 2122 and 2130 are tiltable rather than slidable in the Y and X directions, respectively.

An un-illustrated variation of collimator 2112 of FIG. 21C has three sub-units or parts in vertically tandem relationship. The three parts may be of equal length in the Z-direction, or any other desired proportion, for example, 1:2:1 (i.e., so that middle part is twice as long as the top and bottom parts and thereby provides one-half the length of the collimator. Other proportions are also possible.

Optionally, collimator resolution in this embodiment is increased by moving the Y-Z plane septa forming the middle part in the X and/or Y directions as in the embodiment of FIG. 21C. Optionally or additionally, septa forming the top and bottom parts are moved.

Another un-illustrated three-part collimator is similar to collimator 2128 of FIG. 22D, in which resolution is increased by tilting the septa of the central part.

The three layer configurations may be desirable in that they may provide a more symmetrical high resolution pattern in the X and Y directions.

FIGS. 22A-22D illustrate embodiments in which the opening area of the collimator cells is changed by shutter-like mechanisms. In FIGS. 22A and 22B, collimator fragment 2200 is formed by X-Z plane septa 2202 and Y-Z plane septa 2204 that define collimator cells 2206. At the upper ends of cells 2006 are pairs of cooperating triangular shutter leaves 2208 and 2210. Shutter leaves 2208 may be fixed in place while leaves 2210 are slidable in the X direction, for example, by an actuator rod 2212. In the open position illustrated in FIG. 22A leaves 2210 substantially overlie leaves 2208. In the closed position illustrated in FIG. 22B leaves 2210 have been shifted to partially close the tops of cells 2006.

FIG. 22C illustrates an embodiment in which the tops of the collimator cells 2206 are closed by rotating flaps or leaves 2214 on a mechanism shown schematically as an actuator rod 2216.

FIG. 22D illustrates an embodiment in which the tops of the collimator cells 2206 are closed by an iris-like shutter 2218. This embodiment may be advantageous in that it allows achievement of very small area openings for the collimator cells. Actuation of shutter 2218 may be by a convention rotating mechanism, as in a photographic camera, or in any other suitable and desired way.

The dimensions of the collimators illustrated in FIGS. 18A-22D may be varied over ranges, for example, as indicated in the non-limiting examples given below.

1. The pitch of the collimator septa may be in the range of about 1 mm to about 3 mm. Larger or smaller pitch values are also possible.

2. Typical septa thickness may be in the range of about 0.2 mm to about 0.3 mm. Again, larger or smaller thicknesses are also possible.

3. The height of the septa (in the Z-direction) may be in the range of about 13 mm to about 25 mm, or larger or smaller values.

4. The length of the septa (in the X and Y directions) may range from about 8 mm to about 20 mm or larger or smaller values.

Exemplary Relationships Between Collimator and Pixilated Detector Configurations:

The following discussion describes some embodiments as non-limiting examples of collimator configurations in relation to pixilated detectors, using the above collimator designs or using other collimators, such as machined slabs.

In a first embodiment, the collimator septa are aligned with the pixel-pitch of the detector, i.e., the septa are positioned at the borders of each pixel. In such a configuration, the collimator cells are aligned with the detector pixels with one pixel per collimator cell.

In another embodiment, the septal pitch in one direction, (e.g., the X direction as defined in connection with FIGS. 17-18A-C), or the other direction (or both) is greater than the pixel pitch, for example, in an integer ratio, of 1:2 or 1:3, or 1:4, or 1:5, or greater. In such an arrangement, if the septal pitch matches the pixel pitch in one direction, and is two times the pixel pitch in the other direction, there will be two pixels within each collimator cell. If the septal pitch is twice the pixel pitch in both directions, there will be four pixels in each collimator cell. This configuration may allow the generation of multiple different views within the same collimator cell. In other embodiments the septa are not aligned with some or all pixel boundaries.

In a further embodiment, all the septa in one or both the X-Z and Y-Z planes (also as previously defined may be oriented so that they are not parallel to each other. This configuration forms a collimation structure in which multiple pixels have different views, passing through the same cell. In one example, a multiple pinhole structure is provided. In one example, multiple apertures are provided. In another example, the multiple apertures are arranged to form coded aperture collimation structure, for example of a type known in the art.

It should be noted that coded aperture techniques are known to those skilled in the art for use in gamma ray imaging, and will not be described here in the interest of brevity.

In another embodiment, the septa pitch is smaller than the pixel pitch, for example, according to an integer ratio, of 1:2, or 1:3, or 1:4, or 1:5 or greater. This may be achieved by positioning one or more additional septa at the middle of a pixel to provide, multiple collimator cells within each pixel. With this configuration it is possible to obtain a particular viewing angle (collection angle) with shorter collimator septa. For example, if for a certain desired collection angle one would use a pixel pitch of 2.5 mm and a single collimator cell per pixel with septa length of about 20 mm, similar performance can be obtained by providing two collimator cells per pixel with a septa length of 10 mm. Shorter septa may be advantageous since they may permit having a smaller detector head with better maneuverability.

In another embodiment, the collimator cell pitch is different in the X and Y directions, and also different than the pixel pitch. For example, the collimator septa may be pitched at 2 mm in one direction and at 3 mm in the orthogonal direction. In general, the septa spacing may be larger or smaller than the pixel spacing and also different in the X and Y directions/pitch. For example, N collimator septa may be evenly spread over K pixels in the X direction, and M collimator septa may be evenly spread over L pixels in the Y direction.

In a further exemplary embodiment of the invention the length of the collimator septa is different in the X and Y directions. For example, in the case of pixel pitch of about 2.5 mm, the X-Z plane septa can be about 18 mm long and the Y-Z plane septa can be about 24 mm long. With this exemplary configuration it is possible for a pixilated detector having square pixels to provide different view angles and collection angles in each direction and to allow sensitivity and resolution of reconstruction to be optimized where the camera scanning is very asymmetric in its nature.

For example: a camera scan and reconstruction may form many X-Z "slices" along the Y axis which is parallel to patient body main axis and the Y resolution of the detector is very influential on the reconstruction resolution in the Y axis. This is different than the X-Z resolution, as the depth dimension is obtained by different views and rotations within the X-Z plane, where the X resolution of detector is just one factor and the distance, rotations, translations and reconstruction algorithm determine the resulting resolution. In these cases it may well be that an improved result can be obtained with a collection angle which is different in X axis than in Y axis. This is optionally achieved with this unique approach of different septa length in the X-Z and Y-Z planes.

EXAMPLE

Figure 23A:
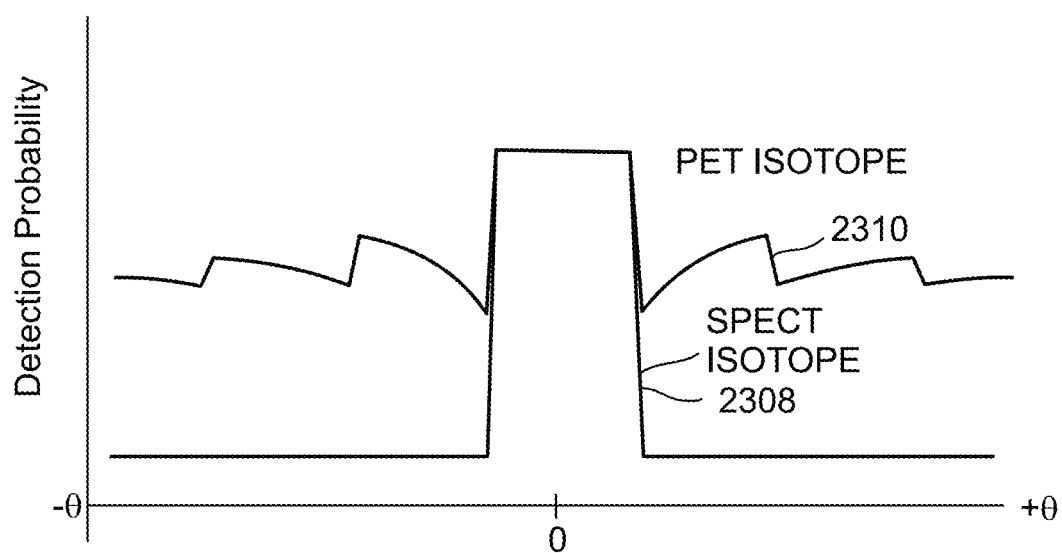
FIGS. 23A-23C illustrate representative (qualitative) performance of collimator constructions and configurations according to some embodiments of the invention.
Figures 23B, 23C:
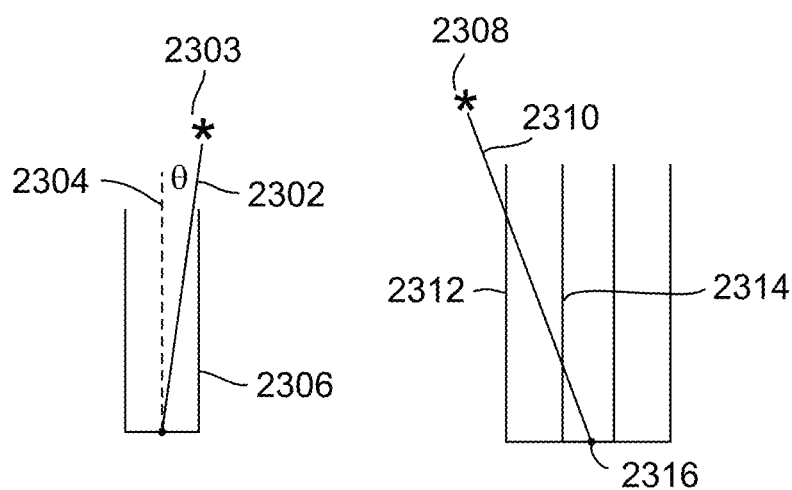

FIGS. 23A-23C illustrate qualitatively the result of a simulation study performed on an exemplary collimated detector as described herein formed of 0.2 mm tungsten septa. In FIG. 23A, the horizontal axis represents ±θ, the angle between an approach path 2302 from an emission event 2303 off the centerline 2304 of a collimator cell 2306 (see FIG. 23B), two curves are shown: curve 2308 for a typical SPECT isotope, and 2310 for a typical PET isotope. As may be seen, SPECT performance is very directional, but for small values of θ, PET performance is comparable.

However, for PET isotopes, off-axis detection is reduced, but not by so much as to prevent use of collimated detectors according to some embodiments hereof for selectable or simultaneous SPECT and PET imaging.

FIG. 23C provides an understanding of the saw-tooth shape of the off axis detection probability for PET imaging. Here, it may be seen that the path 2310 for an emission event at some off-axis position 2308 must pass through two septa 2312 and 2314 to impinge on the center of a detector pixel 2316, and suffers additional attenuation.

Moreover, having the reconstruction algorithm compensate for the off-axis attenuation (e.g., with angle dependent sensitivity weighting, e.g., calculated and/or measured during calibration) can potentially improve PET performance significantly.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications, and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A nuclear medicine tomography system comprising:
    a detector carrier configured to be populated by a variable number of detector heads, said detector carrier including a plurality of mounting receptacles, each mounting receptacle configured for attachment thereto of a detector head;
    a plurality of detector heads configured to:
        attach to said plurality of mounting receptacles; and
        extend and retract with respect to said detector carrier to establish a variable bore size;
    wherein each detector head of said plurality of detector heads comprises an arm and at least one detector element, said at least one detector element configured to be movable relative to said arm during a scan;
    a controller configured to
        receive population information for a first one or more mounting receptacle(s) of said plurality of mounting receptacles regarding attachment of a first one or more detector head(s) of said plurality of detector heads thereto,
        control, based on a desired bore size and said population information, extension and retraction of said first one or more detector head(s) of said plurality of detector heads to a spatial arrangement thereof as defined by said extension and retraction,
        control data acquisition by a second one or more detector head(s), of said plurality of detector heads, that forms a bore of the desired bore size, and
        control image reconstruction on the acquired data;
    wherein the controller is further configured to control at least one of said data acquisition and said image reconstruction, based on said population information and/or said spatial arrangement,
    wherein said system is configured to operate, including performing said scan and said data acquisition, even when fewer than all mounting receptacles of said plurality of mounting receptacles have detector heads respectively attached thereto.

2. The nuclear medicine tomography system of claim 1, wherein said controller is configured to receive detector type information for a second one or more mounting receptacle(s), of said plurality of mounting receptacles, when said second one or more detector head(s) is/are respectively attached thereto, wherein said detector type information comprises one or more detector type(s) of said second one or more detector head(s),
    wherein said controller is further configured to control, based on said detector type information at least one of:
        said data acquisition by said second one or more detector head(s); and
        said image reconstruction.

3. The nuclear medicine tomography system of claim 2, wherein said controller is configured to receive said detector type information for each mounting receptacle, of said plurality of mounting receptacles, that has a respective detector head, of said plurality of detector heads, attached thereto.

4. The nuclear medicine tomography system of claim 2, wherein said controller is configured to receive data from a third one or more detector head(s), of said plurality of detector heads, when said third one or more detector head(s) are respectively mounted to a third one or more mounting receptacle(s) of said plurality of mounting receptacles.

5. The nuclear medicine tomography system of claim 2, wherein said controller is configured to:
    receive said population information from said first one or more detector head(s), and/or
    receive said detector type information from said second one or more detector head(s).

6. The nuclear medicine tomography system of claim 2, wherein,
    said first one or more detector head(s) is/are configured to provide to said population information to said controller and/or said second one or more detector head(s) is/or configured to provide said detector type information to said controller.

7. The nuclear medicine tomography system of claim 2, wherein said plurality of detector heads includes detector heads of different types.

8. The nuclear medicine tomography system of claim 1, wherein said controller is configured to receive said population information for each mounting receptacle of said plurality of mounting receptacles.

9. The nuclear medicine tomography system of claim 1, wherein said controller is configured to receive manually provided data.

10. The nuclear medicine tomography system of claim 1, comprising a patient carrier, wherein said first one or more detector head(s) is/are configured to extend and retract with respect to said patient carrier.

11. The nuclear medicine tomography system of claim 10, wherein said variable bore size is 20-90 cm.

12. The nuclear medicine tomography system of claim 10, wherein said first one or more detector heads is/are configured to rotate relative to one or more respective longitudinal axis/axes thereof during performance of said scan.

13. The nuclear medicine tomography system of claim 12, wherein said first one or more detector heads is/are configured to tilt by rotation of said first one or more detector head(s) around an axis parallel to an axis of elongation of said patient carrier.

14. The nuclear medicine tomography system of claim 10, wherein said detector carrier is configured to be rotatable about an axis of said patient carrier.

15. The nuclear medicine tomography system according to claim 1, wherein said first one or more detector head(s), is/are configured to orient angularly to prevent interference between adjacent detector heads thereof when said first one or more detector heads is/are extended to a desired position forming said spatial arrangement.

16. The nuclear medicine tomography system of claim 1, wherein said controller is configured to control motion of said first one or more detector head(s).

17. The nuclear medicine tomography system of claim 16, wherein said controller is configured to prevent collision of said first one or more detector head(s) with each other.

18. The nuclear medicine tomography system of claim 16, wherein said controller is configured to prevent said first one or more detector head(s) and/or said second one or more detector head(s) from obscuring a field of view of said second one more detector head(s).

19. The nuclear medicine tomography system of claim 16, wherein said controller is configured to control said image reconstruction based on said population information, said population information including one or more respective location(s) of said second one or more detector head(s).

20. The nuclear medicine tomography system of claim 16, wherein said controller is configured to control said image reconstruction based on said population information, said population information including one or more respective variable location(s) of said second one or more detector head(s) during a photon acquisition process of said data acquisition.

21. The nuclear medicine tomography system of claim 1, wherein said plurality of detector heads includes detector heads of different qualities.

22. The nuclear medicine tomography system of claim 1, wherein each detector head of said plurality of detector heads is a SPECT detector head.

23. The nuclear medicine tomography system of claim 1, wherein said plurality of detector heads comprise a combination of SPECT detector heads and PET detector heads or comprise dual purpose SPECT-PET detector heads.

24. The nuclear medicine tomography system of claim 1, further comprising an electronic signal processor selectably operable to individually reconstruct a PET image or a SPECT image or operable to simultaneously reconstruct the PET and SPECT images.

25. The nuclear medicine tomography system of claim 1, wherein said plurality of detector heads consists of 3-18 detector heads.

26. The nuclear medicine tomography system of claim 1, wherein each detector head of said first one or more detector head(s) comprises a respective scintillator and a respective collimator.

27. The nuclear medicine tomography system of claim 26, wherein said respective scintillator comprises an array of pixels.

28. The nuclear medicine tomography system of claim 26, wherein said respective collimator of each detector head of said first one or more detector head(s) includes a plurality of septa, wherein each septum of the plurality of septa is moveable to change the geometry of the respective collimator to increase and decrease a spatial resolution of the each respective detector head of said first one or more detector head(s).

29. The nuclear medicine tomography system according to claim 1, wherein each detector head of said first one or more detector heads comprises:
    a PET-SPECT detector element responsive to gamma ray photons having energy in the range of about 40 KeV to 511 KeV; and
    a collimator configured to collimate SPECT photons and pass PET photons, thereby configuring the PET-SPECT detector for both PET and SPECT imaging.

30. The nuclear medicine tomography system according to claim 1, wherein said plurality of detector heads are positioned non-uniformly around said detector carrier.

31. The nuclear medicine tomography system according to claim 1, wherein said plurality of detector heads configured for non-rotation during said data acquisition.

32. The nuclear medicine tomography system according to claim 1, wherein, said second one or more detector heads is configured to make contact with a patient.

33. A method of using a nuclear medicine tomography system comprising:
    providing a nuclear medicine tomography system according to claim 1; and
    attaching said first one or more detector head(s) to said first one or more mounting receptacle(s) respectively.

34. The nuclear medicine tomography system according to claim 1, wherein at least one detector head of said plurality of detector heads includes an arcuate photon-collecting surface, and wherein said at least one detector element of said at least one detector head is movable relative to said arcuate photon-collecting surface.

35. The nuclear medicine tomography system according to claim 1, wherein said first one or more detector head(s) is/are laterally movable relative to a periphery of the detector carrier.

36. The nuclear medicine tomography system according to claim 1, wherein said controller is further configured to determine an imaging plan according to said population information.

37. The nuclear medicine tomography system according to claim 1, wherein said first one or more detector head(s) is/are movable to adjust a shape of said bore according to a region of interest.

38. The nuclear medicine tomography system according to claim 1, wherein said system is configured to operate, including performing said scan and said data acquisition, even when using fewer than all detector heads of said plurality detector heads.

39. The nuclear medicine tomography system according to claim 1, wherein, upon extending one or more detector head(s) of said first one or more detector head(s), said system is configured to operate, including said scan and said data acquisition, only using said second one or more detector head(s) consisting of the extended one or more detector head(s) of said first one or more detector head(s).

40. The nuclear medicine tomography system according to claim 1, wherein said spatial arrangement of said first one or more detector head(s) includes gaps between circumferentially adjacent detector heads thereof, said gaps being between 1 and 30 degrees, where said gaps between said circumferentially adjacent detector heads are maintained between 1 and 30 degrees for different populations of said first one or more detector head(s) and for different bore sizes.

41. The nuclear medicine tomography system according to claim 1, further including
  a patient carrier and
  a drive mechanism to rotate said first one or more detector head(s) around the patient carrier.

* * * * *